(12) United States Patent
Zheng

(10) Patent No.: US 9,263,681 B2
(45) Date of Patent: Feb. 16, 2016

(54) ORGANIC LIGHT EMITTING HOST MATERIALS

(71) Applicant: NITTO DENKO CORPORATION, Osaka (JP)

(72) Inventor: Shijun Zheng, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 14/102,138

(22) Filed: Dec. 10, 2013

(65) Prior Publication Data

US 2014/0159015 A1 Jun. 12, 2014

Related U.S. Application Data

(60) Provisional application No. 61/735,488, filed on Dec. 10, 2012.

(51) Int. Cl.
| | |
|---|---|
| C07D 401/14 | (2006.01) |
| C07D 403/10 | (2006.01) |
| C07D 403/14 | (2006.01) |
| H01L 51/00 | (2006.01) |
| H01L 51/50 | (2006.01) |

(52) U.S. Cl.
CPC .......... *H01L 51/0067* (2013.01); *C07D 401/14* (2013.01); *C07D 403/10* (2013.01); *H01L 51/0072* (2013.01); *H01L 51/5012* (2013.01)

(58) Field of Classification Search
CPC ... C07D 401/14; C07D 403/10; C07D 403/14
See application file for complete search history.

(56) References Cited

U.S. PATENT DOCUMENTS

| | | | |
|---|---|---|---|
| 6,620,529 B1 | 9/2003 | Ise et al. | |
| 6,835,469 B2 | 12/2004 | Kwong et al. | |
| 6,984,934 B2 | 1/2006 | Moller et al. | |
| 7,053,547 B2 | 5/2006 | Lu et al. | |
| 7,109,652 B2 | 9/2006 | Tsai et al. | |
| 7,321,193 B2 | 1/2008 | Antoniadis et al. | |
| 7,332,860 B2 | 2/2008 | Hatwar et al. | |
| 7,652,280 B2 | 1/2010 | Li et al. | |
| 7,678,959 B2 | 3/2010 | Okada et al. | |
| 7,834,546 B2 | 11/2010 | Krummacher et al. | |
| 8,426,040 B2 | 4/2013 | Zheng et al. | |
| 2002/0191130 A1 | 12/2002 | Liang et al. | |
| 2005/0106710 A1 | 5/2005 | Friedman et al. | |
| 2007/0103056 A1 | 5/2007 | Cok et al. | |
| 2008/0014464 A1 | 1/2008 | Kawamura | |
| 2008/0116784 A1 | 5/2008 | Krummacher et al. | |
| 2008/0311178 A1 | 12/2008 | Ishikura et al. | |
| 2009/0115319 A1 | 5/2009 | Kim et al. | |
| 2009/0134783 A1 | 5/2009 | Lin et al. | |
| 2009/0184633 A1 | 7/2009 | Kadoma et al. | |
| 2010/0060154 A1 | 3/2010 | Nomura et al. | |
| 2010/0326526 A1 | 12/2010 | Zheng et al. | |
| 2011/0140093 A1 | 6/2011 | Zheng | |
| 2011/0251401 A1 | 10/2011 | Zheng et al. | |
| 2012/0104277 A1 | 5/2012 | Morren | |
| 2012/0179089 A1 | 7/2012 | Sisk et al. | |
| 2012/0197179 A1 | 8/2012 | Khan et al. | |
| 2012/0223633 A1 | 9/2012 | Yoshinaga et al. | |
| 2012/0223635 A1 | 9/2012 | Mochizuki et al. | |
| 2013/0140534 A1 | 6/2013 | Lai et al. | |
| 2014/0163237 A1 | 6/2014 | Sisk | |
| 2014/0167014 A1* | 6/2014 | Liping et al. | 257/40 |

FOREIGN PATENT DOCUMENTS

| | | |
|---|---|---|
| CN | 101400658 | 4/2009 |
| GB | 2408209 | 5/2005 |
| JP | 02072370 | 3/1990 |
| JP | 2002275179 | 9/2002 |
| JP | 2006156445 | 6/2006 |
| JP | 2007-095444 | 4/2007 |
| KR | 2010075079 | 7/2010 |
| WO | WO0014174 | 3/2000 |
| WO | WO2004020388 | 3/2004 |
| WO | WO2004/049465 | 6/2004 |
| WO | WO2006101735 | 9/2006 |
| WO | WO2006130302 | 12/2006 |
| WO | WO2008/052350 | 5/2008 |
| WO | WO 2009/009695 | 1/2009 |
| WO | WO2009103165 | 8/2009 |
| WO | WO2010044607 | 4/2010 |
| WO | WO2011008560 | 1/2011 |
| WO | WO2011109671 | 9/2011 |
| WO | WO2012009283 | 1/2012 |
| WO | WO2012037269 | 3/2012 |
| WO | WO2012064987 | 5/2012 |
| WO | WO2012088294 | 6/2012 |
| WO | WO2012103380 | 8/2012 |
| WO | WO2014099864 | 6/2014 |

OTHER PUBLICATIONS

Aratani,Sukekazu et al., "Collimated Light Source using Patterned Organic Light-Emitting Diodes and Microlens", Japanese Journal of Applied Physics, vol. 49, No. 4, pp. 42101-42101 (2010).

Chen et al., "Versatile, Benzimidazole/Amine-Based Ambipolar Compounds for Electroluminescent Applications: Single-Layer, Blue, Fluorescent OLEOs, Hosts for Single-Layer, Phosphorescent OLEOs", Advanced Functional Materials, 2009, vol. 19, pp. 2661-2670.

Chi-Che Liu, Su-Hao Liu, Kun-Cheng Tien, Min-Hung Hsu, Hong Wer Chang, Chih-Kai Chang, Chih-Jen Yang, and Chung-Chih Wu, Microcavity top-emitting organic light-emitting devices integrated with diffusers for simultaneous enhancement of efficiencies and viewing characteristics; Appl. Phys. Lett. 94, 103302(2009).

G. Gustafsson, et al., "Flexible light-emitting diodes made from soluble conducting polymers," Nature, vol. 357, No. 6378, pp. 477-479, 1992.

(Continued)

*Primary Examiner* — Brian McDowell
(74) *Attorney, Agent, or Firm* — K & L Gates LLP; Louis C. Cullman; Brent A. Johnson

(57) ABSTRACT

Heteroaryl-aryl compounds such as compounds represented by the Formula:

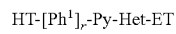

may be used in electronic devices such as organic light-emitting devices. For example, the compounds may be used as an emissive material in an emissive layer.

15 Claims, 1 Drawing Sheet

(56) References Cited

OTHER PUBLICATIONS

H. Riel, S. Karg, T. Beierlein, and W. Rieβ, Tuning the emission characteristics of top-emitting organic light-emitting devices by means of a dielectric capping layer: An experimental and therorectical study; J. Appl. Phys. 94, 5290(2003).

Hiroshi Kanno, Yiru Sun, and Stephen R. Forrest, High-efficiency top-emission white-light-emitting organic electrophosphorescent devices; Appl. Phys. Lett. 86, 263502(2005).

International Search Report and Written Opinion in PCT Application No. PCT/US2012/022792 (NDTC0.202WO), dated May 7, 2012.

International Search Report for PCT/US2013/075584 mailed on Dec. 17, 2013.

Jan Birnstock, Tobias W. Canzler, Michael Holfmann, Giang Huang, and Tilmann Romainczyk, Highly efficient white Top-emission PIN OLEDs for display and lighting application; 2010 SID, 774, SID 10 Digest.

Kreimer-Birnbaum et al., "Modified Porphyrins, Chlorins, Phthalocyanines and Purpurins: Second-Generation Photosensitizers for Photodynamic Therapy", Semin Hematol, 1989, vol. 26, pp. 157-173.

Li et al., "Synthesis and Functional Properties of Strongly Luminescent Diphenylamine End-Capped Oligophenylenes", American Chemical Society, 2004, vol. 69, pp. 921-927.

Peng et al., "5-Aminolevulinic Acid-Based Photodynamic Therapy. Clinical Research and Future Challenges", Cancer, Jun. 15, 1997, vol. 79, No. 12, pp. 2282-2308.

Schwartz, Gregor et al., "Harvesting Triplet Excitons from Fluorescent Blue Emitters in White Organic Light-Emitting Diodes", Advanced Materials, vol. 19, No. 21, pp. 3672-3676 (2007).

U.S. Appl. No. 14/108,605, filed Dec. 17, 2013 First Named Inventor: Ma Liping Assignee: Nitto Denko Corporation.

Yiru Su and Stephen R. Forrest, Enhanced light out-coupling of organic light-emitting devices using embedded low-index grids; *Nature Photonics*, 2008,2, 483-487.

Sun, Gang et al., TD-DFT and LDM studies of the electronic spectrum properties of 2-(2'-pyridyl)benzimidazole derivatives and their related complexes , Journal of Molecular Structure: THEOCHEM (2010), 955(1-3), 7-13.

* cited by examiner

| 35 |
|---|
| 30 |
| 20 |
| 15 |
| 10 |
| 5 |

FIG.1

| LiF(1 nm)/Al (100nm) |
|---|
| TPBI (40nm) |
| BE-2 (5 nm) |
| BE-2:Ir(piq)2acac |
| BE-2 (5nm) |
| DTASI (30 nm) |
| PEDOT (30 nm) |
| ITO (55 nm) |

FIG.2

ORGANIC LIGHT EMITTING HOST MATERIALS

CROSS REFERENCE TO RELATED APPLICATIONS

The present application claims the benefit of U.S. Provisional Patent Application Ser. No. 61/735,488 filed Dec. 10, 2012, the entire contents of which is hereby incorporated by reference in its entirety.

BACKGROUND

1. Field

The embodiments relate to emissive compounds for light-emitting layers in devices.

2. Description of the Related Art

Organic light-emitting devices (OLED) are becoming increasingly important in lighting and display applications. OLEDs may include an emissive or light-emitting layer that includes a host material and an emissive component dispersed within the host material. Emissive materials of OLED devices may have problems with low stability. This potential deficiency with emissive materials may contribute to low efficiency and short lifetime of the devices comprising the emissive materials.

SUMMARY

Some embodiments include an emissive compound of formula:

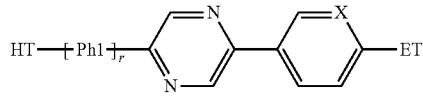

Formula 1 wherein, HT is optionally substituted diphenylamine or optionally substituted phenyl(naphthyl)amine, wherein Ph1 is a p-phenylene, wherein ET is optionally substituted benzimidazol-2-yl, optionally substituted benzoxazol-2-yl, or optionally substituted benzthiazol-2-yl, wherein X is CH or N, and wherein r is 1, 2, 3.

With respect to Formula 1, in some embodiments, HT is unsubstituted diphenylamine, a mono-substituted diphenylamine, a di-substituted diphenylamine, an unsubstituted phenyl(naphthyl)amine, a mono-substituted phenyl(naphthyl)amine, and/or an unsubstituted carbazolyl. In some embodiments, ET is an unsubstituted benzoimidazol-2-yl.

Some embodiments include a compound represented by Formula 1a:

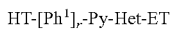        Formula 1a wherein HT is optionally substituted diphenylamine or optionally substituted phenyl(naphthyl)amine; each $Ph^1$ is independently optionally substituted p-phenylene, wherein the p-phenylene directly bonded to HT may optionally form a bond to a phenyl of HT to form a three ring system; Py is optionally substituted pyrazin-2,5-ylene; Het is optionally substituted p-phenylene or optionally substituted pyridin-2,5-ylene; ET is optionally substituted benzimidazol-2-yl, optionally substituted benzoxazol-2-yl, or optionally substituted benzothiazol-2-yl; and r is 1, 2, or 3.

Some embodiments include a compound represented by Formula 2:

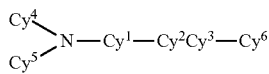        Formula 2 wherein $Cy^1$ is a p-phenylene optionally substituted with 1 or 2 substituents independently selected from $C_{1-6}$ alkyl and F; $Cy^2$ is independently a 2,5-pyridyl optionally substituted with 1, 2, or 3 substituents independently selected from $C_{1-6}$ alkyl and F, or a pyrazine optionally substituted with 1, 2, or 3 substituents independently selected from $C_{1-6}$ alkyl and F; $Cy^3$ is pyridin-2,5-ylene optionally substituted with 1, 2, or 3 substituents independently selected from $C_{1-6}$ alkyl and F, or a p-phenylene optionally substituted with 1 or 2 substituents independently selected from $C_{1-6}$ alkyl and F; $Cy^4$ and $Cy^5$ are independently optionally substituted phenyl or optionally substituted naphthyl, wherein $Cy^4$ and $Cy^5$ may be joined to form, with the nitrogen atom to which they are attached, a carbazolyl ring system; and $Cy^6$ is 1-phenyl-1H-benzo[d]imidazol-2-yl optionally substituted with 1, 2, 3, 4, or 5 substituents independently selected from $C_{1-6}$ alkyl and F.

With respect to Formula 2, in some embodiments $Cy^1$, and $Cy^2$ are independently p-phenylene optionally substituted with 1 or 2 substituents independently selected from $C_{1-6}$ alkyl and F; $Cy^4$ is phenyl optionally substituted with 1, 2, or 3 substituents independently selected from $C_{1-6}$ alkyl and F; $Cy^5$ is phenyl optionally substituted with 1, 2, or 3 substituents independently selected from $C_{1-6}$ alkyl and F, or a naphth-1-yl or naphth-2-yl optionally substituted with 1, 2, or 3 substituents independently selected from $C_{1-6}$ alkyl and F; and $Cy^6$ is 1-phenyl-1H-benzo[d]imidazol-2-yl optionally substituted with 1, 2, 3, 4, or 5 substituents independently selected from $C_{1-6}$ alkyl and F.

Some embodiments include a compound represented by Formula 3:

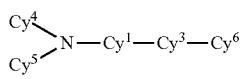        Formula 3 wherein $Cy^1$ is an optionally substituted p-phenylene; $Cy^3$ is selected from an optionally substituted 2,5-pyrazine-3'-pyridine, and optionally substituted 2,5-pyrazine-2',5'-phenyl, an optionally substituted 2,5-bi-pyridinyl, an optionally substituted 3,3'-bi-pyridinyl, and an optionally substituted 3,2':5',3"-terpyridinyl; $Cy^4$ and $Cy^5$ are optionally substituted phenyl or optionally substituted naphthyl; and $Cy^6$ is optionally substituted 1-phenyl-1H-benzo[d]imidazol-2-yl.

With respect to Formula 3, in some embodiments $Cy^1$ is an optionally substituted interphenylene, independently optionally substituted with H, F, methyl, ethyl, propyl, or isopropyl; wherein $Cy^3$ is independently optionally substituted with H, F, methyl, ethyl, propyl, or isopropyl; wherein $Cy^4$ is independently optionally substituted with H, F, methyl, ethyl, propyl, or isopropyl; wherein $Cy^5$ is independently optionally substituted with H, F, methyl, ethyl, propyl, or isopropyl; wherein $Cy^6$ is independently optionally substituted with H, F, methyl, ethyl, propyl, or isopropyl.

Some embodiments include optionally substituted [(para-phenylenyl-para-azolyl)]compounds, including optionally substituted N,N-diphenyl-4-(6-(1-phenyl-1H-benzo[d]imidazol-2-yl)pyridin-3-yl)aniline; N-phenyl-N-(4'-(6-(1-phenyl-1H-benzo[d]imidazol-2-yl)pyridin-3-yl)-[1,1'-biphenyl]-4-yl)naphthalen-1-amine; 4'-(6'-(1-phenyl-1H-benzo[d]imidazol-2-yl)-[3,3'-bipyridin]-6-yl)-N,N-di-p-tolyl-[1,1'-biphenyl]-4-amine; 9,9-dimethyl-N,N-diphenyl-7-(6'-(1-phenyl-1H-benzo[d]imidazol-2-yl)-[3,3'-bipyridin]-6-yl)-9H-fluoren-2-amine; N,N-diphenyl-4'-(6'-(1-phenyl-1H-benzo[d]imidazol-2-yl)-[3,3'-bipyridin]-6-yl)-[1,1'- biphenyl]-4-amine; 4-methyl-N-(4-(6'-(1-phenyl-1H-benzo[d]imidazol-2-yl)-[3,3'-bipyridin]-6-yl)phenyl)-N-(p-tolyl)aniline; N-phenyl-N-(4-(6'-(1-phenyl-1H-benzo[d]imidazol-2-yl)-[3,3'-bipyridin]-6-yl)phenyl)naphthalen-1-amine; 9,9-dimethyl-7-(6'-(1-phenyl-1H-benzo[d]imidazol-2-yl)-[3,3'-bipyridin]-6-yl)-N,N-di-p-tolyl-9H-fluoren-2-amine; N,N-diphenyl-4'-(6'-(1-phenyl-1H-benzo[d]imidazol-2-yl)-[2,3'-bipyridin]-5-yl)-[1,1'-biphenyl]-4-amine; 4'-(3-methyl-6'-(1-phenyl-1H-benzo[d]imidazol-2-yl)-[2,3'-bipyridin]-5-yl)-N,N-diphenyl-[1,1'-biphenyl]-4-amine, N-phenyl-N-(4'-(6'-(1-phenyl-1H-benzo[d]imidazol-2-yl)-[2,3'-bipyridin]-5-yl)-[1,1'-biphenyl]-4-yl)naphthalen-2-amine; N-phenyl-N-(4'-(6'-(1-phenyl-1H-benzo[d]imidazol-2-yl)-[2,3'-bipyridin]-5-yl)-[1,1'-biphenyl]-4-yl)naphthalen-1-amine; 4-methyl-N-(4-(6'-(1-phenyl-1H-benzo[d]imidazol-2-yl)-[2,3'-bipyridin]-5-yl)phenyl)-N-(p-tolyl)aniline; N,N-diphenyl-4-(6-(1-phenyl-1H-benzo[d]imidazol-2-yl)-[3,2':5',3''-terpyridin]-6''-yl)aniline, etc.

Some embodiments include a light-emitting device comprising a compound described herein.

These and other embodiments are described in more detail herein. These and other embodiments are described in more detail herein.

BRIEF DESCRIPTION OF THE DRAWINGS

FIG. 1 is a schematic drawing of an embodiment of an OLED device comprising a compound disclosed herein.

FIG. 2 is a schematic drawing of an embodiment of an OLED device described in Example 2.

DETAILED DESCRIPTION

Unless otherwise indicated, when a compound or chemical structural feature such as aryl is referred to as being "optionally substituted," it is meant that the feature may have no substituents (i.e. be unsubstituted) or may have one or more substituents. A feature that is "substituted" has one or more substituents. The term "substituent" has the ordinary meaning known to one of ordinary skill in the art. In some embodiments, the substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 200 g/mol, 15 g/mol to 300 g/mol, or 15 g/mol to 500 g/mol. In some embodiments, the substituent comprises: 0-30, 0-20, 0-10, or 0-5 carbon atoms; and 0-30, 0-20, 0-10, or 0-5 heteroatoms independently selected from: N, O, S, Si, F, Cl, Br, or I; provided that the substituent comprises at least one atom selected from: C, N, O, S, Si, F, Cl, Br, or I. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, amino, etc. In some embodiments, two substituents may combine to form a ring.

As used herein the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1\text{-}10}$ linear alkyl, such as methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3\text{-}10}$ branched alkyl, such as $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. heptyl isomers), etc.; $C_{3\text{-}10}$ cycloalkyl, such as $C_3H_5$ (e.g. cyclopropyl), $C_4H_7$ (e.g. cyclobutyl isomers such as cyclobutyl, methylcyclopropyl, etc.), $C_5H_9$ (e.g. cyclopentyl isomers such as cyclopentyl, methylcyclobutyl, dimethylcyclopropyl, etc.) $C_6H_{11}$ (e.g. cyclohexyl isomers), $C_7H_{13}$ (e.g. cycloheptyl isomers), etc.; and the like.

As used herein, the term "alkoxy" includes —O-alkyl, such as —$OCH_3$, —$OC_2H_5$, —$OC_3H_7$ (e.g. propoxy isomers such as isopropoxy, n-propoxy, etc.), —$OC_4H_9$ (e.g. butyoxy isomers), —$OC_5H_{11}$ (e.g. pentoxy isomers), —$OC_6H_{13}$ (e.g. hexoxy isomers), —$OC_7H_{15}$ (e.g. heptoxy isomers), etc.

With respect to an optionally substituted moiety such as optionally substituted alkyl, a phrase such as "optionally substituted $C_{1\text{-}12}$ alkyl" refers to a $C_{1\text{-}12}$ alkyl that may be unsubstituted, or may have 1 or more substituents, and does not limit the number of carbon atoms in any substituent. A phrase such as "$C_{1\text{-}12}$ optionally substituted alkyl" refers to unsubstituted $C_{1\text{-}12}$ alkyl, or substituted alkyl wherein both the alkyl parent and all substituents have from 1-12 carbon atoms. Similar conventions may be applied to other optionally substituted moieties such as aryl and heteroaryl.

Substituents on alkyl may be the same as those described generally above, except that alkyl may not have an alkyl substituent. In some embodiments, substituents on alkyl are independently selected from F, Cl, Br, I, CN, $CO_2H$, —O-alkyl, ester groups, acyl, amine groups, and amide groups, and may have a molecular weight of about 15 to about 100 or about 500.

For convenience, the term "molecular weight" is used with respect to a moiety or part of a molecule to indicate the sum of the atomic masses of the atoms in the moiety or part of a molecule, even though it may not be a complete molecule.

The structures associated with some of the chemical names referred to herein are depicted below. These structures may be unsubstituted, as shown below, or a substituent may independently be in any position normally occupied by a hydrogen atom when the structure is unsubstituted. Unless a point of attachment is indicated by

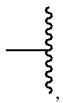

attachment may occur at any position normally occupied by a hydrogen atom.

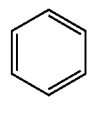 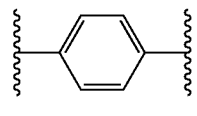 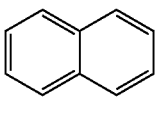

phenyl     p-phenylene     naphthyl

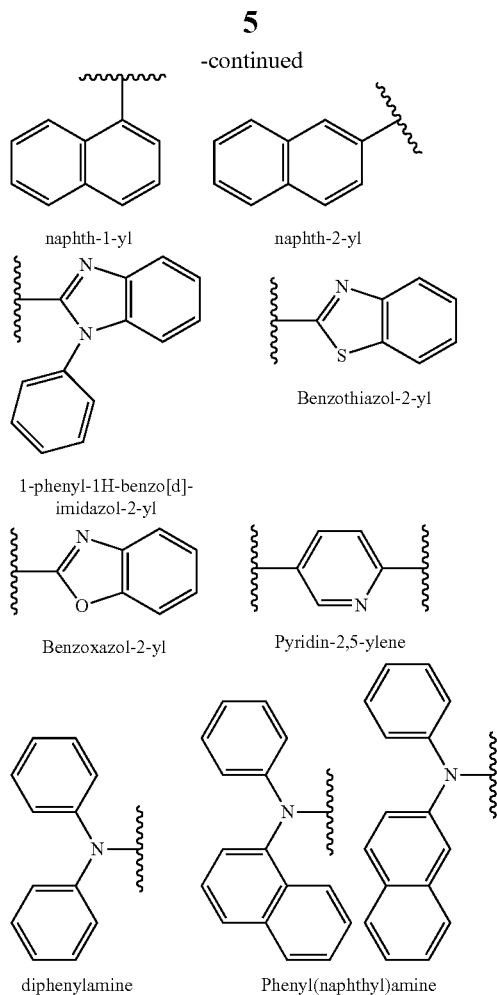
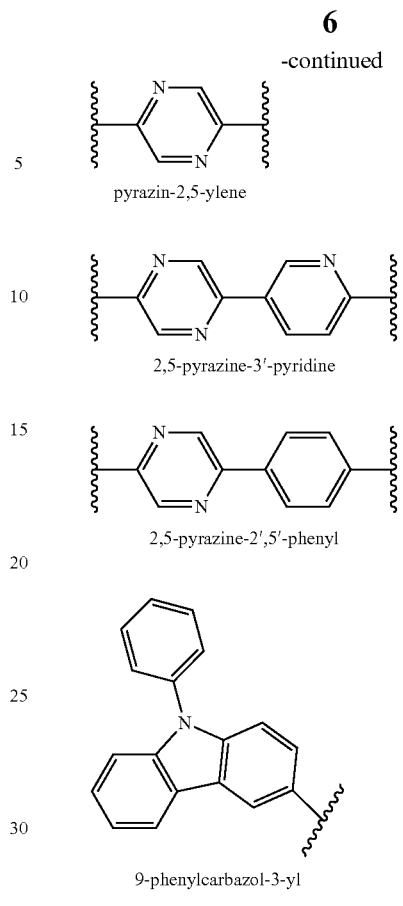
In some embodiments, a compound is provided represented by the following formulae:
Formula 4
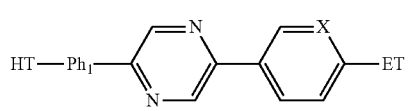
Formula 5
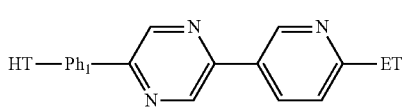
Formula 6
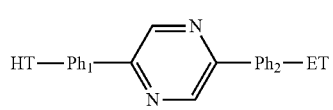
Formula 7
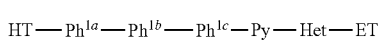
Formula 8
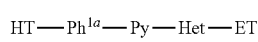
Formula 9
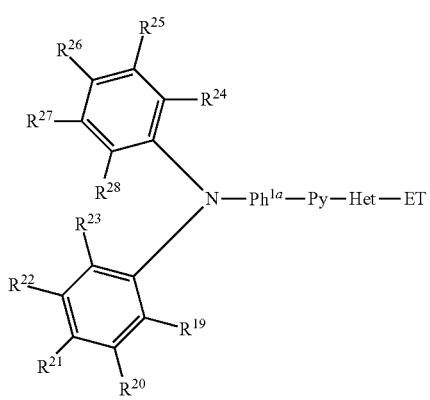

-continued
Formula 10
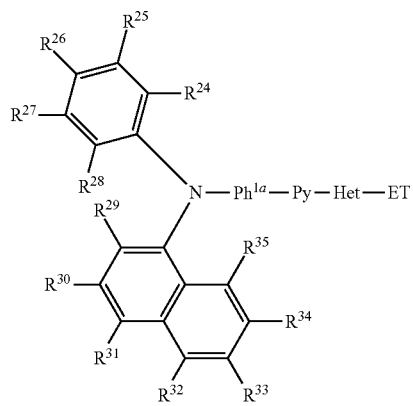
Formula 11
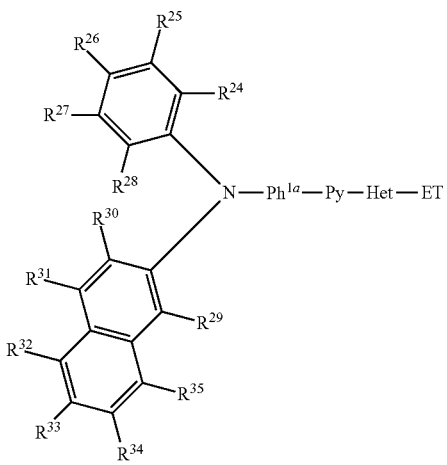
Formula 12
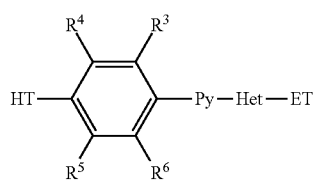
Formula 13
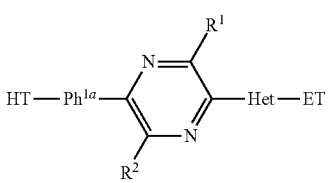
Formula 14
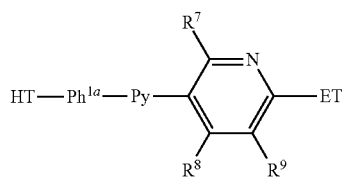
Formula 15
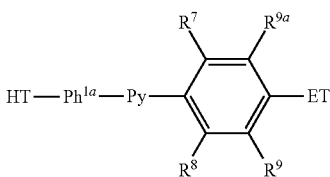
Formula 16
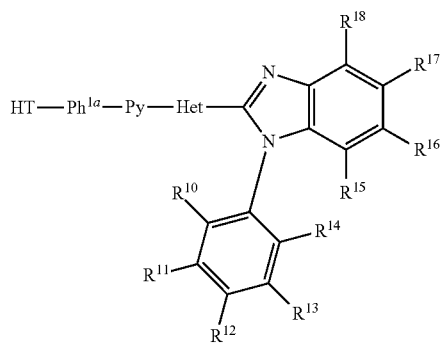
Formula 17
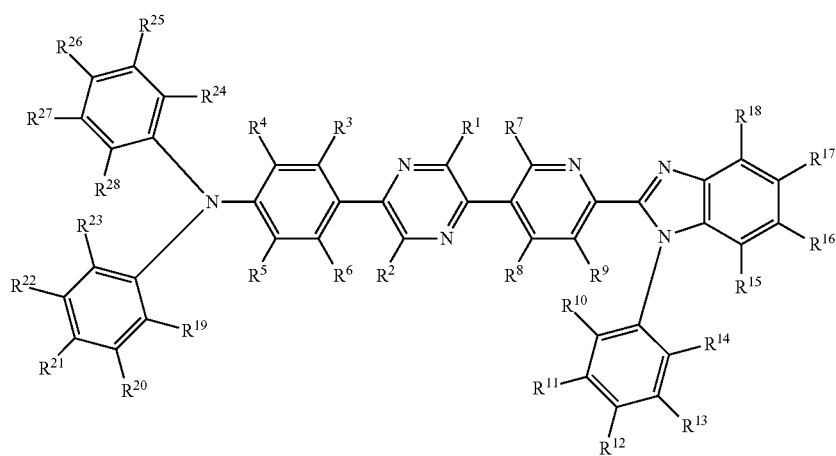

Formula 18
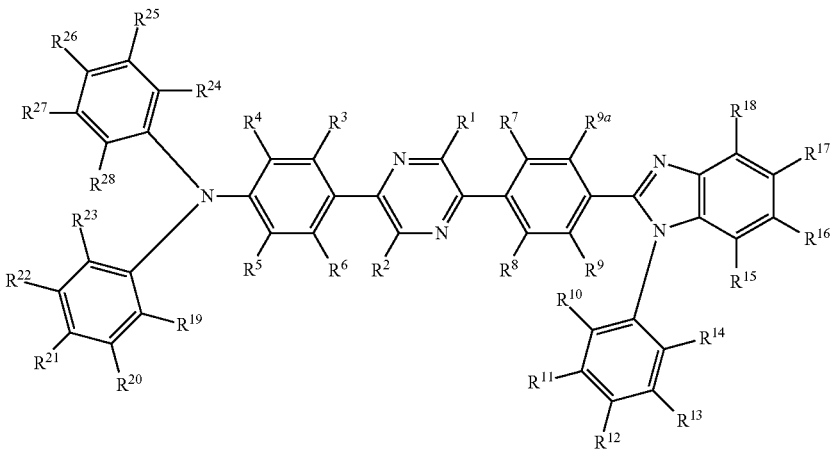
Formula 19
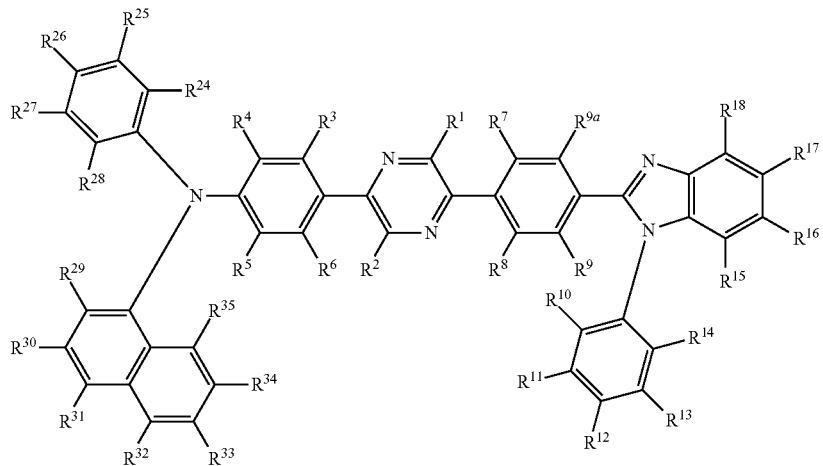
Formula 20
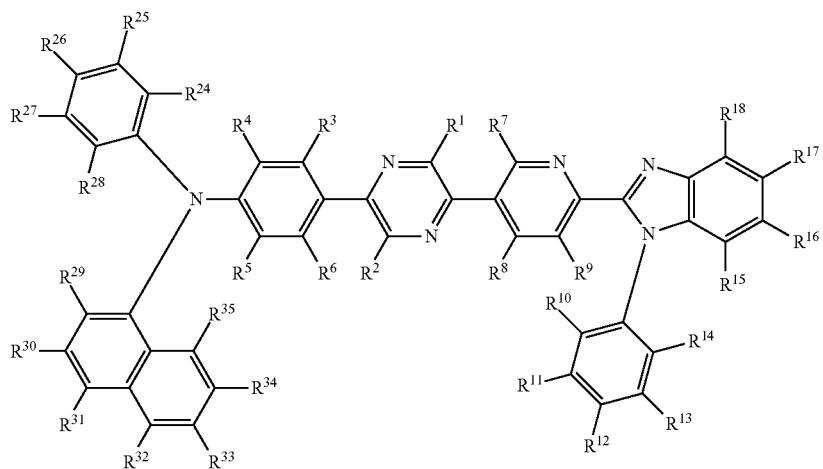

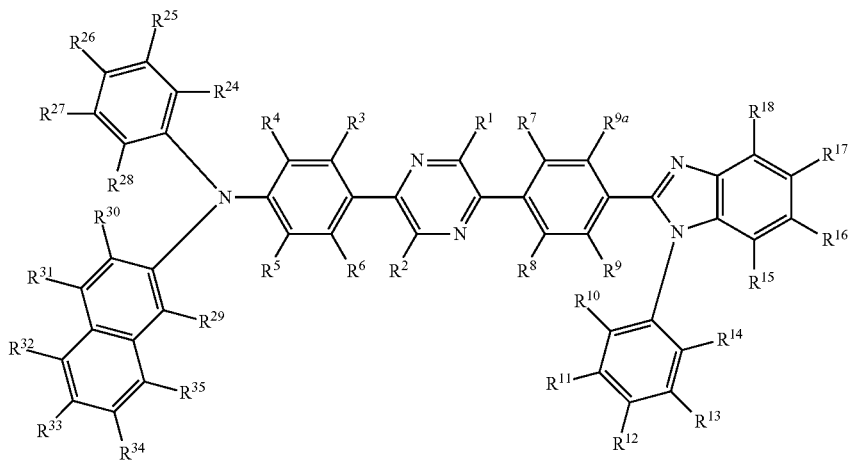

Formula 21

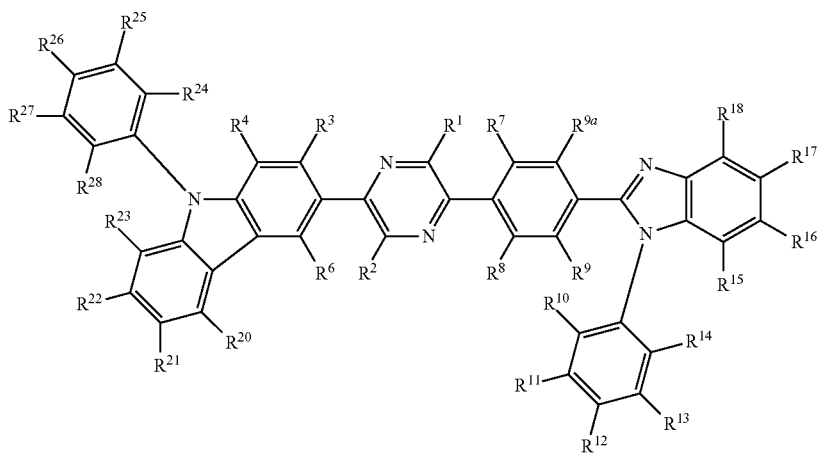

Formula 22

With respect to any relevant formula or structural representation herein, HT may be optionally substituted diphenylamine or optionally substituted phenyl(naphthyl)amine. If the diphenylamine is substituted, it may have 1, 2, 3, 4, 5, 6, 7, 8, 9, or 10 substituents. In some embodiments, the diphenylamine may have 1, 2, 3, or 4 substituents, or 1 or 2 substituents. If the phenyl(naphthyl)amine is substituted, it may have 1, 2, 3, 4, 5, 6, 7, 8, 9, 10, 11, or 12 substituents. In some embodiments, the phenyl(naphthyl)amine may have 1, 2, 3, or 4 substituents, or 1 or 2 substituents. In some embodiments, some or all of the substituents on HT may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as $-O_2CCH_3$, $-CO_2CH_3$, $-O_2CC_2H_5$, $-CO_2C_2H_5$, $-O_2C$-phenyl, $-CO_2$-phenyl, etc.; a $C_{1-10}$ ketone such as $-COCH_3$, $-COC_2H_5$, $-COC_3H_7$, $-CO$-phenyl, etc.; or $C_{1-10}$ amino such as $NH_2$, $NH(CH_3)$, $N(CH_3)_2$, $N(CH_3)C_2H_5$, etc. In some embodiments, any substituents on HT can be an electron donating substituent, such as $C_{1-3}$ alkyl, $C_{1-3}$ —O-alkyl, $NH_3$, or $C_{1-3}$ amino. In some embodiments, HT is unsubstituted.

In some embodiments, HT is:

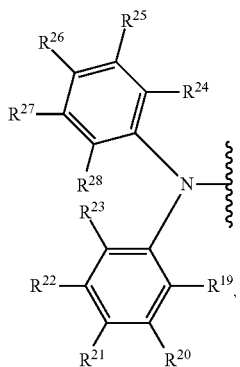

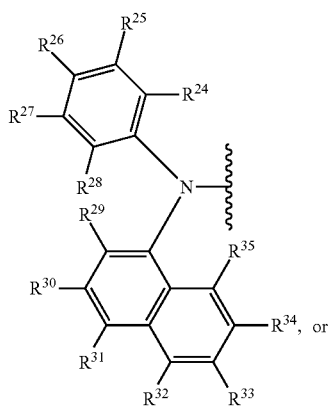

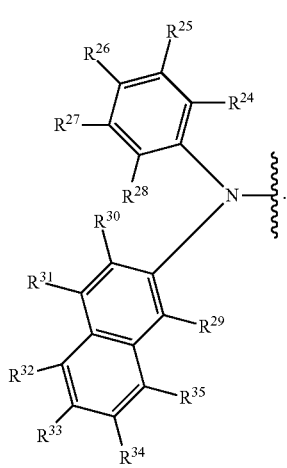

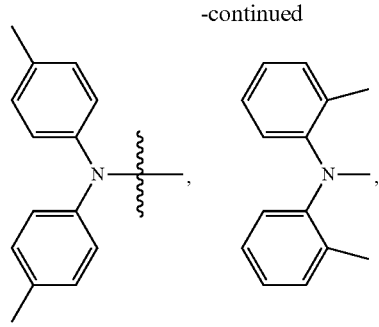

a mono-substituted diphenylamine

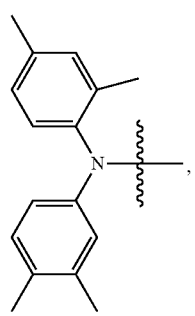

a di-substituted diphenylamine

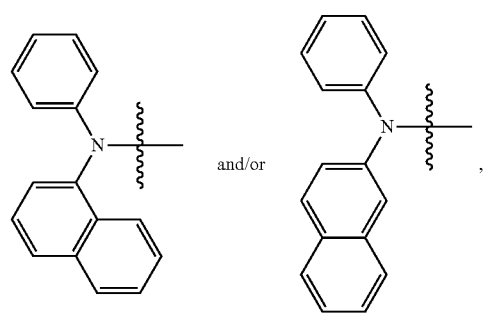

an unsubstituted phenyl(naphthyl)amine

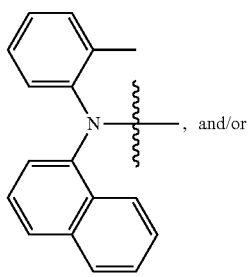

a mono-substituted phenyl(naphthyl)amine

In some embodiments, HT can be selected from optionally substituted carbozolyl, optionally substituted diphenylamine and/or optionally substituted phenyl(naphthyl)amine with 1, 2, 3, 4, 5, 6, 7, 8, 9, 10, 11 or 12 substituents independently selected from $C_{1-6}$ alkyl and F. In some embodiments, HT is selected from unsubstituted diphenylamine, a mono-substituted diphenylamine, a di-substituted diphenylamine, an unsubstituted phenyl(naphthyl)amine, a mono-substituted phenyl(naphthyl)amine, and/or an unsubstituted carbazolyl. Examples of the described ring systems may include any one of the following:

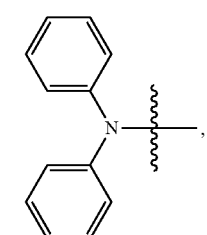

unsubstituted diphenylamine

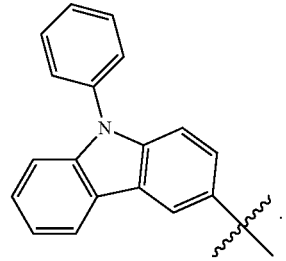

an unsubstituted carbazolyl

In some embodiments, HT is selected any one of

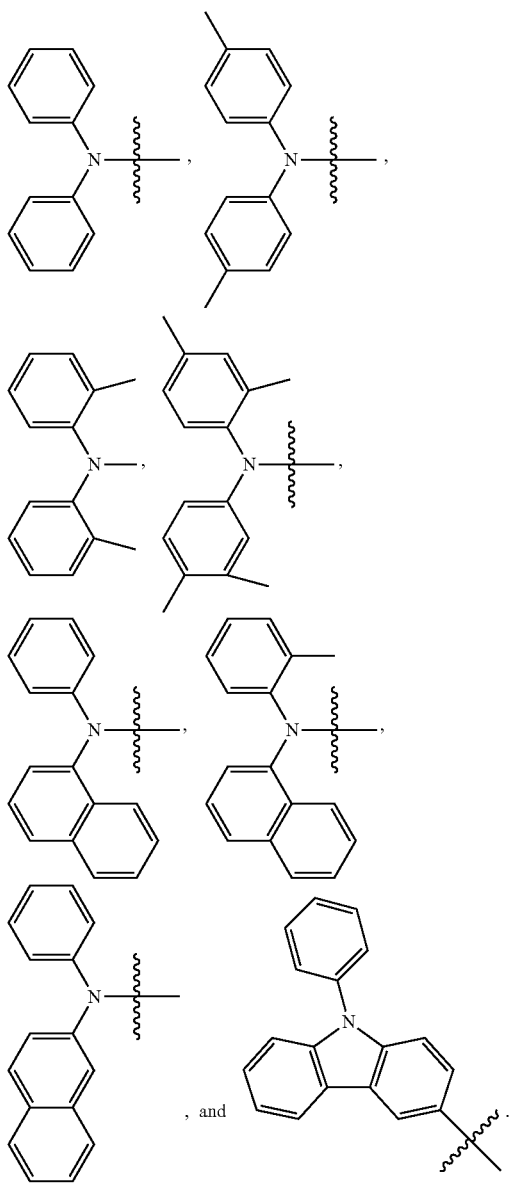

, and

With respect to any relevant formula or structural representation herein, $Ph^{1a}$ may be optionally substituted p-phenylene, or $HT\text{-}Ph^{1a}$ may be 9-phenylcarbazol-3-yl. If the p-phenylene is substituted, it may have 1, 2, 3, or 4 substituents. In some embodiments, the p-phenylene is unsubstituted. In some embodiments the p-phenylene has 1 substituent. In some embodiments, the p-phenylene has 2 substituents. In some embodiments the p-phenylene has 3 substituents. In some embodiments the p-phenylene has 4 substituents. If the 9-phenylcarbazol-3-yl is substituted, it may have it may have 1, 2, 3, 4, 5, 6, 7, 8, 9, 10, or 11, or 12 substituents. In some embodiments, the 9-phenylcarbazol-3-yl may have 1, 2, 3, or 4 substituents, or 1 or 2 substituents. In some embodiments, some or all of the substituents on $Ph^{1a}$ or $HT\text{-}Ph^{1a}$ may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be $C_{1\text{-}10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1\text{-}10}$ optionally substituted alkoxy; halo, such as F, Cl, Br, I; OH; CN; $NO_2$; $C_{1\text{-}6}$ fluoroalkyl, such as $CF_3$, $CF_2H$, $C_2F_5$, etc.; a $C_{1\text{-}10}$ ester such as $-O_2CCH_3$, $-CO_2CH_3$, $-O_2CC_2H_5$, $-CO_2C_2H_5$, $-O_2C$-phenyl, $-CO_2$-phenyl, etc.; a $C_{1\text{-}10}$ ketone such as $-COCH_3$, $-COC_2H_5$, $-COC_3H_7$, $-CO$-phenyl, etc.; or $C_{1\text{-}10}$ amino such as $NH_2$, $NH(CH_3)$, $N(CH_3)_2$, $N(CH_3)C_2H_5$, etc. In some embodiments, any substituents on $Ph^{1a}$ or $HT\text{-}Ph^{1a}$ can be $C_{1\text{-}3}$ alkyl, $C_{1\text{-}3}$ —O-alkyl, $NH_3$, or $C_{1\text{-}3}$ amino. In some embodiments, $Ph^{1a}$ or $HT\text{-}Ph^{1a}$ is unsubstituted.

In some embodiments, $Ph^{1a}$ is:

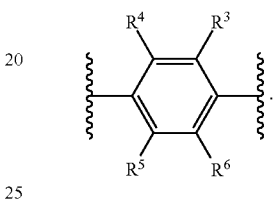

In some embodiments, $HT\text{-}Ph^{1a}$ is:

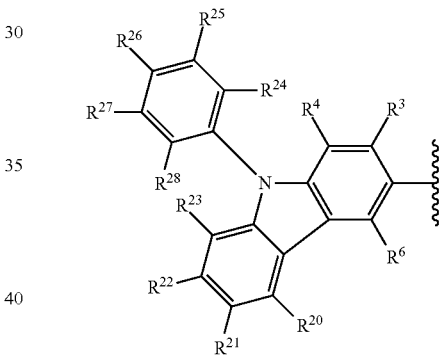

With respect to any relevant formula or structural representation herein, $Ph^{1b}$ may be a bond or optionally substituted p-phenylene. If the p-phenylene is substituted, it may have 1, 2, 3, or 4 substituents. In some embodiments, the p-phenylene is unsubstituted. In some embodiments the p-phenylene has 1 substituent. In some embodiments, the p-phenylene has 2 substituents. In some embodiments the p-phenylene has 3 substituents. In some embodiments the p-phenylene has 4 substituents. In some embodiments, some or all of the substituents on $Ph^{1b}$ may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be $C_{1\text{-}10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1\text{-}10}$ optionally substituted alkoxy; halo, such as F, Cl, Br, I; OH; CN; $NO_2$; $C_{1\text{-}6}$ fluoroalkyl, such as $CF_3$, $CF_2H$, $C_2F_5$, etc.; a $C_{1\text{-}10}$ ester such as $-O_2CCH_3$, $-CO_2CH_3$, $-O_2CC_2H_5$, $-CO_2C_2H_5$, $-O_2C$-phenyl, $-CO_2$-phenyl, etc.; a $C_{1\text{-}10}$ ketone such as $-COCH_3$, $-COC_2H_5$, $-COC_3H_7$, $-CO$-phenyl, etc.; or $C_{1\text{-}10}$ amino such as $NH_2$, $NH(CH_3)$, N(CH$_3$)$_2$, N(CH$_3$)C$_2$H$_5$, etc. In some embodiments, any substituents on Ph$^{1b}$ can be C$_{1-3}$ alkyl, CF$_3$, or F. In some embodiments, Ph$^{1b}$ is a bond.

With respect to any relevant formula or structural representation herein, Ph$^{1c}$ may be a bond or optionally substituted p-phenylene. If the p-phenylene is substituted, it may have 1, 2, 3, or 4 substituents. In some embodiments, the p-phenylene is unsubstituted. In some embodiments the p-phenylene has 1 substituent. In some embodiments, the p-phenylene has 2 substituents. In some embodiments the p-phenylene has 3 substituents. In some embodiments the p-phenylene has 4 substituents. In some embodiments, some or all of the substituents on Ph$^{1c}$ may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be C$_{1-10}$ optionally substituted alkyl, such as CH$_3$, C$_2$H$_5$, C$_3$H$_7$, cyclic C$_3$H$_5$, C$_4$H$_9$, cyclic C$_4$H$_7$, C$_5$H$_{11}$, cyclic C$_5$H$_9$, C$_6$H$_{13}$, cyclic C$_6$H$_{11}$, etc., which may be optionally substituted; C$_{1-10}$ optionally substituted alkoxy; halo, such as F, Cl, Br, I; OH; CN; NO$_2$; C$_{1-6}$ fluoroalkyl, such as CF$_3$, CF$_2$H, C$_2$F$_5$, etc.; a C$_{1-10}$ ester such as —O$_2$CCH$_3$, —CO$_2$CH$_3$, —O$_2$CC$_2$H$_5$, —CO$_2$C$_2$H$_5$, —O$_2$C-phenyl, —CO$_2$-phenyl, etc.; a C$_{1-10}$ ketone such as —COCH$_3$, —COC$_2$H$_5$, —COC$_3$H$_7$, —CO-phenyl, etc.; or C$_{1-10}$ amino such as NH$_2$, NH(CH$_3$), N(CH$_3$)$_2$, N(CH$_3$)C$_2$H$_5$, etc. In some embodiments, any substituents on Ph$^{1c}$ can be C$_{1-3}$ alkyl, CF$_3$, or F. In some embodiments, Ph$^{1c}$ is a bond.

With respect to any relevant formula or structural representation herein, Py may be optionally substituted pyrazin-2,5-ylene. If the pyrazin-2,5-ylene is substituted, it may have 1, 2, 3, or 4 substituents. In some embodiments, the pyrazin-2,5-ylene is unsubstituted. In some embodiments the pyrazin-2,5-ylene has 1 substituent. In some embodiments, the pyrazin-2,5-ylene has 2 substituents. In some embodiments, some or all of the substituents on Py may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be C$_{1-10}$ optionally substituted alkyl, such as CH$_3$, C$_2$H$_5$, C$_3$H$_7$, cyclic C$_3$H$_5$, C$_4$H$_9$, cyclic C$_4$H$_7$, C$_5$H$_{11}$, cyclic C$_5$H$_9$, C$_6$H$_{13}$, cyclic C$_6$H$_{11}$, etc., which may be optionally substituted; C$_{1-10}$ optionally substituted alkoxy; halo, such as F, Cl, Br, I; OH; CN; NO$_2$; C$_{1-6}$ fluoroalkyl, such as CF$_3$, CF$_2$H, C$_2$F$_5$, etc.; a C$_{1-10}$ ester such as —O$_2$CCH$_3$, —CO$_2$CH$_3$, —O$_2$CC$_2$H$_5$, —CO$_2$C$_2$H$_5$, —O$_2$C-phenyl, —CO$_2$-phenyl, etc.; a C$_{1-10}$ ketone such as —COCH$_3$, —COC$_2$H$_5$, —COC$_3$H$_7$, —CO-phenyl, etc.; or C$_{1-10}$ amino such as NH$_2$, NH(CH$_3$), N(CH$_3$)$_2$, N(CH$_3$)C$_2$H$_5$, etc. In some embodiments, any substituents on Py can be C$_{1-3}$ alkyl, CF$_3$, or F. In some embodiments, Py is unsubstituted.

In some embodiments, Py is:

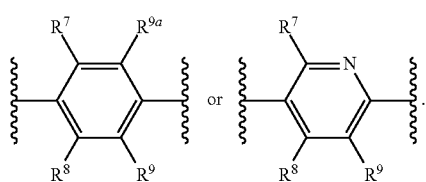

With respect to any relevant formula or structural representation herein, Het may be optionally substituted p-phenylene or optionally substituted pyridin-2,5-ylene. If the p-phenylene is substituted, it may have 1, 2, 3, or 4 substituents. In some embodiments, the p-phenylene is unsubstituted. In some embodiments the p-phenylene has 1 substituent. In some embodiments, the p-phenylene has 2 substituents. In some embodiments the p-phenylene has 3 substituents. In some embodiments the p-phenylene has 4 substituents. If the pyridin-2,5-ylene is substituted, it may have 1, 2, or 3 substituents. In some embodiments, the pyridin-2,5-ylene is unsubstituted. In some embodiments the pyridin-2,5-ylene has 1 substituent. In some embodiments, the pyridin-2,5-ylene has 2 substituents. In some embodiments the pyridin-2,5-ylene has 3 substituents. In some embodiments, some or all of the substituents on Het may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be C$_{1-10}$ optionally substituted alkyl, such as CH$_3$, C$_2$H$_5$, C$_3$H$_7$, cyclic C$_3$H$_5$, C$_4$H$_9$, cyclic C$_4$H$_7$, C$_5$H$_{11}$, cyclic C$_5$H$_9$, C$_6$H$_{13}$, cyclic C$_6$H$_{11}$, etc., which may be optionally substituted; C$_{1-10}$ optionally substituted alkoxy; halo, such as F, Cl, Br, I; OH; CN; NO$_2$; C$_{1-6}$ fluoroalkyl, such as CF$_3$, CF$_2$H, C$_2$F$_5$, etc.; a C$_{1-10}$ ester such as —O$_2$CCH$_3$, —CO$_2$CH$_3$, —O$_2$CC$_2$H$_5$, —CO$_2$C$_2$H$_5$, —O$_2$C-phenyl, —CO$_2$-phenyl, etc.; a C$_{1-10}$ ketone such as —COCH$_3$, —COC$_2$H$_5$, —COC$_3$H$_7$, —CO-phenyl, etc.; or C$_{1-10}$ amino such as NH$_2$, NH(CH$_3$), N(CH$_3$)$_2$, N(CH$_3$)C$_2$H$_5$, etc. In some embodiments, any substituents on Het can be C$_{1-3}$ alkyl, CF$_3$, or F. In some embodiments, Het is unsubstituted.

In some embodiments, Het is:

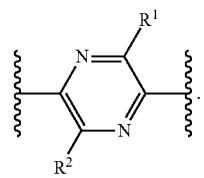

With respect to any relevant formula or structural representation herein, ET may be optionally substituted benzimidazol-2-yl, optionally substituted benzoxazol-2-yl, or optionally substituted benzothiazol-2-yl. If the benzimidazol-2-yl, benzoxazol-2-yl, or benzothiazol-2-yl is substituted, it may have 1, 2, 3, or 4 substituents. In some embodiments, the benzimidazol-2-yl, benzoxazol-2-yl, or benzothiazol-2-yl is unsubstituted. In some embodiments the benzimidazol-2-yl, benzoxazol-2-yl, or benzothiazol-2-yl has 1 substituent. In some embodiments, the benzimidazol-2-yl, benzoxazol-2-yl, or benzothiazol-2-yl has 2 substituents. In some embodiments the benzimidazol-2-yl, benzoxazol-2-yl, or benzothiazol-2-yl has 3 substituents. In some embodiments the benzimidazol-2-yl, benzoxazol-2-yl, or benzothiazol-2-yl has 4 substituents.

In some embodiments, ET is optionally substituted 1-phenyl-1H-benzo[d]imidazol-2-yl. In some embodiments, the 1-phenyl-1H-benzo[d]imidazol-2-yl is unsubstituted. If the 1-phenyl-1H-benzo[d]imidazol-2-yl is substituted, it can have 1, 2, 3, 4, 5, 6, 7, 8, or 9 substituents. In some embodiments, the 1-phenyl-1H-benzo[d]imidazol-2-yl has 1, 2, 3, or 4 substituents. In some embodiments, the 1-phenyl-1H-benzo[d]imidazol-2-yl has 1 or 2 substituents. In some embodiments, some or all of the substituents on ET may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or $C_{1-10}$ amino such as $NH_2$, $NH(CH_3)$, $N(CH_3)_2$, $N(CH_3)C_2H_5$, etc. In some embodiments, any substituents on ET can be $C_{1-3}$ alkyl, or an electron withdrawing substituent such as F, Cl, $NO_2$, CN, COH, $COCH_3$, etc. In some embodiments, ET is unsubstituted.

In some embodiments, ET is:

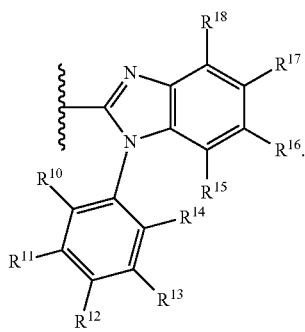

In some embodiments, ET can be selected from optionally substituted benzimidazol-2-yl, optionally substituted benzoxazol-2-yl, and/or optionally substituted benzthiazol-2-yl. In some embodiments, ET is an unsubstituted benzoimidazol-2-yl. In some embodiments, ET is selected from

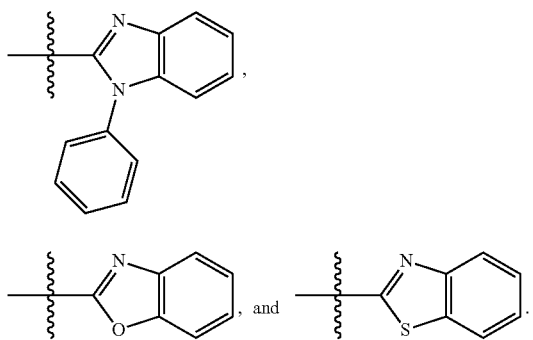

In some embodiments, ET is an optionally substituted benzimidazol-2-yl.

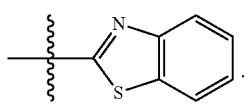 [SMILES: *c1nc2ccccc2s1]

In some embodiments, ET is

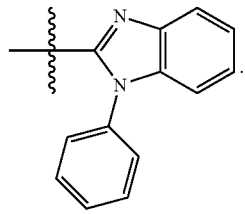 [SMILES: *c1nc2ccccc2n1-c1ccccc1]

With respect to any relevant formula above, $Ph^1$ and/or $Ph^2$ can be an optionally substituted p-phenylene.

With respect to any relevant formula above, X can be selected from C and N, e.g., Formula 3 and/or 2 respectively.

In some embodiments, $Ph^1$ is optionally substituted p-phenylene with 1, 2, 3 or 4 substituents independently selected from $C_{1-6}$ alkyl and F. In some embodiments, $Ph^1$ is an unsubstituted p-phenylene.

In some embodiments, $Ph^2$ is optionally substituted p-phenylene with 1, 2, 3 or 4 substituents independently selected from $C_{1-6}$ alkyl and F. In some embodiments, $Ph^2$ is an unsubstituted p-phenylene.

Generally $R^1$-$R^{35}$, may be H or any substituent, such as a substituent having from 0 to 6 carbon atoms and from 0 to 5 heteroatoms, wherein each heteroatom is independently: O, N, S, F, Cl, Br, or I, and/or having a molecular weight of 15 g/mol to 300 g/mol. Any of $R^1$-$R^{35}$ may comprise: a) 1 or more alkyl moieties optionally substituted with, or optionally connected by or to, b) 1 or more functional groups, such as C=C, C≡C, CO, $CO_2$, CON, $NCO_2$, OH, SH, O, S, N, N=C, F, Cl, Br, I, CN, $NO_2$, $CO_2H$, $NH_2$, etc.; or may be a substituent having no alkyl portion, such as F, Cl, Br, I, $NO_2$, CN, $NH_2$, OH, COH, $CO_2H$, etc.

With respect to any relevant formula or structural depiction herein, some non-limiting examples of $R^1$ may include $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$, etc. In some embodiments, $R^1$ may be may be H; F; Cl; CN; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; $C_{1-6}$ amino, such as —$NHCH_3$, —$NH(CH_3)_2$, —$NHCH_2CH_3$, etc.; $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; CHO; $C_{2-6}$ —CO-alkyl, such as —$COCH_3$, —$COC_2H_5$, —$COC_3H_7$, $COC_4H_9$, —$COC_5H_{11}$, etc.; $CO_2H$; $C_{2-6}$ —$CO_2$-alkyl, —$CO_2CH_3$, —$CO_2C_2H_5$, —$CO_2C_3H_7$, $CO_2C_4H_9$, —$COC_5H_{11}$, etc. In some embodiments, $R^1$ may be H.

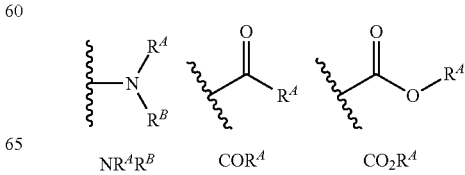

$NR^AR^B$      $COR^A$      $CO_2R^A$

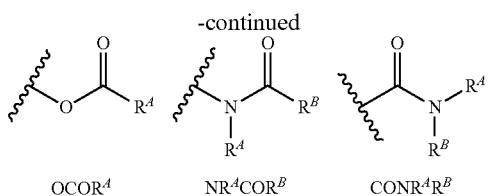

OCOR$^A$     NR$^A$COR$^B$     CONR$^A$R$^B$

Each R$^A$ may independently be H, or C$_{1-12}$ alkyl, including: linear or branched alkyl having a formula C$_a$H$_{a+1}$, or cycloalkyl having a formula C$_a$H$_{a-1}$, wherein a is 1, 2, 3, 4, 5, 6, 7, 8, 9, 10, 11, or 12, such as linear or branched alkyl of a formula: CH$_3$, C$_2$H$_5$, C$_3$H$_7$, C$_4$H$_9$, C$_5$H$_{11}$, C$_6$H$_{13}$, C$_7$H$_{15}$, C$_8$H$_{17}$, C$_9$H$_{19}$, C$_{10}$H$_{21}$, etc., or cycloalkyl of a formula: C$_3$H$_5$, C$_4$H$_7$, C$_5$H$_9$, C$_6$H$_{11}$, C$_7$H$_{13}$, C$_8$H$_{15}$, C$_9$H$_{17}$, C$_{10}$H$_{19}$, etc. In some embodiments, R$^A$ may be H or C$_{1-6}$ alkyl. In some embodiments, R$^A$ may be H or C$_{1-3}$ alkyl. In some embodiments, R$^A$ may be H or CH$_3$. In some embodiments, R$^A$ may be H.

Each R$^B$ may independently be H, or C$_{1-12}$ alkyl, including: linear or branched alkyl having a formula C$_a$H$_{a+1}$, or cycloalkyl having a formula C$_a$H$_a$, wherein a is 1, 2, 3, 4, 5, 6, 7, 8, 9, 10, 11, or 12, such as linear or branched alkyl of a formula: CH$_3$, C$_2$H$_5$, C$_3$H$_7$, C$_4$H$_9$, C$_5$H$_{11}$, C$_6$H$_{13}$, C$_8$H$_{17}$, C$_7$H$_{15}$, C$_9$H$_{19}$, C$_{10}$H$_{21}$, etc., or cycloalkyl of a formula: C$_3$H$_5$, C$_4$H$_7$, C$_5$H$_9$, C$_6$H$_{11}$, C$_7$H$_{13}$, C$_8$H$_{15}$, C$_9$H$_{17}$, C$_{10}$H$_{19}$, etc. In some embodiments, R$^B$ may be H or C$_{1-3}$ alkyl. In some embodiments, R$^B$ may be H or CH$_3$. In some embodiments, R$^B$ may be H.

With respect to any relevant formula or structural depiction herein, some non-limiting examples of R$^2$ may include R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$, etc. In some embodiments, R$^2$ may be H; F; Cl; CN; CF$_3$; OH; NH$_2$; C$_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; C$_{1-6}$ amino, such as —NHCH$_3$, —NH(CH$_3$)2, —NHCH$_2$CH$_3$, etc.; C$_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; CHO; C$_{2-6}$—CO-alkyl, such as —COCH$_3$, —COC$_2$H$_5$, —COC$_3$H$_7$, COC$_4$H$_9$, —COC$_5$H$_{11}$, etc.; CO$_2$H; C$_{2-6}$—CO$_2$-alkyl, —CO$_2$CH$_3$, —CO$_2$C$_2$H$_5$, —CO$_2$C$_3$H$_7$, CO$_2$C$_4$H$_9$, —COC$_5$H$_{11}$, etc. In some embodiments, R$^2$ may be H.

With respect to any relevant formula or structural depiction herein, some non-limiting examples of R$^3$ may include R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$, etc. In some embodiments, R$^3$ may be H; F; Cl; CN; CF$_3$; OH; NH$_2$; C$_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; C$_{1-6}$ amino, such as —NHCH$_3$, —NH(CH$_3$)2, —NHCH$_2$CH$_3$, etc.; C$_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; CHO; C$_{2-6}$—CO-alkyl, such as —COCH$_3$, —COC$_2$H$_5$, —COC$_3$H$_7$, COC$_4$H$_9$, —COC$_5$H$_{11}$, etc.; CO$_2$H; C$_{2-6}$—CO$_2$-alkyl, —CO$_2$CH$_3$, —CO$_2$C$_2$H$_5$, —CO$_2$C$_3$H$_7$, CO$_2$C$_4$H$_9$, —COC$_5$H$_{11}$, etc. In some embodiments, R$^3$ may be H.

With respect to any relevant formula or structural depiction herein, some non-limiting examples of R$^4$ may include R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$, etc. In some embodiments, R$^4$ may be H; F; Cl; CN; CF$_3$; OH; NH$_2$; C$_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; C$_{1-6}$ amino, such as —NHCH$_3$, —NH(CH$_3$)2, —NHCH$_2$CH$_3$, etc.; C$_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; CHO; C$_{2-6}$—CO-alkyl, such as —COCH$_3$, —COC$_2$H$_5$, —COC$_3$H$_7$, COC$_4$H$_9$, —COC$_5$H$_{11}$, etc.; CO$_2$H; C$_{2-6}$—CO$_2$-alkyl, —CO$_2$CH$_3$, —CO$_2$C$_2$H$_5$, —CO$_2$C$_3$H$_7$, CO$_2$C$_4$H$_9$, —COC$_5$H$_{11}$, etc. In some embodiments, R$^4$ may be H.

With respect to any relevant formula or structural depiction herein, some non-limiting examples of R$^5$ may include R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$, etc. In some embodiments, R$^5$ may be H; F; Cl; CN; CF$_3$; OH; NH$_2$; C$_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; C$_{1-6}$ amino, such as —NHCH$_3$, —NH(CH$_3$)2, —NHCH$_2$CH$_3$, etc.; C$_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; CHO; C$_{2-6}$—CO-alkyl, such as —COCH$_3$, —COC$_2$H$_5$, —COC$_3$H$_7$, COC$_4$H$_9$, —COC$_5$H$_{11}$, etc.; CO$_2$H; C$_{2-6}$—CO$_2$-alkyl, —CO$_2$CH$_3$, —CO$_2$C$_2$H$_5$, —CO$_2$C$_3$H$_7$, CO$_2$C$_4$H$_9$, —COC$_5$H$_{11}$, etc. In some embodiments, R$^5$ may be H.

With respect to any relevant formula or structural depiction herein, some non-limiting examples of R$^6$ may include R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$, etc. In some embodiments, R$^6$ may be H; F; Cl; CN; CF$_3$; OH; NH$_2$; C$_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; C$_{1-6}$ amino, such as —NHCH$_3$, —NH(CH$_3$)2, —NHCH$_2$CH$_3$, etc.; C$_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; CHO; C$_{2-6}$—CO-alkyl, such as —COCH$_3$, —COC$_2$H$_5$, —COC$_3$H$_7$, COC$_4$H$_9$, —COC$_5$H$_{11}$, etc.; CO$_2$H; C$_{2-6}$—CO$_2$-alkyl, —CO$_2$CH$_3$, —CO$_2$C$_2$H$_5$, —CO$_2$C$_3$H$_7$, CO$_2$C$_4$H$_9$, —COC$_5$H$_{11}$, etc. In some embodiments, R$^6$ may be H.

With respect to any relevant formula or structural depiction herein, some non-limiting examples of R$^7$ may include R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$, etc. In some embodiments, R$^7$ may be H; F; Cl; CN; CF$_3$; OH; NH$_2$; C$_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; C$_{1-6}$ amino, such as —NHCH$_3$, —NH(CH$_3$)2, —NHCH$_2$CH$_3$, etc.; C$_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; CHO; $C_{2-6}$ —CO-alkyl, such as —COCH$_3$, —COC$_2$H$_5$, —COC$_3$H$_7$, COC$_4$H$_9$, —COC$_5$H$_{11}$, etc.; CO$_2$H; $C_{2-6}$ —CO$_2$-alkyl, —CO$_2$CH$_3$, —CO$_2$C$_2$H$_5$, —CO$_2$C$_3$H$_7$, CO$_2$C$_4$H$_9$, —COC$_5$H$_{11}$, etc. In some embodiments, R$^7$ may be H.

With respect to any relevant formula or structural depiction herein, some non-limiting examples of R$^8$ may include R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$, etc. In some embodiments, R$^8$ may be H; F; Cl; CN; CF$_3$; OH; NH$_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; $C_{1-6}$ amino, such as —NHCH$_3$, —NH(CH$_3$)2, —NHCH$_2$CH$_3$, etc.; $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; CHO; $C_{2-6}$ —CO-alkyl, such as —COCH$_3$, —COC$_2$H$_5$, —COC$_3$H$_7$, COC$_4$H$_9$,—COC$_5$H$_{11}$, etc.; CO$_2$H; $C_{2-6}$ —CO$_2$-alkyl, —CO$_2$CH$_3$, —CO$_2$C$_2$H$_5$, —CO$_2$C$_3$H$_7$, CO$_2$C$_4$H$_6$, —COC$_5$H$_{11}$, etc. In some embodiments, R$^8$ may be H.

With respect to any relevant formula or structural depiction herein, some non-limiting examples of R$^9$ may include R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$, etc. In some embodiments, R$^9$ may be H; F; Cl; CN; CF$_3$; OH; NH$_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; $C_{1-6}$ amino, such as —NHCH$_3$, —NH(CH$_3$)2, —NHCH$_2$CH$_3$, etc.; $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; CHO; $C_{2-6}$—CO-alkyl, such as —COCH$_3$, —COC$_2$H$_5$, —COC$_3$H$_7$, COC$_4$H$_9$,—COC$_5$H$_{11}$, etc.; CO$_2$H; $C_{2-6}$ —CO$_2$-alkyl, —CO$_2$CH$_3$, —CO$_2$C$_2$H$_5$, —CO$_2$C$_3$H$_7$, CO$_2$C$_4$H$_9$, —COC$_5$H$_{11}$, etc. In some embodiments, R$^9$ may be H.

With respect to any relevant formula or structural depiction herein, some non-limiting examples of R$^{9a}$ may include R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$, etc. In some embodiments, R$^{10}$ may be H; F; Cl; CN; CF$_3$; OH; NH$_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; $C_{1-6}$ amino, such as —NHCH$_3$, —NH(CH$_3$)2, —NHCH$_2$CH$_3$, etc.; $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; CHO; $C_{2-6}$—CO-alkyl, such as —COCH$_3$, —COC$_2$H$_5$, —COC$_3$H$_7$, COC$_4$H$_9$,—COC$_5$H$_{11}$, etc.; CO$_2$H; $C_{2-6}$ —CO$_2$-alkyl, —CO$_2$CH$_3$, —CO$_2$C$_2$H$_5$, —CO$_2$C$_3$H$_7$, CO$_2$C$_4$H$_9$, —COC$_5$H$_{11}$, etc. In some embodiments, R$^{10}$ may be H.

With respect to any relevant formula or structural depiction herein, some non-limiting examples of R$^{10}$ may include R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$, etc. In some embodiments, R$^{10}$ may be H; F; Cl; CN; CF$_3$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; CHO; $C_{2-6}$—CO-alkyl, such as —COCH$_3$, —COC$_2$H$_5$, —COC$_3$H$_7$, COC$_4$H$_9$, —COC$_5$H$_{11}$, etc.; CO$_2$H; $C_{2-6}$ —CO$_2$-alkyl, —CO$_2$CH$_3$, —CO$_2$C$_2$H$_5$, —CO$_2$C$_3$H$_7$, CO$_2$C$_4$H$_9$, —COC$_5$H$_{11}$, etc. In some embodiments, R$^{10}$ may be H.

With respect to any relevant formula or structural depiction herein, some non-limiting examples of R$^{11}$ may include R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$, etc. In some embodiments, R$^{11}$ may be H; F; Cl; CN; CF$_3$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; CHO; $C_{2-6}$—CO-alkyl, such as —COCH$_3$, —COC$_2$H$_5$, —COC$_3$H$_7$, COC$_4$H$_9$, —COC$_5$H$_{11}$, etc.; CO$_2$H; $C_{2-6}$ —CO$_2$-alkyl, —CO$_2$CH$_3$, —CO$_2$C$_2$H$_5$, —CO$_2$C$_3$H$_7$, CO$_2$C$_4$H$_9$, —COC$_5$H$_{11}$, etc. In some embodiments, R$^{11}$ may be H.

With respect to any relevant formula or structural depiction herein, some non-limiting examples of R$^{12}$ may include R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$, etc. In some embodiments, R$^{12}$ may be H; F; Cl; CN; CF$_3$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; CHO; $C_{2-6}$ —CO-alkyl, such as —COCH$_3$, —COC$_2$H$_5$, —COC$_3$H$_7$, COC$_4$H$_9$, —COC$_5$H$_{11}$, etc.; CO$_2$H; $C_{2-6}$ —CO$_2$-alkyl, —CO$_2$CH$_3$, —CO$_2$C$_2$H$_5$, —CO$_2$C$_3$H$_7$, CO$_2$C$_4$H$_9$, —COC$_5$H$_{11}$, etc. In some embodiments, R$^{12}$ may be H.

With respect to any relevant formula or structural depiction herein, some non-limiting examples of R$^{13}$ may include R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$, etc. In some embodiments, R$^{13}$ may be H; F; Cl; CN; CF$_3$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; CHO; $C_{2-6}$ —CO-alkyl, such as —COCH$_3$, —COC$_2$H$_5$, —COC$_3$H$_7$, COC$_4$H$_9$, —COC$_5$H$_{11}$, etc.; CO$_2$H; $C_{2-6}$ —CO$_2$-alkyl, —CO$_2$CH$_3$, —CO$_2$C$_2$H$_5$, —CO$_2$C$_3$H$_7$, CO$_2$C$_4$H$_9$, —COC$_5$H$_{11}$, etc. In some embodiments, R$^{13}$ may be H.

With respect to any relevant formula or structural depiction herein, some non-limiting examples of R$^{14}$ may include R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$, etc. In some embodiments, R$^{14}$ may be H; F; Cl; CN; CF$_3$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; CHO; $C_{2-6}$ —CO-alkyl, such as —COCH$_3$, —COC$_2$H$_5$, —COC$_3$H$_7$, COC$_4$H$_9$, —COC$_5$H$_{11}$, etc.; CO$_2$H; $C_{2-6}$ —CO$_2$-alkyl, —CO$_2$CH$_3$, —CO$_2$C$_2$H$_5$, —CO$_2$C$_3$H$_7$, CO$_2$C$_4$H$_9$, —COC$_5$H$_{11}$, etc. In some embodiments, R$^{14}$ may be H.

With respect to any relevant formula or structural depiction herein, some non-limiting examples of R$^{15}$ may include R$^A$, F, Cl, CN, OR$^A$, CF$_3$, NO$_2$, NR$^A$R$^B$, COR$^A$, CO$_2$R$^A$, OCORA, NR$^A$COR$^B$, CONR$^A$R$^B$, etc. In some embodiments, R$^{15}$ may be H; F; Cl; CN; CF$_3$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; CHO; $C_{2-6}$ —CO-alkyl, such as —COCH$_3$, —COC$_2$H$_5$, —COC$_3$H$_7$, COC$_4$H$_9$, —COC$_5$H$_{11}$, etc.; $CO_2H$; $C_{2-6}$ —$CO_2$-alkyl, —$CO_2CH_3$, —$CO_2C_2H_5$, —$CO_2C_3H_7$, $CO_2C_4H_9$, —$COC_5H_{11}$, etc. In some embodiments, $R^{15}$ may be H.

With respect to any relevant formula or structural depiction herein, some non-limiting examples of $R^{16}$ may include $R^A$, F, Cl, CN, $OR^A$, $CF_3$, $NO_2$, $NR^AR^B$, $COR^A$, $CO_2R^A$, $OCORA$, $NR^ACOR^B$, $CONR^AR^B$, etc. In some embodiments, $R^{16}$ may be H; F; Cl; CN; $CF_3$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; CHO; $C_{2-6}$—CO-alkyl, such as —$COCH_3$, —$COC_2H_5$, —$COC_3H_7$, $COC_4H_9$, —$COC_5H_{11}$, etc.; $CO_2H$; $C_{2-6}$ —$CO_2$-alkyl, —$CO_2CH_3$, —$CO_2C_2H_5$, —$CO_2C_3H_7$, $CO_2C_4H_9$, —$COC_5H_{11}$, etc. In some embodiments, $R^{16}$ may be H.

With respect to any relevant formula or structural depiction herein, some non-limiting examples of $R^{17}$ may include $R^A$, F, Cl, CN, $OR^A$, $CF_3$, $NO_2$, $NR^AR^B$, $COR^A$, $CO_2R^A$, $OCORA$, $NR^ACOR^B$, $CONR^AR^B$, etc. In some embodiments, $R^{17}$ may be H; F; Cl; CN; $CF_3$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; CHO; $C_{2-6}$ —CO-alkyl, such as —$COCH_3$, —$COC_2H_5$, —$COC_3H_7$, $COC_4H_9$, —$COC_5H_{11}$, etc.; $CO_2H$; $C_{2-6}$ —$CO_2$-alkyl, —$CO_2CH_3$, —$CO_2C_2H_5$, —$CO_2C_3H_7$, $CO_2C_4H_9$, —$COC_5H_{11}$, etc. In some embodiments, $R^{17}$ may be H.

With respect to any relevant formula or structural depiction herein, some non-limiting examples of $R^{18}$ may include $R^A$, F, Cl, CN, $OR^A$, $CF_3$, $NO_2$, $NR^AR^B$, $COR^A$, $CO_2R^A$, $OCORA$, $NR^ACOR^B$, $CONR^AR^B$, etc. In some embodiments, $R^{18}$ may be H; F; Cl; CN; $CF_3$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; CHO; $C_{2-6}$ —CO-alkyl, such as —$COCH_3$, —$COC_2H_5$, —$COC_3H_7$, $COC_4H_9$, —$COC_5H_{11}$, etc.; $CO_2H$; $C_{2-6}$ —$CO_2$-alkyl, —$CO_2CH_3$, —$CO_2C_2H_5$, —$CO_2C_3H_7$, $CO_2C_4H_9$, —$COC_5H_{11}$, etc. In some embodiments, $R^{18}$ may be H.

With respect to any relevant formula or structural depiction herein, some non-limiting examples of $R^{19}$ may include $R^A$, F, Cl, CN, $OR^A$, $CF_3$, $NO_2$, $NR^AR^B$, $COR^A$, $CO_2R^A$, $OCORA$, $NR^ACOR^B$, $CONR^AR^B$, etc. In some embodiments, $R^{19}$ may be H; F; Cl; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{19}$ may be H. In some embodiments $R^{19}$ is methyl.

With respect to any relevant formula or structural depiction herein, some non-limiting examples of $R^{20}$ may include $R^A$, F, Cl, CN, $OR^A$, $CF_3$, $NO_2$, $NR^AR^B$, $COR^A$, $CO_2R^A$, $OCORA$, $NR^ACOR^B$, $CONR^AR^B$, etc. In some embodiments, $R^{20}$ may be H; F; Cl; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{20}$ may be H.

With respect to any relevant formula or structural depiction herein, some non-limiting examples of $R^{21}$ may include $R^A$, F, Cl, CN, $OR^A$, $CF_3$, $NO_2$, $NR^AR^B$, $COR^A$, $CO_2R^A$, $OCORA$, $NR^ACOR^B$, $CONR^AR^B$, etc. In some embodiments, $R^{21}$ may be H; F; Cl; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{21}$ may be H. In some embodiments $R^{21}$ is methyl.

With respect to any relevant formula or structural depiction herein, some non-limiting examples of $R^{22}$ may include $R^A$, F, Cl, CN, $OR^A$, $CF_3$, $NO_2$, $NR^AR^B$, $COR^A$, $CO_2R^A$, $OCORA$, $NR^ACOR^B$, $CONR^AR^B$, etc. In some embodiments, $R^{22}$ may be H; F; Cl; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{22}$ may be H.

With respect to any relevant formula or structural depiction herein, some non-limiting examples of $R^{23}$ may include $R^A$, F, Cl, CN, $OR^A$, $CF_3$, $NO_2$, $NR^AR^B$, $COR^A$, $CO_2R^A$, $OCORA$, $NR^ACOR^B$, $CONR^AR^B$, etc. In some embodiments, $R^{23}$ may be H; F; Cl; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{23}$ may be H.

With respect to any relevant formula or structural depiction herein, some non-limiting examples of $R^{24}$ may include $R^A$, F, Cl, CN, $OR^A$, $CF_3$, $NO_2$, $NR^AR^B$, $COR^A$, $CO_2R^A$, $OCORA$, $NR^ACOR^B$, $CONR^AR^B$, etc. In some embodiments, $R^{24}$ may be H; F; Cl; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{24}$ may be H. In some embodiments $R^{24}$ is methyl.

In some embodiments, $R_{19}$ and $R_{24}$ are methyl.

With respect to any relevant formula or structural depiction herein, some non-limiting examples of $R^{25}$ may include $R^A$, F, Cl, CN, $OR^A$, $CF_3$, $NO_2$, $NR^AR^B$, $COR^A$, $CO_2R^A$, $OCORA$, $NR^ACOR^B$, $CONR^AR^B$, etc. In some embodiments, $R^{25}$ may be H; F; Cl; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{25}$ may be H.

With respect to any relevant formula or structural depiction herein, some non-limiting examples of $R^{26}$ may include $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$, etc. In some embodiments, $R^{26}$ may be H; F; Cl; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{26}$ may be H. In some embodiments $R^{26}$ is methyl.

In some embodiments, $R_{19}$, $R_{21}$, $R_{24}$, and $R_{26}$ are methyl.

In some embodiments, $R_{21}$ and $R_{26}$ are methyl.

With respect to any relevant formula or structural depiction herein, some non-limiting examples of $R^{27}$ may include $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$, etc. In some embodiments, $R^{27}$ may be H; F; Cl; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{27}$ may be H.

With respect to any relevant formula or structural depiction herein, some non-limiting examples of $R^{28}$ may include $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$, etc. In some embodiments, $R^{28}$ may be H; F; Cl; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{28}$ may be H.

With respect to any relevant formula or structural depiction herein, some non-limiting examples of $R^{29}$ may include $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$, etc. In some embodiments, $R^{29}$ may be H; F; Cl; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{29}$ may be H.

With respect to any relevant formula or structural depiction herein, some non-limiting examples of $R^{30}$ may include $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$, etc. In some embodiments, $R^{30}$ may be H; F; Cl; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{30}$ may be H.

With respect to any relevant formula or structural depiction herein, some non-limiting examples of $R^{31}$ may include $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$, etc. In some embodiments, $R^{31}$ may be H; F; Cl; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{31}$ may be H.

With respect to any relevant formula or structural depiction herein, some non-limiting examples of $R^{32}$ may include $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$, etc. In some embodiments, $R^{32}$ may be H; F; Cl; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{32}$ may be H.

With respect to any relevant formula or structural depiction herein, some non-limiting examples of $R^{33}$ may include $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$, etc. In some embodiments, $R^{33}$ may be H; F; Cl; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{33}$ may be H.

With respect to any relevant formula or structural depiction herein, some non-limiting examples of $R^{34}$ may include $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$, etc. In some embodiments, $R^{34}$ may be H; F; Cl; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{34}$ may be H.

With respect to any relevant formula or structural depiction herein, some non-limiting examples of $R^{35}$ may include $R^A$, F, Cl, CN, $OR^A$, $CF_3$, $NO_2$, $NR^AR^B$, $COR^A$, $CO_2R^A$, OCORA, $NR^ACOR^B$, $CONR^AR^B$, etc. In some embodiments, $R^{35}$ may be H; F; Cl; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{35}$ may be H.

Some embodiments include optionally substituted N,N-diphenyl-4-(5-(6-(1-phenyl-1H-benzo[d]imidazol-2-yl)pyridin-3-yl)pyrazin-2-yl)aniline. In some embodiments, any substituents may independently be $CH_3$, $C_2H_5$, $C_3H_7$, F, or $CF_3$. In some embodiments, the compound is unsubstituted.

Some embodiments include optionally substituted 4-methyl-N-(4-(5-(4-(1-phenyl-1H-benzo[d]imidazol-2-yl)phenyl)pyrazin-2-yl)phenyl)-N-(p-tolyl)aniline. In some embodiments, any substituents may independently be $CH_3$, $C_2H_5$, $C_3H_7$, F, or $CF_3$. In some embodiments, the compound is unsubstituted.

Some embodiments include optionally substituted N-phenyl-N-(4-(5-(6-(1-phenyl-1H-benzo[d]imidazol-2-yl)pyridin-3-yl)pyrazin-2-yl)phenyl)naphthalen-1-amine. In some embodiments, any substituents may independently be $CH_3$, $C_2H_5$, $C_3H_7$, F, or $CF_3$. In some embodiments, the compound is unsubstituted.

Some embodiments include optionally substituted N-phenyl-N-(4-(5-(4-(1-phenyl-1H-benzo[d]imidazol-2-yl)phenyl)pyrazin-2-yl)phenyl)naphthalen-1-amine. In some embodiments, any substituents may independently be $CH_3$, $C_2H_5$, $C_3H_7$, F, or $CF_3$. In some embodiments, the compound is unsubstituted.

Some embodiments include optionally substituted 2-methyl-N-(4-(5-(4-(1-phenyl-1H-benzo[d]imidazol-2-yl)phenyl)pyrazin-2-yl)phenyl)-N-(o-tolyl)aniline. In some embodiments, any substituents may independently be $CH_3$, $C_2H_5$, $C_3H_7$, F, or $CF_3$. In some embodiments, the compound is unsubstituted.

Some embodiments include optionally substituted N-(2,4-dimethylphenyl)-2,4-dimethyl-N-(4-(5-(4-(1-phenyl-1H-benzo[d]imidazol-2-yl)phenyl)pyrazin-2-yl)phenyl)aniline. In some embodiments, any substituents may independently be $CH_3$, $C_2H_5$, $C_3H_7$, F, or $CF_3$. In some embodiments, the compound is unsubstituted.

Some embodiments include optionally substituted N,N-diphenyl-4-(5-(4-(1-phenyl-1H-benzo[d]imidazol-2-yl)phenyl)pyrazin-2-yl)aniline. In some embodiments, any substituents may independently be $CH_3$, $C_2H_5$, $C_3H_7$, F, or $CF_3$. In some embodiments, the compound is unsubstituted.

Some embodiments include optionally substituted N-(4-(5-(4-(1-phenyl-1H-benzo[d]imidazol-2-yl)phenyl)pyrazin-2-yl)phenyl)-N-(o-tolyl)naphthalen-1-amine. In some embodiments, any substituents may independently be $CH_3$, $C_2H_5$, $C_3H_7$, F, or $CF_3$. In some embodiments, the compound is unsubstituted.

Some embodiments include optionally substituted N-phenyl-N-(4-(5-(4-(1-phenyl-1H-benzo[d]imidazol-2-yl)phenyl)pyrazin-2-yl)phenyl)naphthalen-2-amine. In some embodiments, any substituents may independently be $CH_3$, $C_2H_5$, $C_3H_7$, F, or $CF_3$. In some embodiments, the compound is unsubstituted.

Some embodiments include optionally substituted 9-phenyl-3-(5-(4-(1-phenyl-1H-benzo[d]imidazol-2-yl)phenyl)pyrazin-2-yl)-9H-carbazole. In some embodiments, any substituents may independently be $CH_3$, $C_2H_5$, $C_3H_7$, F, or $CF_3$. In some embodiments, the compound is unsubstituted.

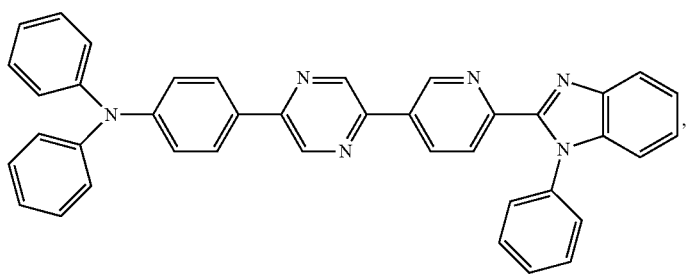

(BE-1)

N,N-diphenyl-4-(5-(6-(1-phenyl-1H-benzo[d]imidazol-2-yl)pyridin-3-yl)pyrazin-2-yl)aniline

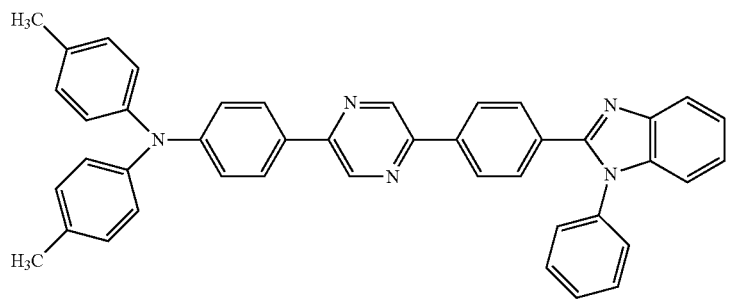

(BE-2)

4-methyl-N-(4-(5-(4-(1-phenyl-1H-benzo[d]imidazol-2-yl)phenyl)pyrazin-2-yl)phenyl)-N-(p-tolyl)aniline (BE-3)
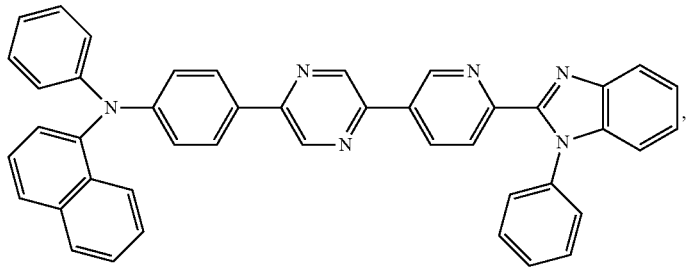
N-phenyl-N-(4-(5-(6-(1-phenyl-1H-benzo[d]imidazol-2-yl)pyridin-3-yl)pyrazine-2-yl)phenyl)naphthalen-1-amine
(BE-4)
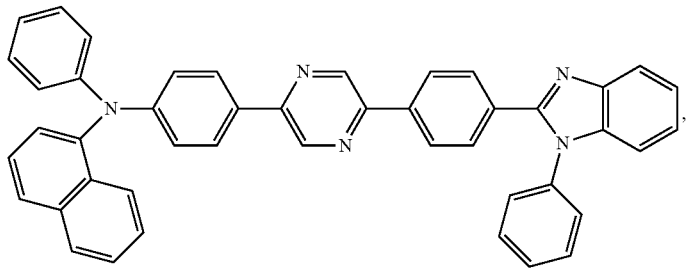
N-phenyl-N-(4-(5-(6-(1-phenyl-1H-benzo[d]imidazol-2-yl)phenyl)pyrazine-2-yl)phenyl)naphthalen-1-amine
(BE-5)
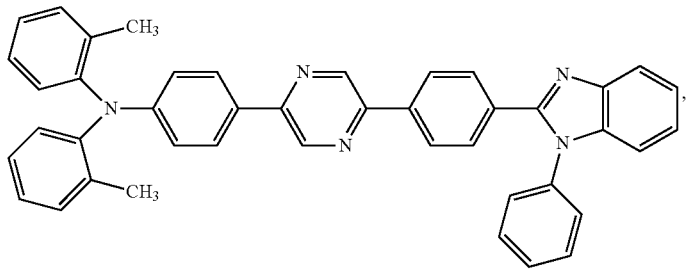
2-methyl-N-(4-(5-(4-(1-phenyl-1H-benzo[d]imidazol-2-yl)phenyl)pyrizin-2-yl)phenyl)-N-(o-tolyl)aniline
(BE-6)
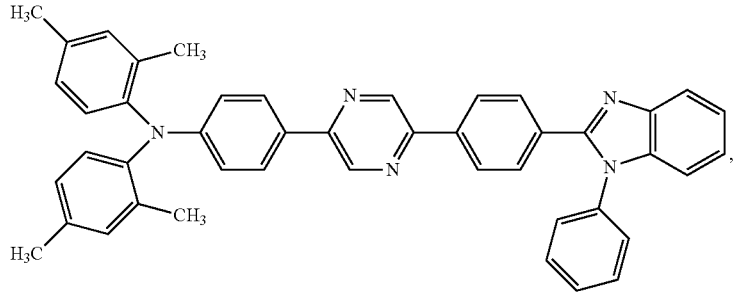
N-(2,4-dimethylphenyl)-2,4-dimethyl-N-(4-(5-(4-(1-phenyl-1H-benzo[d]imidazol-2-yl)phenyl)pyrazin-2-yl)phenyl)aniline

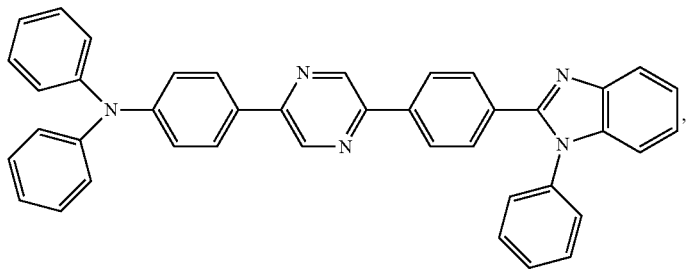

N,N-diphenyl-4-(5-(4-(1-phenyl-1H-benzo[d]imidazol-2-yl)phenyl)pyrazin-2-yl)aniline (BE-7)

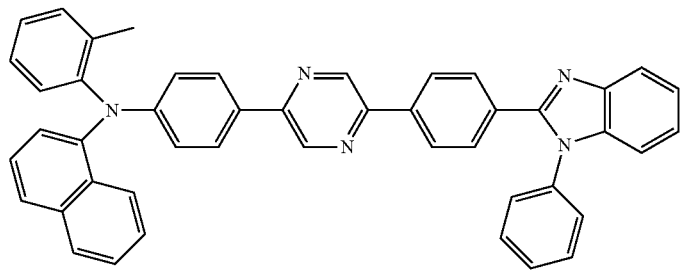

N-(4-(5-(4-(1-phenyl-1H-benzo[d]imidazol-2-yl)phenyl)pyrazin-2-yl)phenyl)-N-(o-tolyl)naphthalen-1-amine (BE-8)

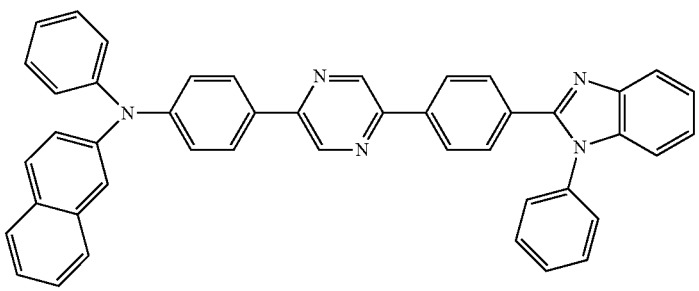

N-phenyl-N-(4-(5-(4-(1-phenyl-1H-benzo[d]imidazol-2-yl)phenyl)pyrazin-2-yl)phenyl)naphthalen-2-amine (BE-9)

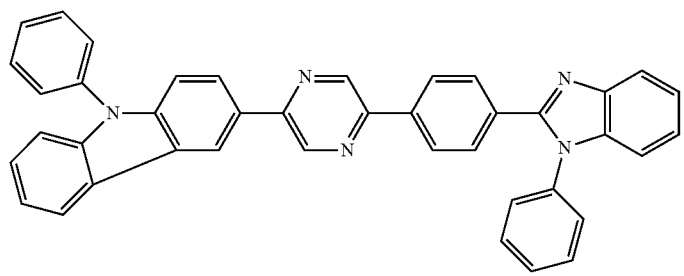

9-phenyl-3-(5-(4-(1-phenyl-1H-benzo[d]imidazol-2-yl)phenyl)pyrazin-2-yl)-9H-carbazole (BE-10)

In some embodiments, a compound of any of the formulae, structures and/or names above (hereinafter referred to as "a subject compound") may be electroluminescent, or may be fluorescent or phosphorescent. In some embodiments, the compound has fluorescence in the blue or violet visible light range or phosphorescence in the red, orange, yellow, and/or green visible light range. In some embodiments, the compound may have a lowest energy triplet state with an energy over than about 2.5 eV, such as about 2.5 eV to about 4 eV, about 2.5 eV to about 3.5 eV, or about 3 eV to about 3.5 eV.

In some embodiments, a light-emitting device is provided, comprising a compound described above.

In some embodiments, a light emitting device is provided, wherein the compound is an emissive material in an emissive layer.

Some embodiments include a composition comprising a subject compound. A composition comprising a subject compound may further comprise a fluorescent compound or a phosphorescent compound, and may be useful for light emission in devices such as organic light-emitting devices.

In some embodiments, an organic light-emitting device comprises a subject compound. For example, an organic component comprising a subject compound may be disposed between an anode and a cathode. The organic component may further comprise an emissive layer, wherein a subject compound is in the emissive layer. In some embodiments, the device is configured so that electrons can be transferred from the cathode to the organic component and holes can be transferred from the anode to the organic component.

The subject compounds may have high photostability and thermal stability in organic light-emitting devices. The subject compounds may also have well balanced hole and electron injection rates and mobilities. This may provide OLED devices with high efficiencies and/or long lifetimes. The subject compounds may also form amorphous solids, which may make the compounds easy to form into films.

Some embodiments may have a structure represented by FIG. 1. A hole-injection layer 10 is disposed on the anode 5. A hole-transport layer 15 is disposed on the hole-injection layer 15. The emissive layer 20 is disposed on the hole-transport layer 15. An electron-transport layer 30 is disposed on the emissive layer 20, and the cathode 35 is disposed on the electron-transport layer 30.

The anode may be a layer comprising a conventional material such as a metal, mixed metal, alloy, metal oxide or mixed-metal oxide, conductive polymer, and/or an inorganic material such as carbon nanotube (CNT). Examples of suitable metals include the Group 1 metals, the metals in Groups 4, 5, 6, and the Group 8-10 transition metals. If the anode layer is to be light-transmitting, metals in Group 10 and 11, such as Au, Pt, and Ag, or alloys thereof; or mixed-metal oxides of Group 12, 13, and 14 metals, such as indium-tin-oxide (ITO), indium-zinc-oxide (IZO), and the like, may be used. In some embodiments, the anode layer may be an organic material such as polyaniline. The use of polyaniline is described in "Flexible light-emitting diodes made from soluble conducting polymer," Nature, vol. 357, pp. 477-479 (11 Jun. 1992). In some embodiments, the anode layer can have a thickness in the range of about 1 nm to about 1000 nm.

A cathode may be a layer including a material having a lower work function than the anode layer. Examples of suitable materials for the cathode layer include alkali metals of Group 1, Group 2 metals, Group 12 metals including rare earth elements, lanthanides and actinides, materials such as aluminum, indium, calcium, barium, samarium and magnesium, and combinations thereof. Li-containing organometallic compounds, LiF, and $Li_2O$ may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In some embodiments, the cathode layer can have a thickness in the range of about 1 nm to about 1000 nm.

In some embodiments, the organic component may comprise at least one light-emitting layer comprising a light-emitting component and a subject compound as a host. The amount of the subject compound in a light-emitting layer may vary. In one embodiment, the amount of a subject compound in a light-emitting layer is in the range of from about 1% to about 99.9% by weight of the light-emitting layer. In another embodiment, the amount of a subject compound in a light-emitting layer is in the range of from about 90% to about 99% by weight of the light-emitting layer. In another embodiment, the amount of a subject compound in a light-emitting layer is about 97% by weight of the light-emitting layer. In some embodiments, the mass of the light-emitting component is about 0.1% to about 10%, about 1% to about 5%, or about 3% of the mass of the light-emitting layer. The light-emitting component may be a fluorescent and/or a phosphorescent compound.

A light-emitting component may comprise an iridium coordination compound such as: bis-{2-[3,5-bis(trifluoromethyl)phenyl]pyridinato-N,C2'}iridium(III)-picolinate; bis(2-[4,6-difluorophenyl]pyridinato-N,C2')iridium (III) picolinate; bis(2-[4,6-difluorophenyl]pyridinato-N,C2')iridium (acetylacetonate); Iridium (III) bis(4,6-difluorophenylpyridinato)-3-(trifluoromethyl)-5-(pyridin-2-yl)-1,2,4-triazolate; Iridium (III) bis(4,6-difluorophenylpyridinato)-5-(pyridin-2-yl)-1H-tetrazolate; bis[2-(4,6-difluorophenyl)pyridinato-N,C$^{2'}$]iridium(III)tetra (1-pyrazolyl)borate; Bis[2-(2'-benzothienyl)-pyridinato-N, C3']iridium (III)(acetylacetonate); Bis[(2-phenylquinolyl)-N,C2']iridium (III) (acetylacetonate); Bis[(1-phenylisoquinolinato-N,C2')]iridium (III) (acetylacetonate); Bis[(dibenzo[f,h]quinoxalino-N,C2']iridium (III)(acetylacetonate); Tris(2,5-bis-2'-(9',9'-dihexylfluorene)pyridine)iridium (III); Tris[1-phenylisoquinolinato-N,C2']iridium (III); Tris-[2-(2'-benzothienyl)-pyridinato-N,C3']iridium (III); Tris[1-thiophen-2-ylisoquinolinato-N,C3']iridium (III); Tris[1-(9,9-dimethyl-9H-fluoren-2-yl)isoquinolinato-(N,C3')iridium (III)); Bis(2-phenylpyridinato-N,C2')iridium(III) (acetylacetonate) [Ir(ppy)$_2$(acac)]; Bis(2-(4-tolyl)pyridinato-N,C2')iridium(III)(acetylacetonate) [Ir(mppy)$_2$(acac)]; Bis (2-(4-tert-butyl)pyridinato-N,C2')iridium (III) (acetylacetonate) [Ir(t-Buppy)$_2$(acac)]; Tris(2-phenylpyridinato-N,C2')iridium (III) [Ir(ppy)$_3$]; Bis(2-phenyloxazolinato-N,C2')iridium (III) (acetylacetonate) [Ir(op)$_2$(acac)]; Tris(2-(4-tolyl)pyridinato-N,C2')iridium(III) [Ir(mppy)$_3$]; Bis[2-phenylbenzothiazolato-N,C2']iridium (III)(acetylacetonate); Bis[2-(4-tert-butylphenyl)benzothiazolato-N,C2']iridium(III)(acetylacetonate); Bis[(2-(2'-thienyl)pyridinato-N,C3')]iridium (III) (acetylacetonate); Tris[2-(9,9-dimethylfluoren-2-yl)pyridinato-(N,C3')]iridium (III); Tris[2-(9,9-dimethylfluoren-2-yl)pyridinato-(N,C3')]iridium (III); Bis[5-trifluoromethyl-2-[3-(N-phenylcarbzolyl) pyridinato-N,C2']iridium(III)(acetylacetonate); (2-Ph-PyCz)$_2$ Ir(III)(acac); etc.

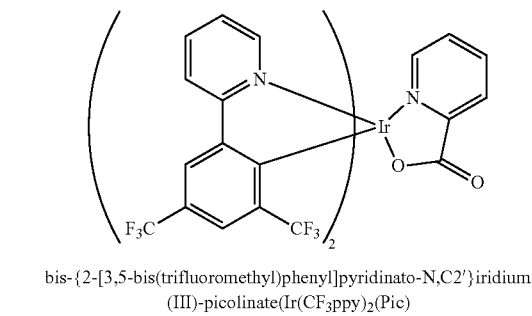

bis-{2-[3,5-bis(trifluoromethyl)phenyl]pyridinato-N,C2'}iridium (III)-picolinate(Ir(CF$_3$ppy)$_2$(Pic)

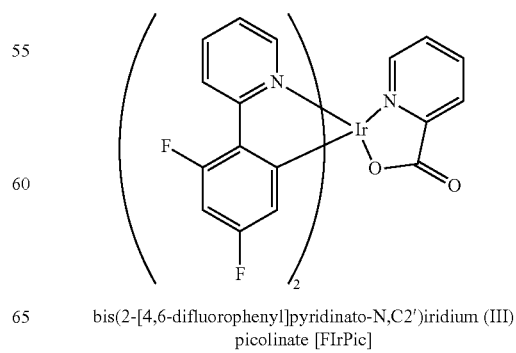

bis(2-[4,6-difluorophenyl]pyridinato-N,C2')iridium (III) picolinate [FIrPic]

-continued

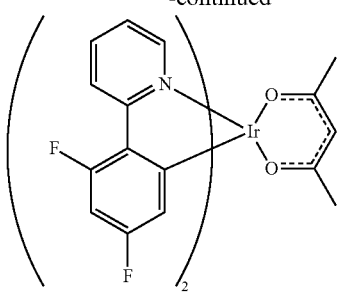

bis(2-[4,6-difluorophenyl]pyridinato-N,C2')iridium
(acetylacetonate)[FIr(acac)]

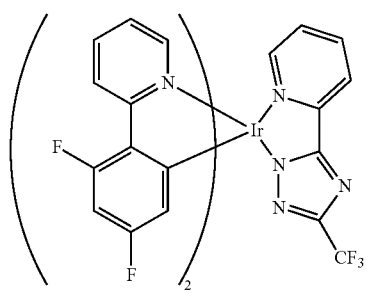

Iridium (III) bis(4,6-difluorophenylpyridinato)-3-
(trifluoromethyl)-5-(pyridin-2-yl)-1,2,4-triazolate (FIrtaz)

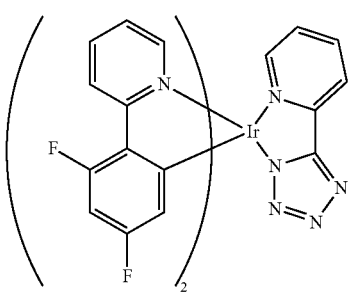

Iridium (III) bis(4,6-difluorophenylpyridinato)-5-
(pyridin-2-yl)-1H-tetrazolate (FIrN4)

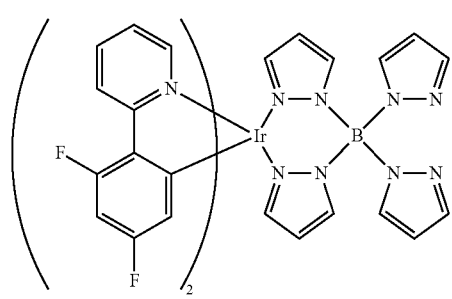

bis[2-(4,6-difluorophenyl)pyridinato-N,C2']iridium (III) tetra
(1-pyrazolyl)borate(Fir6)

-continued

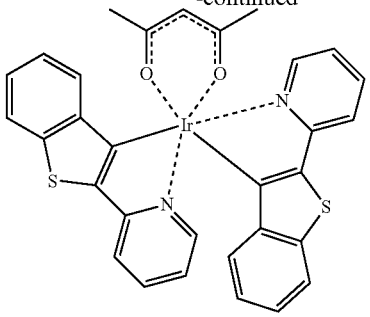

Ir(btp)₂(acac);
(Btp)₂Ir(III)(acac); or
Bis[2-(2'-benzothienyl)-
pyridinato-N,C3'] iridium
(III)(acetylacetonate)

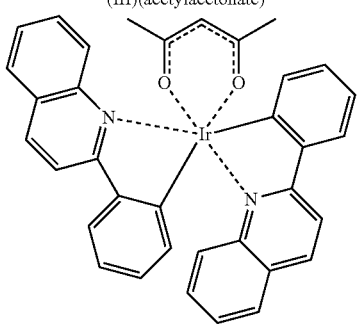

Ir(pq)2(acac);
(Pq)₂Ir(III)(acac); or
Bis[(2-phenylquinolyl)-
N,C2']iridium (III)
(acetylacetonate)

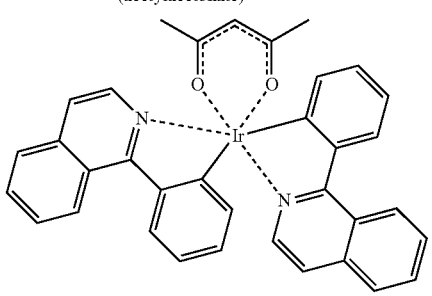

Ir(piq)2(acac);
(Piq)₂Ir(III)(acac); or
Bis[(1-phenylisoquinolinato-
N,C2']iridium (III)
(acetylacetonate)

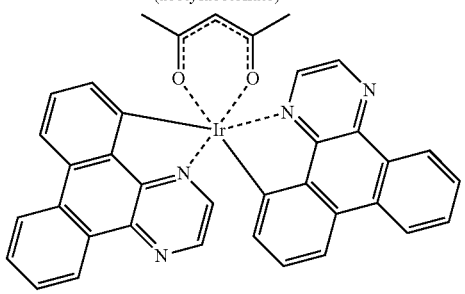

Ir(DBQ)2(acac);
(DBQ)₂Ir(acac); or
Bis[(dibenzo[f,h]quinoxalin-
N,C2')iridium (III) (acetylacetonate)

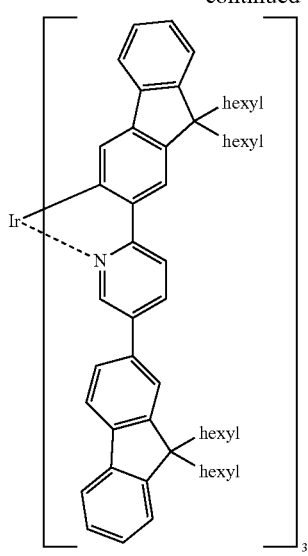
Ir(HFP)₃ or
Tris(2,5-bis-2'-(9',9'-
dihexylfluorene)pyridine)iridium (III)
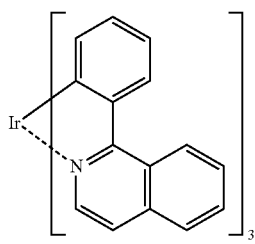
Ir(piq)₃; or
Tris[1-phenylisoquinolinato-
N,C2']iridium (III)
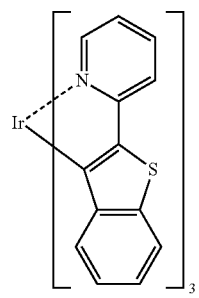
Ir(btp)₃ or
Tris-[2-(2'-benzothienyl)-
pyridinato-N,C3']iridium (III)
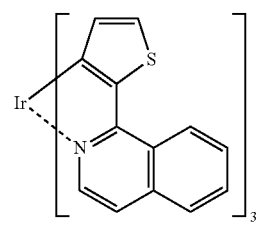
Ir(tiq)₃ or
Tris[1-thiophen-2-
ylisoquinolinato-N,C3']iridium (III)
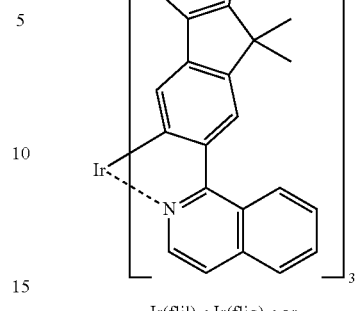
Ir(flil)₃; Ir(fliq)₃; or
Tris[1-(9,9-dimethyl-9H-
fluoren-2-yl)isoquinolinato-
(N,C3')iridium (III))
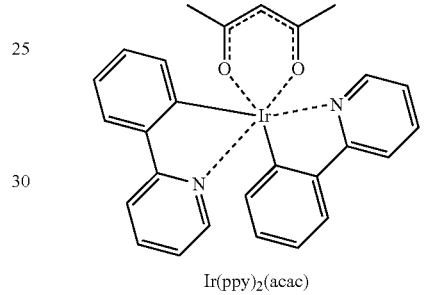
Ir(ppy)₂(acac)
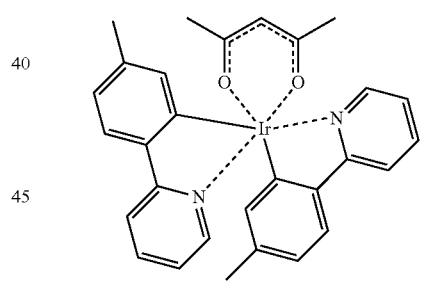
Ir(mppy)₂(acac)
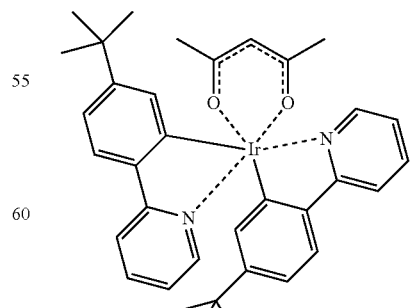 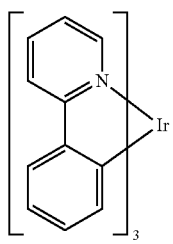
Ir(t-Buppy)₂(acac)   Ir(ppy)₃

-continued

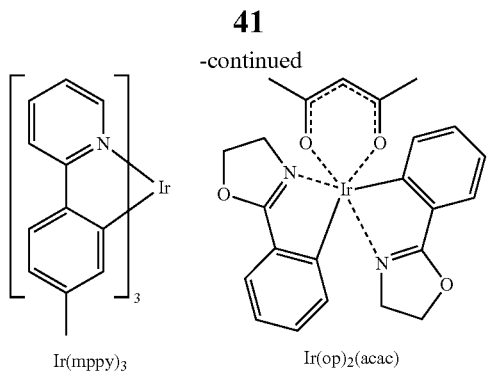

Ir(mppy)₃

Ir(op)₂(acac)

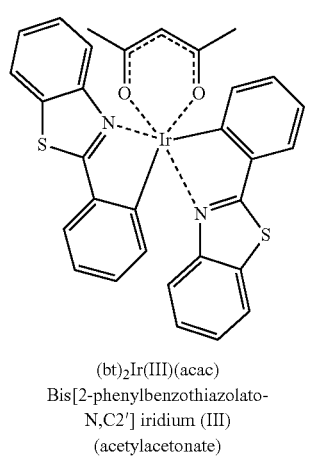

(bt)₂Ir(III)(acac)
Bis[2-phenylbenzothiazolato-
N,C2'] iridium (III)
(acetylacetonate)

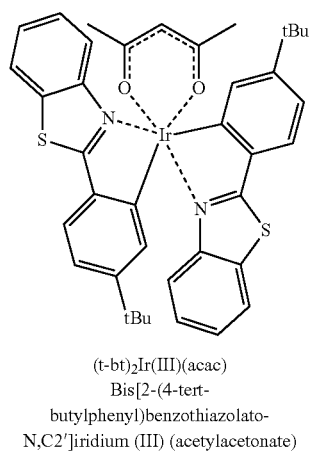

(t-bt)₂Ir(III)(acac)
Bis[2-(4-tert-
butylphenyl)benzothiazolato-
N,C2']iridium (III) (acetylacetonate)

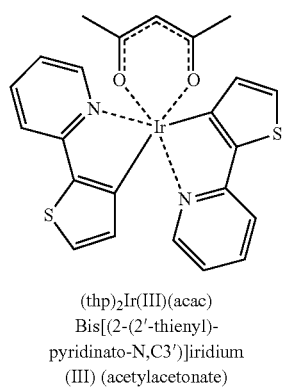

(thp)₂Ir(III)(acac)
Bis[(2-(2'-thienyl)-
pyridinato-N,C3')]iridium
(III) (acetylacetonate)

-continued

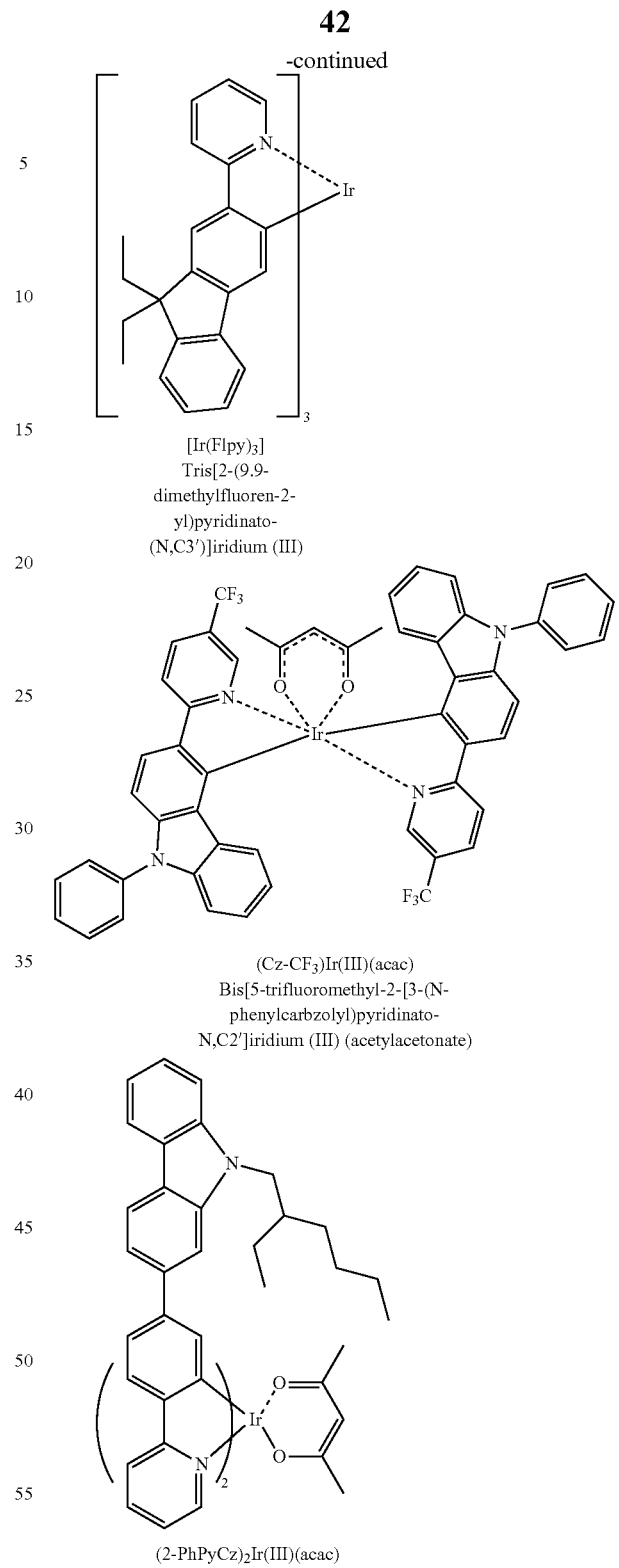

[Ir(Flpy)₃]
Tris[2-(9,9-
dimethylfluoren-2-
yl)pyridinato-
(N,C3')]iridium (III)

(Cz-CF₃)Ir(III)(acac)
Bis[5-trifluoromethyl-2-[3-(N-
phenylcarbzolyl)pyridinato-
N,C2']iridium (III) (acetylacetonate)

(2-PhPyCz)₂Ir(III)(acac)

The thickness of a light-emitting layer may vary. In one embodiment, a light-emitting layer has a thickness in the range of from about 1 nm to about 150 nm or about 200 nm.

In some embodiments, the organic component may further comprise a hole-transport layer disposed between the anode and the light-emitting layer. The hole-transport layer may comprise at least one hole-transport material. Hole-transport materials may include, but are not limited to, an aromatic-substituted amine, a carbazole, a polyvinylcarbazole (PVK), e.g. poly(9-vinylcarbazole); polyfluorene; a polyfluorene copolymer; poly(9,9-di-n-octylfluorene-alt-benzothiadiazole); poly(paraphenylene); poly[2-(5-cyano-5-methylhexyloxy)-1,4-phenylene]; a benzidine; a phenylenediamine; a phthalocyanine metal complex; a polyacetylene; a polythiophene; a triphenylamine; an oxadiazole; copper phthalocyanine; 1,1-Bis(4-bis(4-methylphenyl)aminophenyl)cyclohexane; 2,9-Dimethyl-4,7-diphenyl-1,10-phenanthroline; 3,5-Bis(4-tert-butyl-phenyl)-4-phenyl[1,2,4]triazole; 3,4,5-Triphenyl-1,2,3-triazole; 4,4',4'-tris(3-methylphenylphenylamino)triphenylamine (MTDATA); N,N'-bis(3-methylphenyl)N,N'-diphenyl-[1,1'-biphenyl]-4,4'-diamine (TPD); 4,4'-bis[N-(naphthyl)-N-phenyl-amino]biphenyl (α-NPD); 4,4', 4"-tris(carbazol-9-yl)-triphenylamine (TCTA); 4,4'-bis[N, N'-(3-tolyl)amino]-3,3'-dimethylbiphenyl (HMTPD); 4,4'-N,N'-dicarbazole-biphenyl (CBP); 1,3-N,N-dicarbazolebenzene (mCP); Bis[4-(p,p'-ditolyl-amino)phenyl] diphenylsilane (DTASi); 2,2'-bis(4-carbazolylphenyl)-1,1'-biphenyl (4CzPBP); N,N'N"-1,3,5-tricarbazoloylbenzene (tCP); N,N'-bis(4-butylphenyl)-N,N'-bis(phenyl)benzidine; or the like.

In some embodiments, the organic component may further comprise an electron-transport layer disposed between the cathode and the light-emitting layer. Examples of electron-transport materials may include, but are not limited to, 2-(4-biphenylyl)-5-(4-tert-butylphenyl)-1,3,4-oxadiazole (PBD); 1,3-bis(N,N-t-butyl-phenyl)-1,3,4-oxadiazole (OXD-7), 1,3-bis[2-(2,2'-bipyridine-6-yl)-1,3,4-oxadiazo-5-yl]benzene; 3-phenyl-4-(1'-naphthyl)-5-phenyl-1,2,4-triazole (TAZ); 2,9-dimethyl-4,7-diphenyl-phenanthroline (bathocuproine or BCP); aluminum tris(8-hydroxyquinolate) (Alq3); and 1,3, 5-tris(2-N-phenylbenzimidazolyl)benzene; 1,3-bis[2-(2,2'-bipyridine-6-yl)-1,3,4-oxadiazo-5-yl]benzene (BPY-OXD); 3-phenyl-4-(1'-naphthyl)-5-phenyl-1,2,4-triazole (TAZ), 2,9-dimethyl-4,7-diphenyl-phenanthroline (bathocuproine or BCP); and 1,3,5-tris[2-N-phenylbenzimidazol-z-yl]benzene (TPBI). In one embodiment, the electron transport layer is aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

If desired, additional layers may be included in the light-emitting device. These additional layers may include an electron-injecting layer (EIL), a hole-blocking layer (HBL), an exciton-blocking layer (EBL), and/or a hole-injecting layer (HIL). In addition to separate layers, some of these materials may be combined into a single layer.

In some embodiments, the light-emitting device can include an electron-injecting layer between the cathode layer and the light-emitting layer. Other suitable electron-injecting materials may also be included, and are known to those skilled in the art. Examples of suitable material(s) that can be included in the electron-injecting layer include but are not limited to, an optionally substituted compound selected from the following: aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl] benzene (TPBI) a triazine, a metal chelate of 8-hydroxyquinoline such as tris(8-hydroxyquinoliate)aluminum, and a metal thioxinoid compound such as bis(8-quinolinethiolato) zinc. In one embodiment, the electron-injecting layer is aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

In some embodiments, the device can include a hole-blocking layer, e.g., between the cathode and the light-emitting layer. Various suitable hole-blocking materials that can be included in the hole-blocking layer are known to those skilled in the art. Suitable hole-blocking material(s) include but are not limited to, an optionally substituted compound selected from the following: bathocuproine (BCP), 3,4,5-triphenyl-1, 2,4-triazole, 3,5-bis(4-tert-butyl-phenyl)-4-phenyl-[1,2,4] triazole, 2,9-dimethyl-4,7-diphenyl-1,10-phenanthroline, and 1,1-bis(4-bis(4-methylphenyl)aminophenyl)-cyclohexane.

In some embodiments, the light-emitting device can include an exciton-blocking layer, e.g., between the light-emitting layer and the anode. In an embodiment, the band gap of the material(s) that comprise exciton-blocking layer is large enough to substantially prevent the diffusion of excitons. A number of suitable exciton-blocking materials that can be included in the exciton-blocking layer are known to those skilled in the art. Examples of material(s) that can compose an exciton-blocking layer include an optionally substituted compound selected from the following: aluminum quinolate ($Alq_3$), 4,4'-bis[N-(naphthyl)-N-phenyl-amino]biphenyl (α-NPD), 4,4'-N,N'-dicarbazole-biphenyl (CBP), and bathocuproine (BCP), and any other material(s) that have a large enough band gap to substantially prevent the diffusion of excitons.

In some embodiments, the light-emitting device can include a hole-injecting layer, e.g., between the light-emitting layer and the anode. A hole-injecting layer may comprise a subject compound as a hole-injecting material. Other examples of suitable hole-injecting material(s) include, but are not limited to, an optionally substituted compound selected from the following: a polythiophene derivative such as poly(3,4-ethylenedioxythiophene) (PEDOT)/polystyrene sulphonic acid (PSS), a benzidine derivative such as N,N,N', N'-tetraphenylbenzidine, poly(N,N'-bis(4-butylphenyl)-N, N'-bis(phenyl)benzidine), a triphenyl amine or phenylenediamine derivative such as N,N'-bis(4-methylphenyl)-N,N'-bis (phenyl)-1,4-phenylenediamine, 4,4',4"-tris(N-(naphthylen-2-yl)-N-phenylamino)triphenylamine, an oxadiazole derivative such as 1,3-bis(5-(4-diphenylamino)phenyl-1,3,4-oxadiazol-2-yl)benzene, a polyacetylene derivative such as poly(1,2-bis-benzylthio-acetylene), and a phthalocyanine metal complex derivative such as phthalocyanine copper.

Light-emitting devices comprising a subject compound can be fabricated using techniques known in the art, as informed by the guidance provided herein. For example, a glass substrate can be coated with a high work functioning metal such as ITO which can act as an anode. After patterning the anode layer, a hole-injecting and/or hole-transport layer may be deposited on the anode in that order. A light-emitting layer that includes a light-emitting component, can be deposited on the anode, the hole-transport layer, or the hole-injecting layer. The light-emitting layer may contain a subject compound. An electron-transport layer and/or an electron-injecting layer may deposited in that order on the light-emitting component. The cathode layer, comprising a low work functioning metal (e.g., Mg:Ag), can then be deposited, e.g., by vapor deposition or sputtering. The device may also contain an exciton-blocking layer, an electron blocking layer, a hole blocking layer, a second light-emitting layer, or other layers that can be added to the device using suitable techniques.

In some embodiments, a device comprising the subject compounds can provide a significantly increased device lifetime compared with commercially available compounds. In some embodiments, the devices can provide a T50(h) @ 10000 nit lifetime of at least about 125, 150, 175, 185, and/or 200 hours. In some embodiments, the desired lifetime can be determined by examining the luminescent/emissive decay of the device by measuring the luminescent, e.g., cd/m2, after applying a constant current of a 16 mA to device (corresponding to about 10000 $cd/m^2$) for a device having an active emissive area of about 13.2 $mm^2$.

3. Synthetic Examples

4. Example 1.1

8-1. Example of Synthesis

Synthesis of BE-1

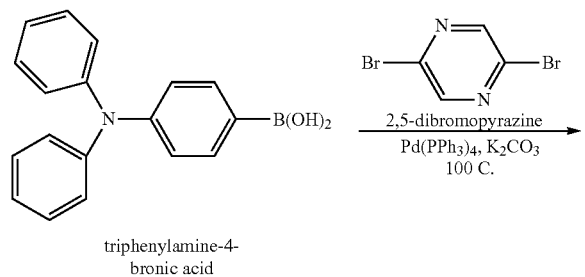

triphenylamine-4-
bronic acid

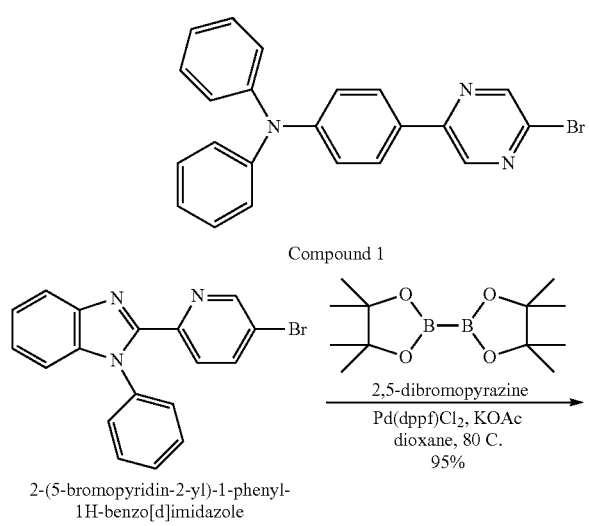

Compound 1

2-(5-bromopyridin-2-yl)-1-phenyl-
1H-benzo[d]imidazole

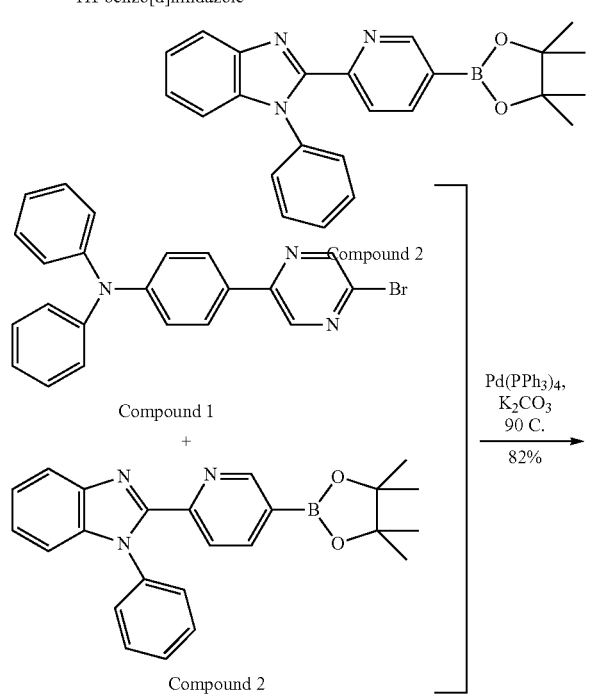

Compound 2

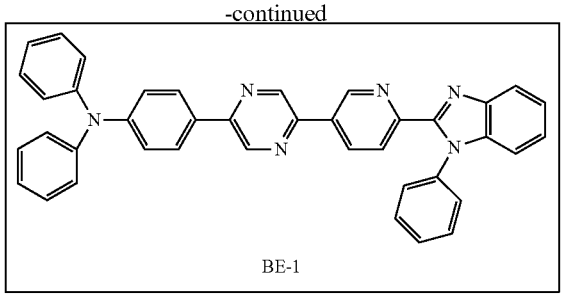

BE-1

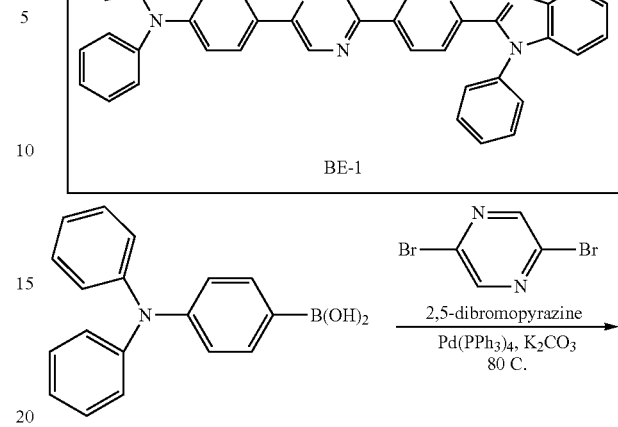

triphenylamine-4-
bronic acid

Compound 1

4-(5-bromopyrazin-2-yl)-N,N-diphenylaniline
(Compound 1)

A mixture of triphenylamine-4-bronic acid (1.0 g, 3.46 mmol), 2,5-dibromopyrazine (1.81 g, 7.6 mmol), Pd(PPh$_3$)$_4$ (0.2 g, 0.17 mmol) and K$_2$CO$_3$ (1.05 g, 7.6 mmol) in dioxane/water (40 mL/8 mL) was degassed and heated at about 80° C. for about 15 hours. The whole was worked up with ethyl acetate (200 mL), washed with brine. The organic phase was dried over Na$_2$SO$_4$, loaded on silica gel, purified by flash column using the eluents of hexanes to hexanes/dichloromethane (2:1 to 1:1 to 1:2). The desired fraction was collected, and removal of solvent gave a yellow solid (Compound 1) (0.99 g, in 71% yield).

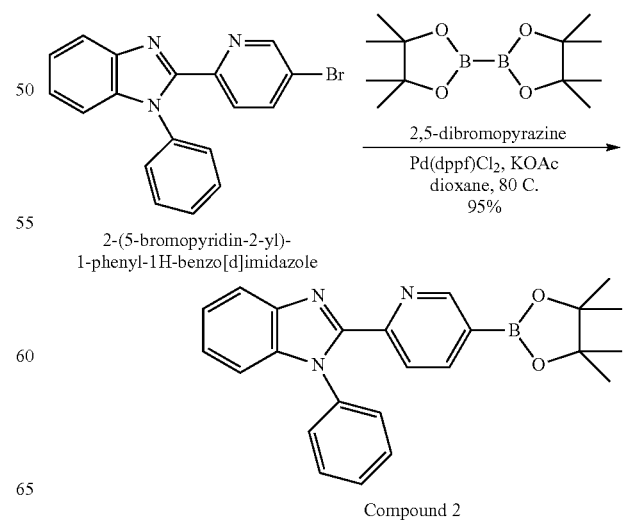

2-(5-bromopyridin-2-yl)-
1-phenyl-1H-benzo[d]imidazole

Compound 2

1-Phenyl-2-(5-(4,4,5,5-tetramethyl-1,3,2-dioxaborolan-2-yl)pyridin-2-yl)-1H-benzo[d]imidazole (Compound 2)

A mixture of 2-(5-bromopyridin-2-yl)-1-phenyl-1H-benzo[d]imidazole (1.015 g, 2.9 mmol), bis(pinacolato)diboron (0.76 g, 3 mmol), KOAc (0.49 g, 5 mmol) and Pd(dppf)Cl2 (0.11 g, 0.15 mmol) in dioxane (50 mL) was degassed and heated at about 80° C. for about 15 hours. The whole was worked up with dichloromethane/brine. The organic phase was collected and dried over Na₂SO₄. After removal of solvent, the resulting brown oil (Compound 2) was used for next step without further purification.

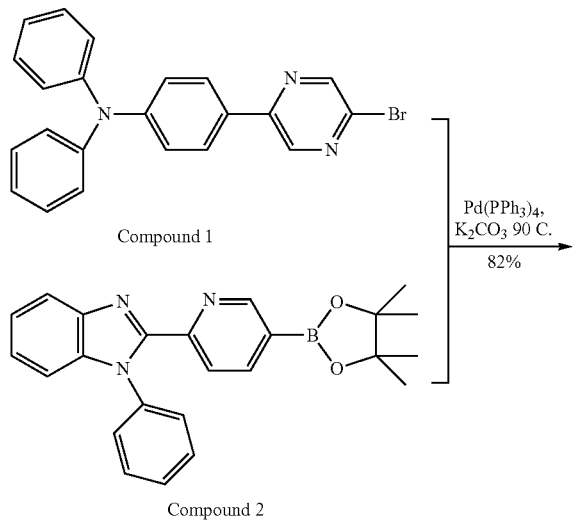

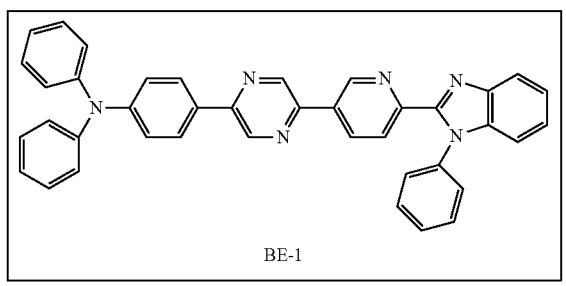

Compound BE-1

A mixture of 4-(5-bromopyrazin-2-yl)-N,N-diphenylaniline (Compound 1) (0.99 g, 2.46 mmol), 1-phenyl-2-(5-(4,4,5,5-tetramethyl-1,3,2-dioxaborolan-2-yl)pyridin-2-yl)-1H-benzo[d]imidazole (Compound 2) (1.15 g, 2.9 mmol), Pd(PPh₃)₄ (0.22 g, 0.19 mmol) and K₂CO₃ (1.0 g, 7.2 mmol) in dioxane/water (60 mL/10 mL), was degassed and heated at about 85° C. overnight. Yellow precipitate formed. After filtration, the solid was collected and washed with methanol, then hot dichloromethane (500 mL). A yellow solid (BE-1) was collected, 1.20 g, in 82% yield. Confirmed by LCMS (APCl+): calcd for $C_{40}H_{29}N_6$ (M+H): 593; found 593.

Synthesis of BE-2

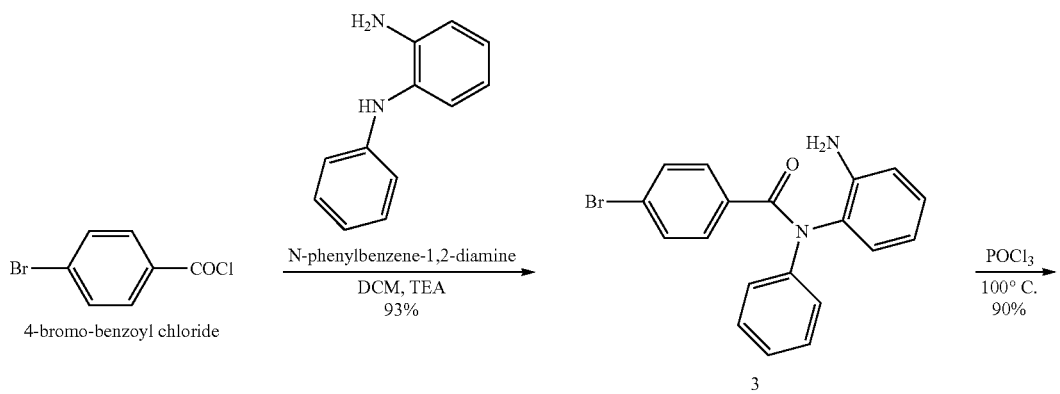

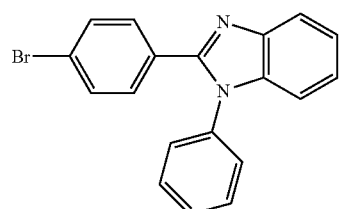

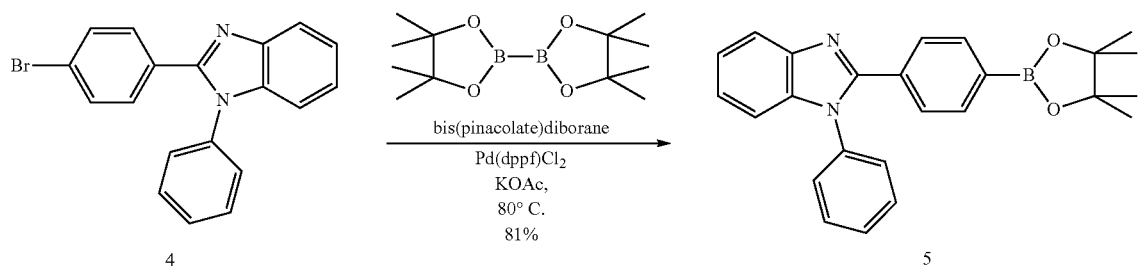
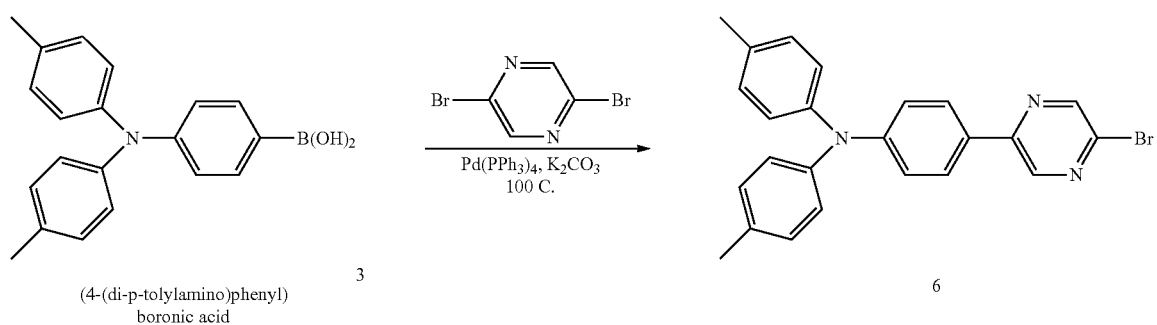
(4-(di-p-tolylamino)phenyl) boronic acid
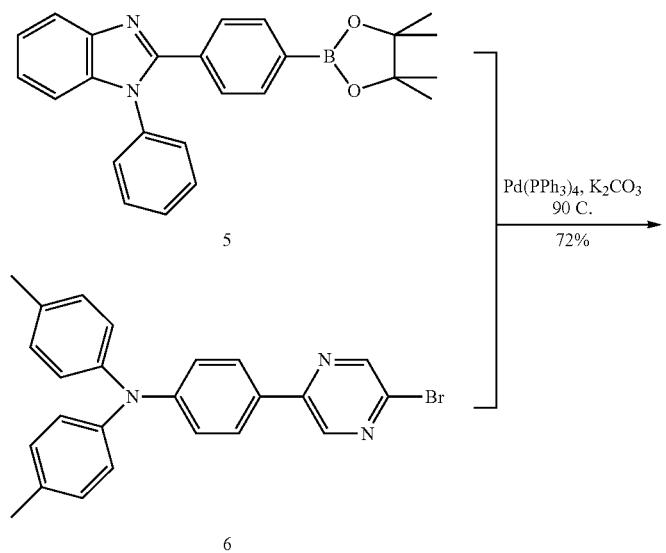
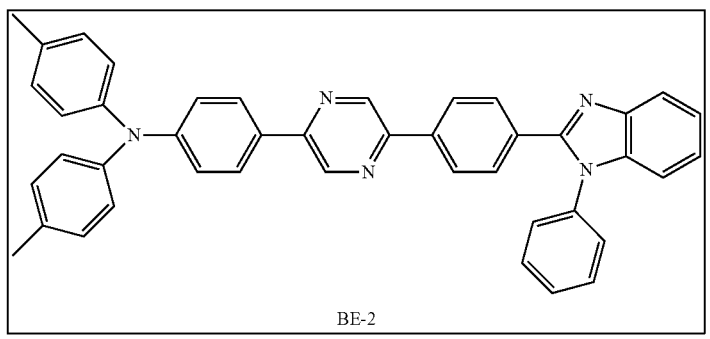
BE-2

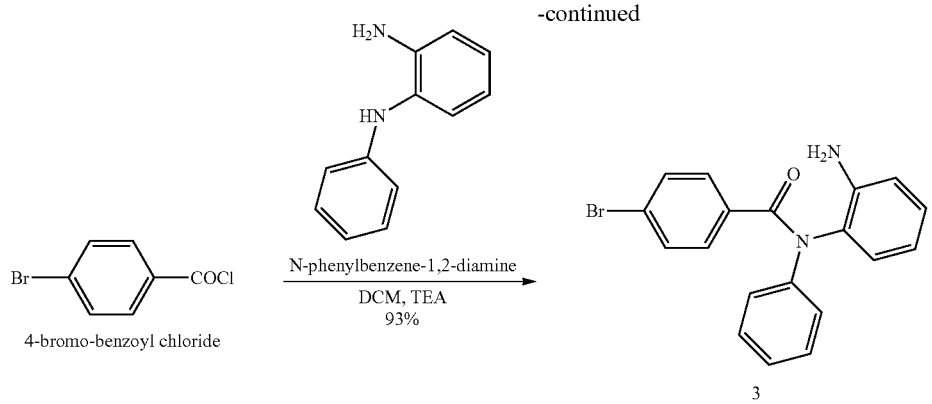

4-Bromo-N-(2-(phenylamino)phenyl)benzamide (Compound 3)

To a solution of 4-bromo-benzoyl chloride (11 g, 50 mmol) in anhydrous dichloromethane (DCM) (100 ml), was added N-phenylbenzene-1,2-diamine (10.2 g, 55 mmol), then triethylamine (TEA) (17 ml, 122 mmol) slowly. The whole was stirred at room temperature (RT) overnight. Filtration gave a white solid 3 (6.5 g). The filtrate was worked up with water (300 ml), then extracted with DCM (300 mL) three times. The organic phase was collected and dried over MgSO$_4$, concentrated and recrystallized in DCM/hexanes to give another portion of white solid 3 (10.6 g). Total amount of product 3 is 17.1 g, in 93% yield.

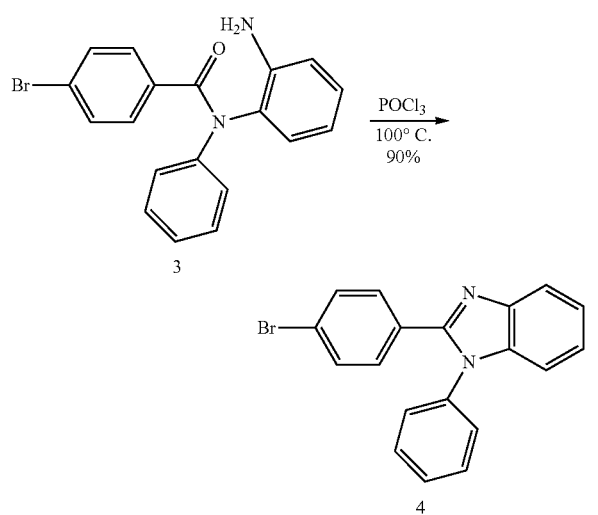

2-(4-bromophenyl)-1-phenyl-1H-benzo[d]imidazole (4)

To a suspension of amide 3 (9.6 g, 26 mmol) in anhydrous 1,4-dioxane (100 mL) was added phosphorus oxychloride (POCl$_3$) (9.2 mL, 100 mmol) slowly. The whole was then heated at 100° C. overnight. After cooling to RT, the mixture was poured into ice (200 g) with stirring. Filtration, followed by recrystallization in DCM/hexanes gave a pale grey solid 4 (8.2 g, in 90% yield).

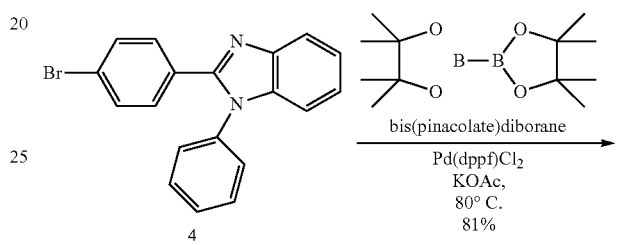

1-phenyl-2-(4-(4,4,5,5-tetramethyl-1,3,2-dioxaborolan-2-yl)phenyl)-1H-benzo[d]imidazole (5)

A mixture of Compound 4 (0.70 g, 2 mmol), bis(pinacolate)diborane (0.533 g, 2.1 mmol), bis(diphenylphosphino)ferrocene]dichloropalladium (Pd(dppf)Cl$_2$) (0.060 g, 0.08 mmol) and anhydrous potassium acetate (KOAc) (0.393 g, 4 mmol) in 1,4-dioxane (20 ml) was heated at about 80° C. under argon overnight. After cooling to RT, the whole was diluted with ethyl acetate (80 ml) then filtered. The solution was absorbed on silica gel, then purified by column chromatography (hexanes/ethyl acetate 5:1 to 3:1) to give a white solid 5 (0.64 g, in 81% yield).

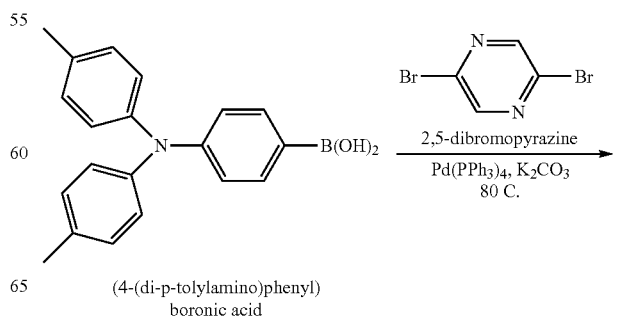

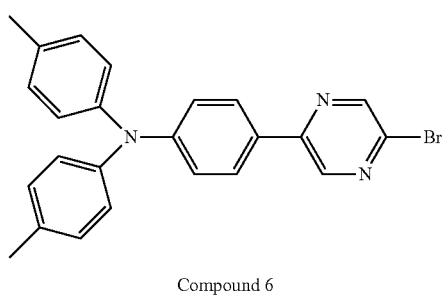

Compound 6

4-(5-bromopyrazin-2-yl)-N,N-di-p-tolylaniline (Compound 6)

A mixture of (4-(di-p-tolylamino)phenyl)boronic acid (0.74 g, 2.33 mmol), 2,5-dibromopyrazine (1.19 g, 5 mmol), Pd(PPh$_3$)$_4$ (0.14 g, 0.12 mmol) and K$_2$CO$_3$ (0.69 g, 5 mmol) in dioxane/water (80 mL/10 mL) was degassed and heated at about 80° C. overnight. The whole was diluted with ethyl acetate (250 mL), washed with brine, dried over Na$_2$SO$_4$, loaded on silica gel column and purified by flash column using eluents of hexanes to hexanes/dichloromethane (3:1). The desired fraction was collected, and a yellow solid (6) was obtained after removal of solvents, 0.63 g, in 63% yield.

Chemical Formula: C$_{43}$H$_{33}$N$_5$
Molecular Weight: 619.76

Compound BE-2

A mixture of 4-(5-bromopyrazin-2-yl)-N,N-di-p-tolylaniline (Compound 6) (0.63 g, 1.46 mmol), 1-phenyl-2-(4-(4,4,5,5-tetramethyl-1,3,2-dioxaborolan-2-yl)phenyl)-1H-benzo[d]imidazole (0.58 g, 1.46 mmol) (Compound 5), Pd(PPh$_3$)$_4$ (0.115 g, 0.1 mmol) and K$_2$CO$_3$ (0.414 g, 3 mmol) in dioxane/water (50 mL/10 mL) was degassed and heated at about 90° C. overnight. The resulting solution was diluted with ethyl acetate (250 mL), washed with brine, dried over Na$_2$SO$_4$, loaded on silica gel and purified by flash column using eluents of hexanes to dichloromethane to dichloromethane/ethyl acetate 4:1. The desired yellow fraction was collected, concentrated, recrystallized in dichloromethane/hexanes to give a yellow crystalline solid (Compound 6) (0.74 g, in 82% yield). Confirmed by LCMS (APCl+): calcd for C$_{43}$H$_{34}$N$_5$ (M+H): 620; found: 620.

Synthesis of BE-3

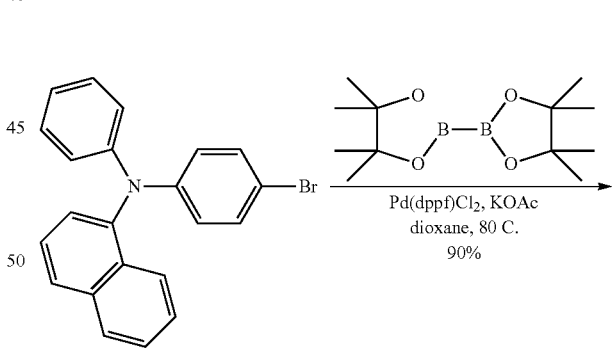

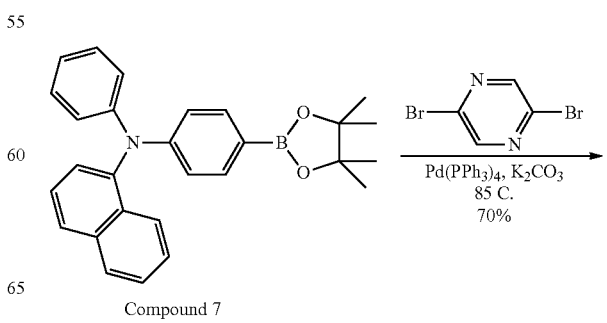

Compound 7

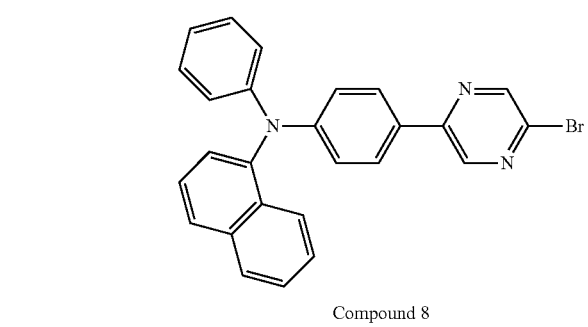

Compound 8

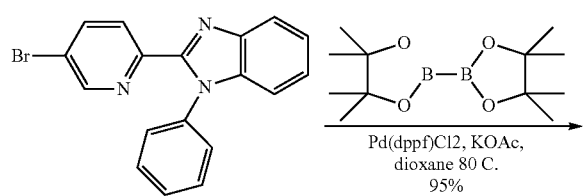

Compound 2

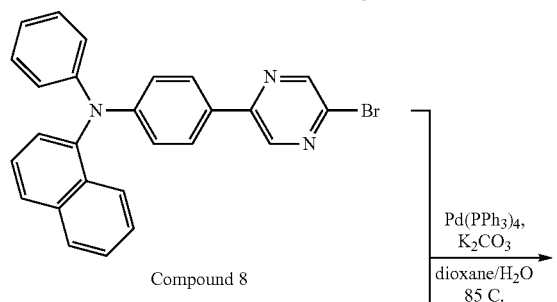

Compound 8

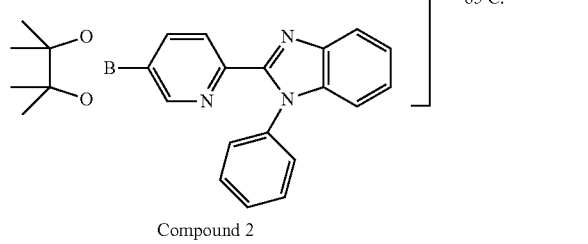

Compound 2

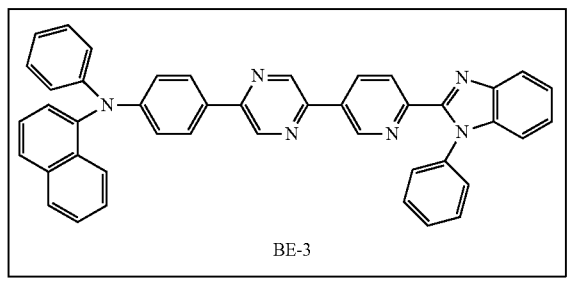

BE-3

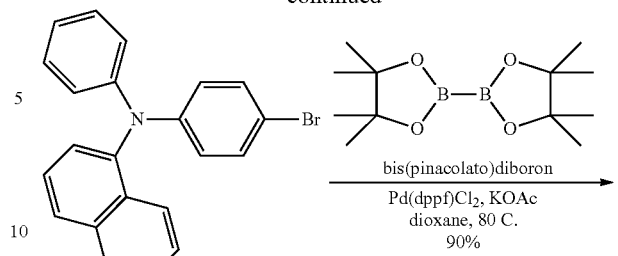

N-(4-bromophenyl)-N-phenylnaphthalen-1-amine

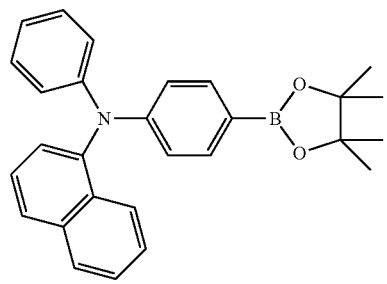

Compound 7

N-phenyl-N-(4-(4,4,5,5-tetramethyl-1,3,2-dioxaborolan-2-yl)phenyl)naphthalen-1-amine (Compound 7)

A mixture of N-(4-bromophenyl)-N-phenylnaphthalen-1-amine (7.14 g, 19.1 mmol), bis(pinacolato)diboron (5.08 g, 20 mmol), Pd(dppf)Cl$_2$ (0.73 g, 1.0 mmol) and KOAc (4.9 mmol, 50 mmol) in dioxane (100 mL) was degassed and heated at about 85° C. for 15 hours. The resulting mixture was poured into ethyl acetate (250 mL), filtered off precipitate, loaded on silica gel and purified by flash column using eluents of hexanes to hexanes/dichloromethane (8:1 to 6:1 to 2:1). The desired fraction was collected, and after removal of solvent to give a white solid (Compound 7) (6.0 g, in 75% yield).

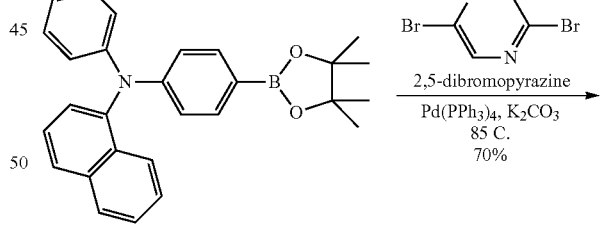

Compound 7

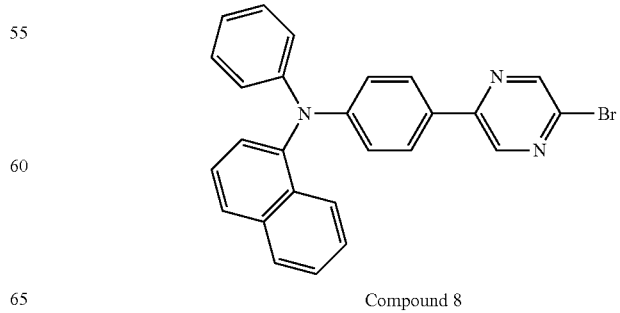

Compound 8

N-(4-(5-bromopyrazin-2-yl)phenyl)-N-phenylnaphthalen-1-amine (Compound 8)

A mixture of N-phenyl-N-(4-(4,4,5,5-tetramethyl-1,3,2-dioxaborolan-2-yl)phenyl)naphthalen-1-amine (Compound 7) (2.91 g, 6.91 mmol), 2,5-dibromopyrazine (3.56 g, 13.8 mmol), Pd(PPh$_3$)$_4$ (0.346 g, 0.3 mmol), K$_2$CO$_3$ (1.93 g, 14 mmol) in dioxane/water (80 mL/15 mL), was degassed and heated at about 85° C. overnight. The resulting mixture was diluted with ethyl acetate (250 mL), washed with brine, dried over Na$_2$SO$_4$, loaded on silica gel and purified by flash column using eluents of hexanes to hexanes/dichloromethane 4:1 to 2:1 to 3:2). The desired fraction was collected, after removal of solvent to give a yellow solid (Compound 8) (2.2 g, in 70.4% yield).

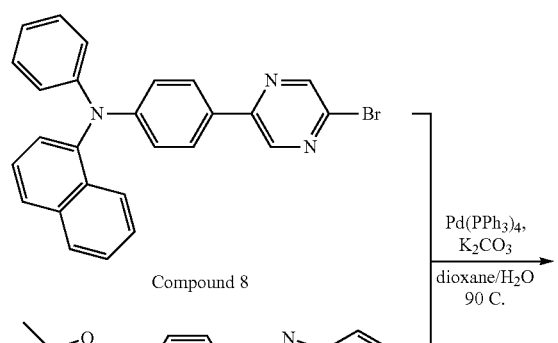

Compound 8

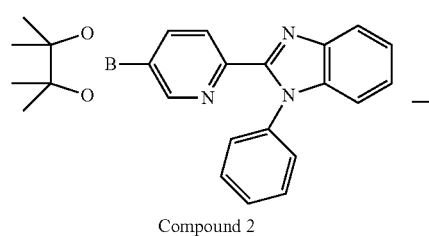

Compound 2

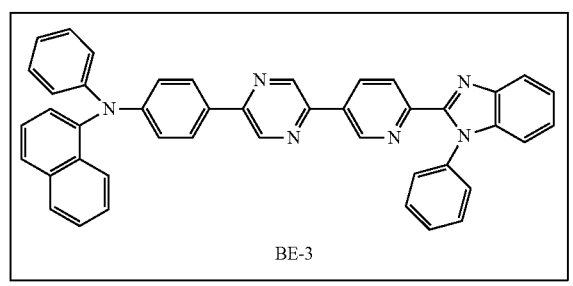

BE-3

Compound BE-3 a mixture of N-(4-(5-bromopyrazin-2-yl)phenyl)-N-phenylnaphthalen-1-amine (Compound 8) (1.17 g, 2.6 mmol), 1-phenyl-2-(5-(4,4,5,5-tetramethyl-1,3,2-dioxaborolan-2-yl)pyridin-2-yl)-1H-benzo[d]imidazole (Compound 2) (2.9 mmol), Pd(PPh$_3$)$_4$ (0.138 g, 0.12 mmol) and K$_2$CO$_3$ (0.69 g, 5 mmol) in dioxane/water (70 mL/16 mL) was degassed and heated at about 90° C. overnight. The resulting mixture was diluted with ethyl acetate (200 mL), washed with brine, dried over Na$_2$SO$_4$, loaded on silica gel and purified by flash column using eluents of hexanes/dichloromethane 1:1 to 1:2 to dichloromethane to dichloromethane/ethyl acetate 10:1 to 4:1. The desired fraction was collected and concentrated to give a yellow solid (1.39 g, in 83% yield). Confirmed by LCMS (APCl+): calcd for C$_{44}$H$_{31}$N$_6$ (M+H): 643; found: 643.

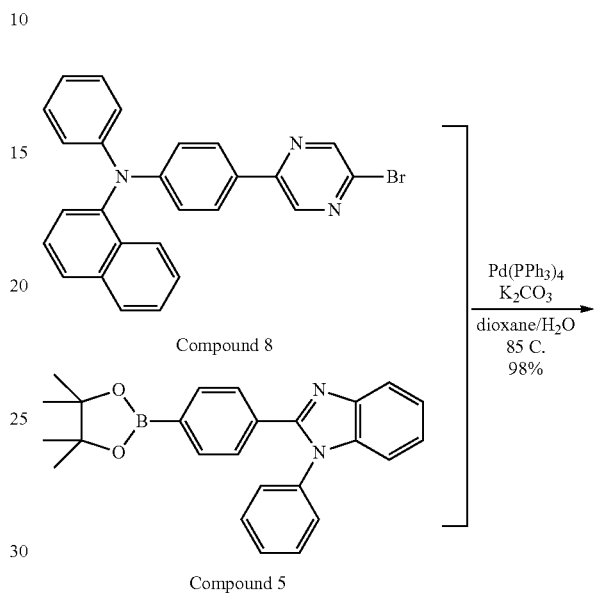

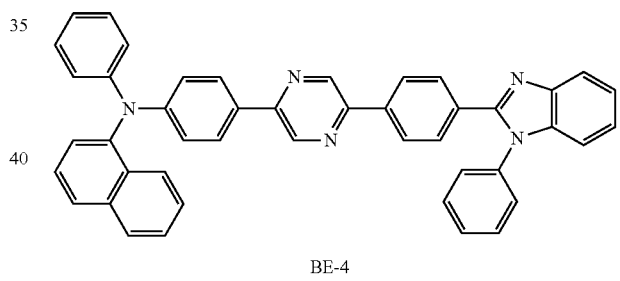

Compound BE-4

A mixture of N-(4-(5-bromopyrazin-2-yl)phenyl)-N-phenylnaphthalen-1-amine (Compound 8)(1.11 g, 2.46 mmol), 1-phenyl-2-(4-(4,4,5,5-tetramethyl-1,3,2-dioxaborolan-2-yl)phenyl)-1H-benzo[d]imidazole (Compound 5) (0.95 g, 2.4 mmol), Pd(PPh$_3$)$_4$ (0.14 g, 0.12 mmol) and K$_2$CO$_3$ (0.69 g, 5 mmol) in dioxane/water (70 mL/15 mL) was degassed and heated at 85° C. overnight. The mixture was diluted with ethyl acetate (200 mL), washed with brine, dried over Na$_2$SO$_4$, loaded on silica gel and purified by flash column using eluents of hexanes/dichloromethane 1:1 to dichloromethane to dichloromethane/ethyl acetate 9:1. The desired fraction was collected, concentrated and recrystallized in dichloromethane/hexanes to give yellow solid (BE-4) (1.50 g, in 98% yield). Confirmed by LCMS (APCl+): calcd for C$_{45}$H$_{32}$N$_5$ (M+H): 642; Found: 642.

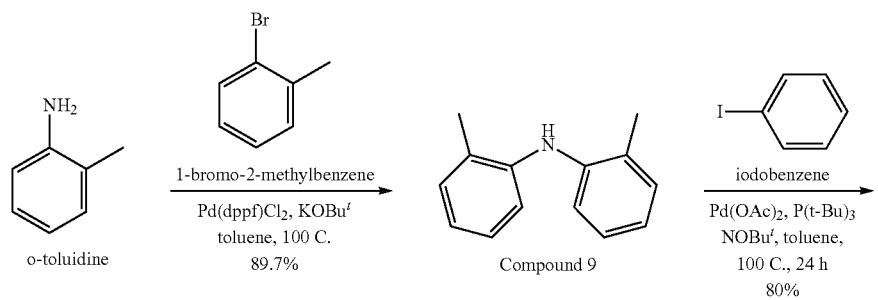
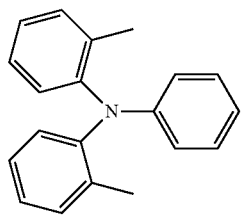
Compound 10
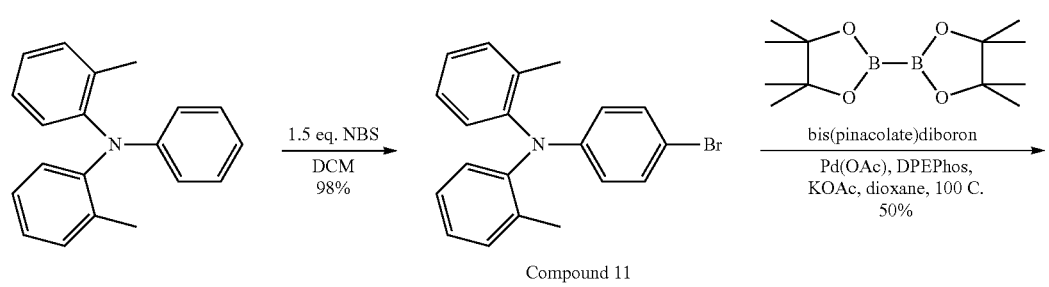
Compound 11
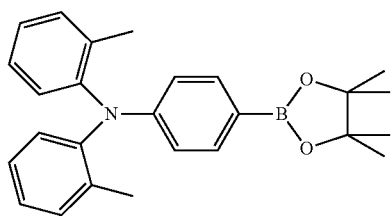
Compound 12
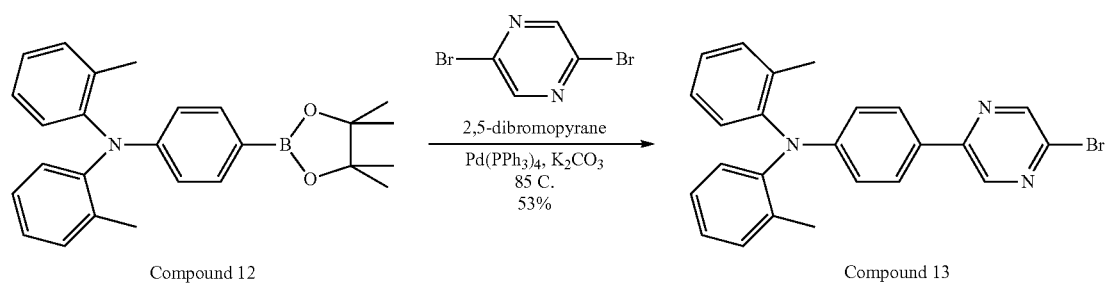
Compound 12    Compound 13

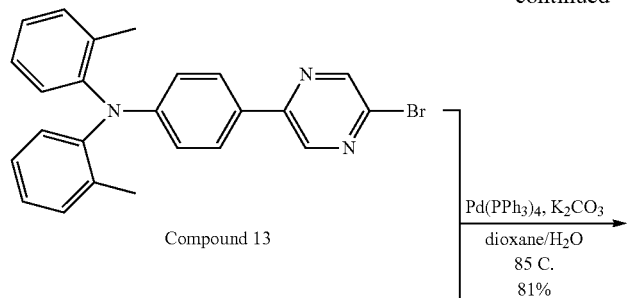

Compound 13

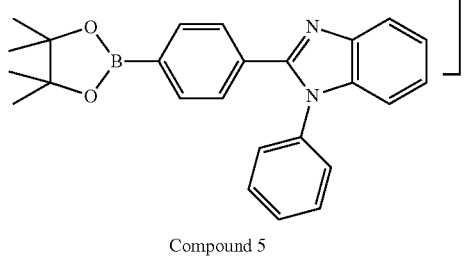

Compound 5

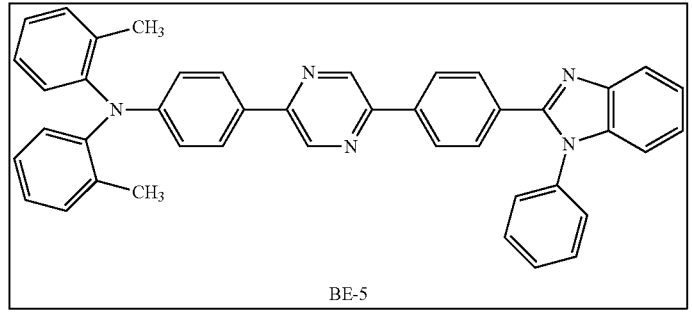

BE-5

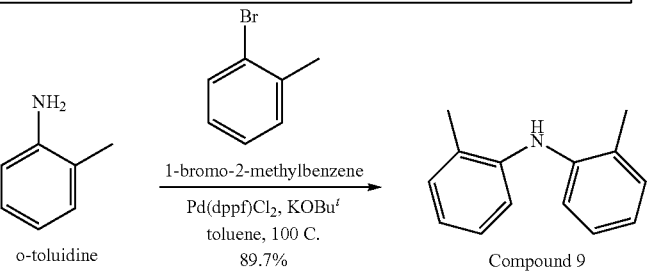

di-o-tolylamine (Compound 9)

A mixture of o-toluidine (6.05 g, 56.5 mmol), 1-bromo-2-methylbenzene (8.5 g, 50 mmol), Pd(dppf)Cl$_2$ and sodium tert-butoxide (9.6 g, 0.1 mmol) in toluene (120 mL) was degassed and heated at about 100° C. overnight. The mixture was purified by flash column using eluents of hexanes/dichloromethane 2:1 to give a white solid (Compound 9) (8.84 g, in 89.7% yield).

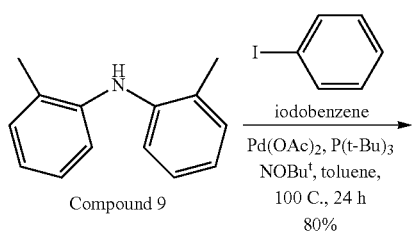

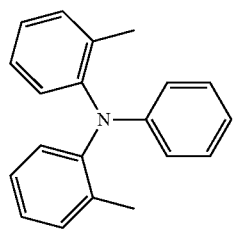

2-methyl-N-phenyl-N-(o-tolyl)aniline (Compound 10)

A mixture of di-o-tolylamine (Compound 9) (6.00 g, 30.4 mmol), iodobenzene (12.2 g, 60 mmol), Pd(OAc)$_2$ (0.34 g, 1.5 mmol), P(t-Bu)$_3$ (0.6 g, 3 mmol), sodium tert-butoxide (5.76 g, 60 mmol) in toluene (120 mL) was degassed and heated at about 120° C. for 40 hours. The resulting mixture was diluted with ethyl acetate (200 mL), washed with brine, dried over Na$_2$SO$_4$, loaded on silica gel and purified by flash column using eluents of hexanes to give a white solid (Compound 10) (8.2 g, in 98% yield).

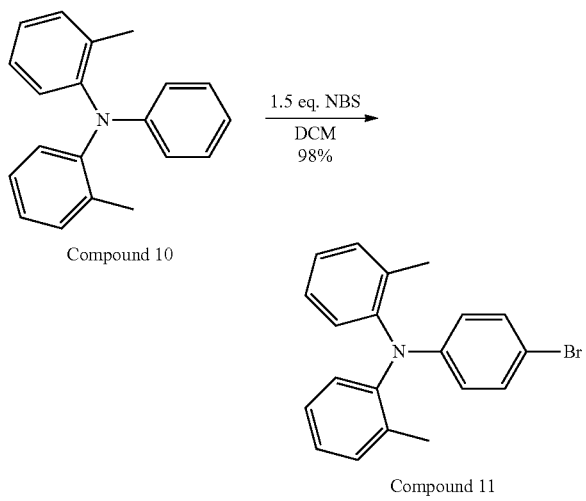

Compound 10

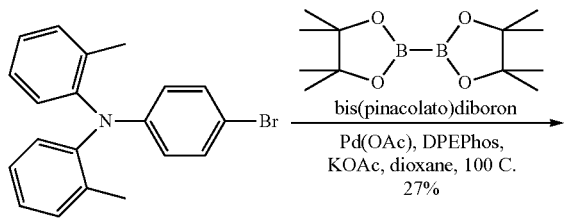

Compound 11

N-(4-bromophenyl)-2-methyl-N-(o-tolyl)aniline (Compound 11)

To a solution of 2-methyl-N-phenyl-N-(o-tolyl)aniline (Compound 10) (8.2 g, 30 mmol) in dichloromethane (DCM) (100 mL), was added n-bromosuccinimide (NBS) (5.34 g, 30 mmol) at about 0° C. and stirred for about 4 hours. The resulting mixture was worked up with dichloromethane/brine, dried over Na$_2$SO$_4$, loaded on silica gel and purified by flash column using eluents of hexanes to hexanes/dichloromethane 9:1. The desired fraction was collected, and removal of solvent gave a white solid (Compound 11) (10.7 g, in 100% yield).

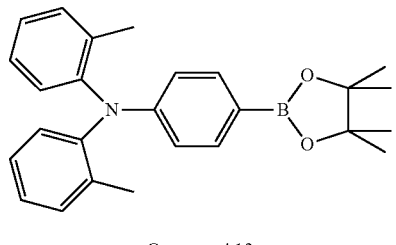

Compound 12

2-methyl-N-(4-(4,4,5,5-tetramethyl-1,3,2-dioxaborolan-2-yl)phenyl)-N-(o-tolyl)aniline (Compound 12)

A mixture of N-(4-bromophenyl)-2-methyl-N-(o-tolyl) aniline (Compound 11) (10.7 g, 30.4 mmol), bis(pinacolato) diboron (10.16 g, 40 mmol), KOAc (6.0 g, 0.1 mol), Pd(OAc)$_2$ (0.336 g, 1.5 mmol), Bis(2-diphenylphosphinophenyl)ether (1.614 g, 3 mmol) in dioxane (100 mL) was degassed and heated at about 100° C. overnight. The resulting mixture was worked up with ethyl acetate/brine, dried over Na$_2$SO$_4$, loaded on silica gel and purified by flash column using eluents of hexanes to hexanes/dichloromethane 4:1. The desired fraction was collected and the solvent was removed to give a colorless oil (Compound 12) (3.3 g, in 27% yield).

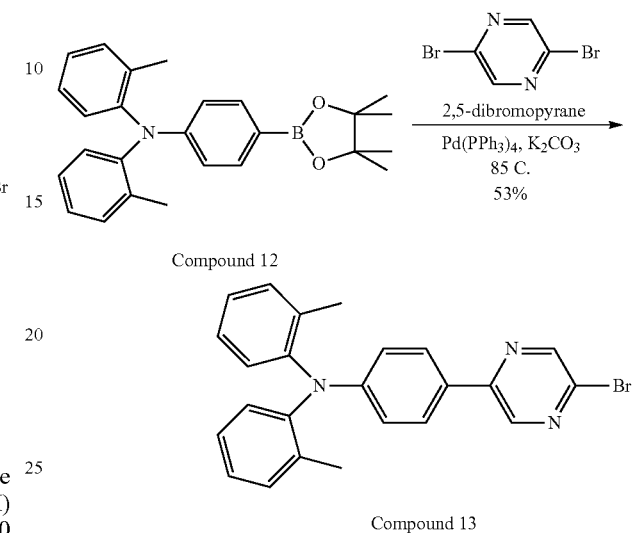

Compound 13

N-(4-(5-bromopyrazin-2-yl)phenyl)-2-methyl-N-(o-tolyl)aniline (Compound 13)

2-methyl-N-(4-(4,4,5,5-tetramethyl-1,3,2-dioxaborolan-2-yl)phenyl)-N-(o-tolyl)aniline (Compound 12) (3.3 g, 8.3 mmol), 2,5-dibromopyrazine (4.27 g, 16 mmol), Pd(PPh$_3$)$_4$ (0.46 g, 0.4 mmol), K$_2$CO$_3$ (2.21 g, 16 mmol) in dioxane/water (100 mL/16 mL), was degassed and heated at about 80° C. overnight. The resulting mixture was worked up with ethyl acetate/brine, dried over Na$_2$SO$_4$, loaded on silica gel, purified by flash column using eluents of hexanes to hexanes/dichloromethane 9:1 to 6:1 to 4:1). The desired fraction was collected, and a yellow solid (Compound 13) was obtained after removal of solvents (1.9 g, in 53% yield).

65

-continued

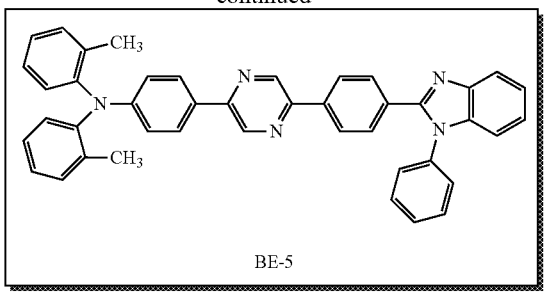

Compound BE-5 a mixture of N-(4-(5-bromopyrazin-2-yl)phenyl)-2-methyl-N-(o-tolyl)aniline (Compound 13) (1.9 g, 4.4 mmol),

66

1-phenyl-2-(4-(4,4,5,5-tetramethyl-1,3,2-dioxaborolan-2-yl)phenyl)-1H-benzo[d]imidazole (Compound 5) (1.75 g, 4.4 mmol), Pd(PPh$_3$)$_4$ (0.25 g, 0.22 mmol), K$_2$CO$_3$ (1.38 g, 10 mmol) in dioxane/water (100 mL/16 mL), was degassed and heated at about 90° C. overnight. The resulting mixture was worked up with ethyl acetate/brine, dried over Na$_2$SO$_4$, loaded on silica gel and purified by flash column using eluents of hexanes to hexanes/dichloromethane 8:1 to 4:1 to dichloromethane/ethyl acetate 9:1. The desired fraction was collected, and after removal of solvent and recrystallization, gave a yellow solid (Compound BE-5) (2.2 g, in 80.6% yield). Confirmed by LCMS (APCl+): calcd for C$_{43}$H$_{34}$N$_5$ (M+H): 620; found: 620.

Synthesis of BE-6

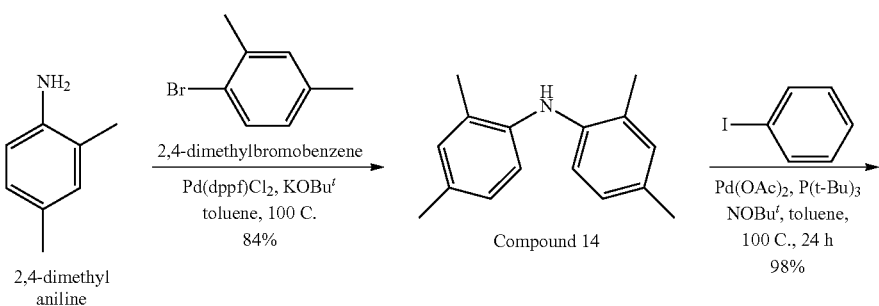

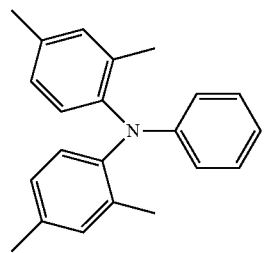

Compound 15

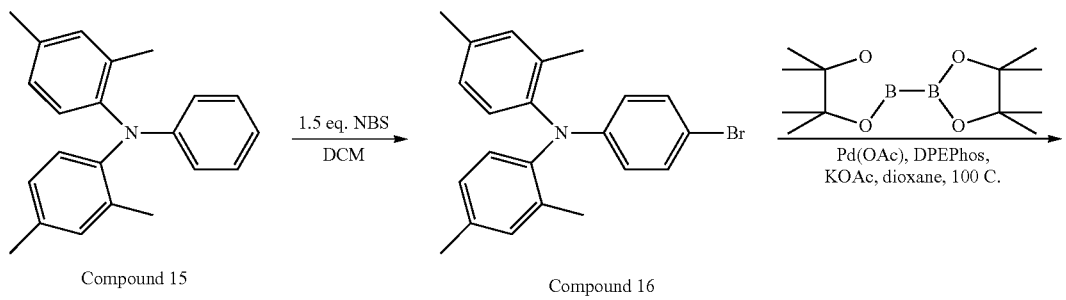

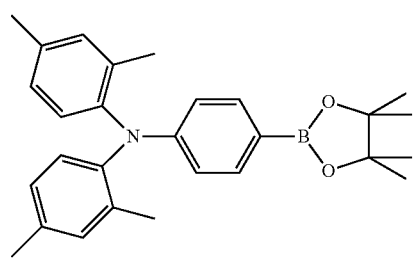

Compound 17

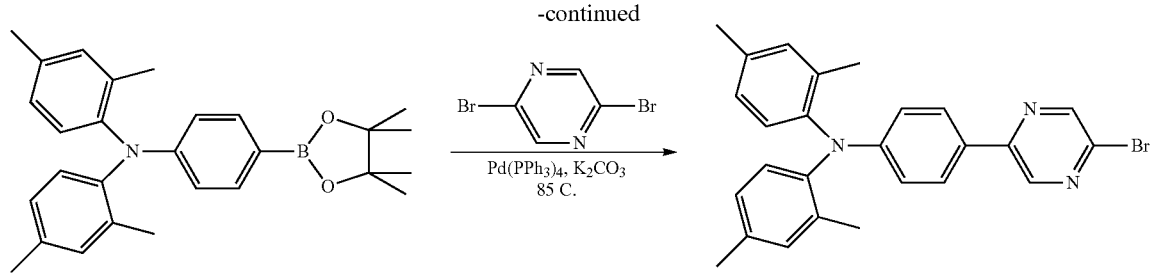

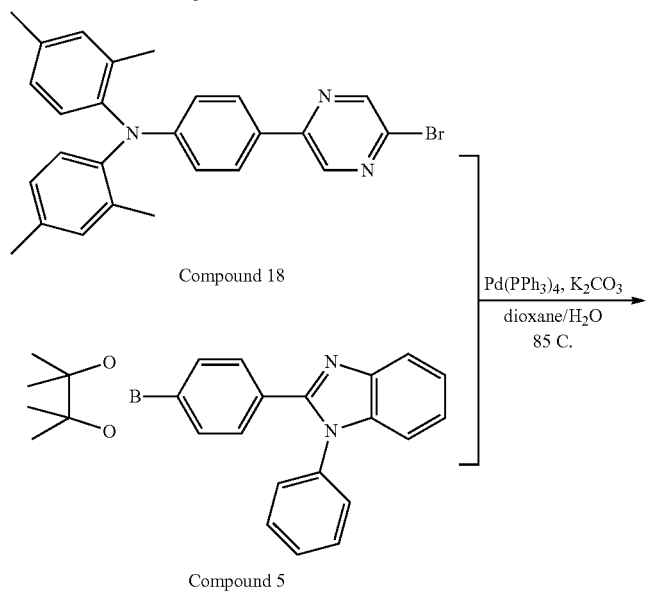

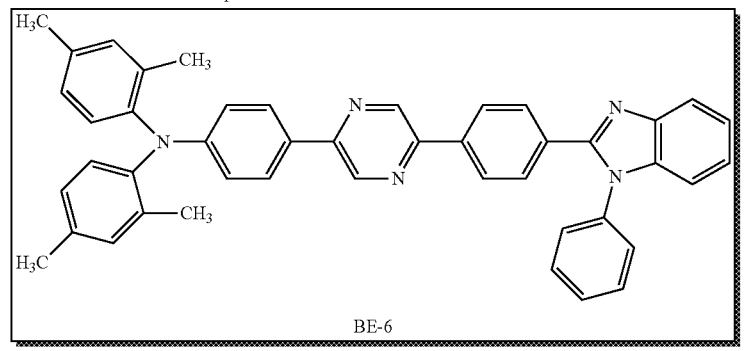

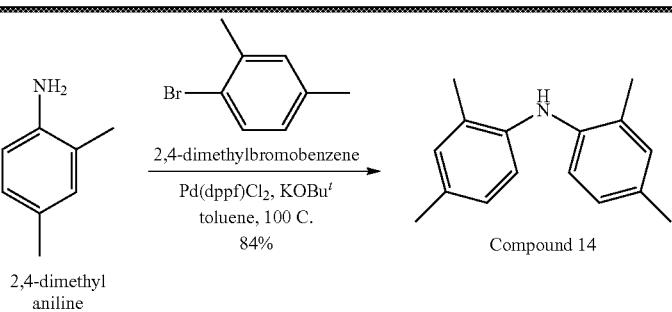

Bis(2,4-dimethylphenyl)amine (Compound 14)

A mixture of 2,4-dimethylaniline (6.05 g, 50 mmol), 2,4-dimethylbromobenzene (9.25 g, 50 mmol), Pd(dppf)Cl$_2$ (0.88 g, 1.2 mmol), sodium tert-butoxide (KOBu$^t$) (9.6 g, 0.1 mmol) in toluene (120 mL) was degassed and heated at 100° C. overnight. The resulting mixture was worked up with dichloromethane/brine, dried over Na$_2$SO$_4$, loaded on silica gel and purified by flash column using eluents of hexanes to hexanes/dichloromethane 9:1. After removal of solvent, a liquid was obtained (9.45 g, in 84% yield).

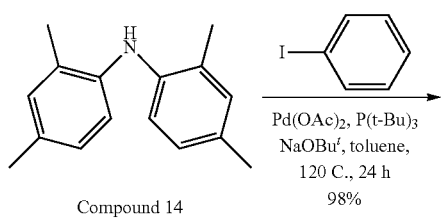

Compound 14

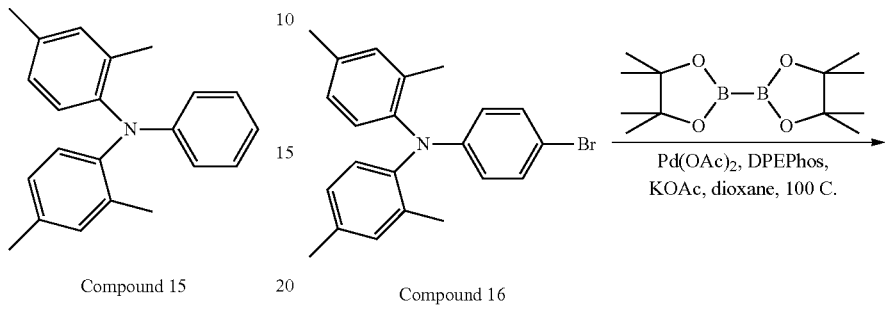

Compound 15

N-(2,4-dimethylphenyl)-2,4-dimethyl-N-phenylaniline (Compound 15)

A mixture of bis(2,4-dimethylphenyl)amine (Compound 14) (9.4 g, 41.8 mmol), iodobenzene (17.14 g, 84 mmol), Pd(OAc)$_2$ (0.47 g, 2.1 mmol), P(t-Bu)$_3$ (0.848 g, 4.2 mmol), sodium tert-butoxide (7.68 g, 80 mmol) in toluene (120 mL) was degassed and heated at 120° C. for 16 hours. The resulting mixture was poured into ethyl acetate (250 mL), washed with brine, dried over Na$_2$SO$_4$, loaded on silicagel and purified by flash column using eluent of hexanes. After removal of solvent, an oil (Compound 15) was obtained (12.4 g, in 98.6% yield).

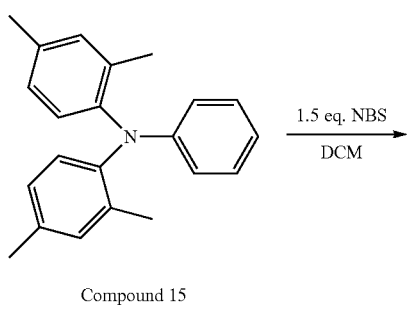

Compound 15

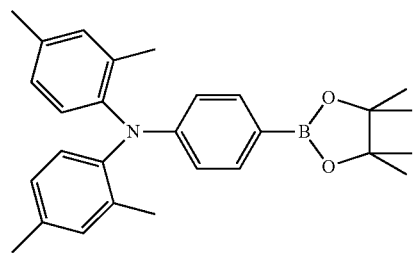

Compound 16

N-(4-bromophenyl)-N-(2,4-dimethylphenyl)-2,4-dimethylaniline (Compound 16)

To a solution of N-(2,4-dimethylphenyl)-2,4-dimethyl-N-phenylaniline (Compound 15) (12.4 g, 41 mmol) in dichloromethane (200 mL), was added NBS (8.01 g, 45 mmol) at 0° C. The whole was stirred for about 3 hours and worked up with brine. The organic phase was dried over Na$_2$SO$_4$, loaded on silica gel and purified by flash column using eluents of hexanes. After removal of solvents, a colorless oil (Compound 16) was obtained (15 g, in 96% yield).

Compound 16

Compound 17

N-(2,4-dimethylphenyl)-2,4-dimethyl-N-(4-(4,4,5,5-tetramethyl-1,3,2-dioxaborolan-2-yl)phenyl)aniline (Compound 17)

A mixture of N-(4-bromophenyl)-N-(2,4-dimethylphenyl)-2,4-dimethylaniline (Compound 16) (15 g, 39.5 mmol), bis(pinacolato)diboron (10.41 g, 41 mmol), KOAc (7.84 g, 80 mmol), Bis(2-diphenylphosphinophenyl)ether (3.23 g, 6 mmol) and Pd(OAc)$_2$ (0.44 g, 2 mmol) in dioxane (100 mL) was degassed and heated at about 100° C. overnight. The resulting mixture was poured into ethyl acetate (200 mL), washed with brine, dried over Na$_2$SO$_4$, loaded on silica gel and purified by flash column using eluents of hexanes to hexanes/ethyl acetate 18:1. After removal of solvents, a white solid (Compound 17) was obtained (14 g, in 83% yield).

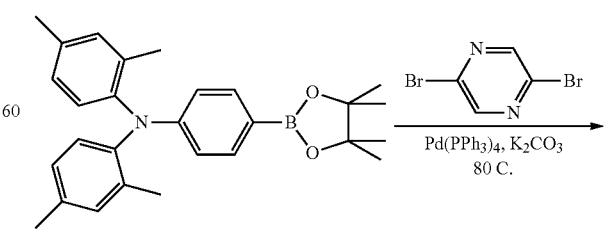

Compound 17

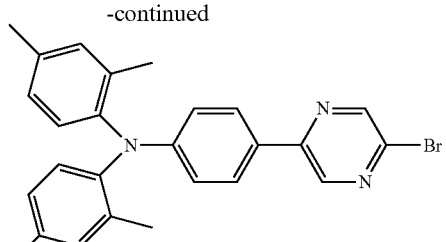

Compound 18

N-(4-(5-bromopyrazin-2-yl)phenyl)-N-(2,4-dimethylphenyl)-2,4-dimethylaniline (Compound 18)

A mixture of N-(2,4-dimethylphenyl)-2,4-dimethyl-N-(4-(4,4,5,5-tetramethyl-1,3,2-dioxaborolan-2-yl)phenyl)aniline (Compound 17) (6.0 g, 14 mmol), 2,5-dibromopyrazine (7.74 g, 30 mmol), Pd(PPh$_3$)$_4$ (0.5 g, 0.43 mmol), K$_2$CO$_3$ (4.14 g, 30 mmol) in dioxane/water (80 mL/17 mL) was degassed and heated at about 80° C. overnight. The resulting mixture was poured into ethyl acetate (200 mL), washed with brine, dried over Na$_2$SO$_4$, then loaded on silica gel and purified by flash column using eluents of hexanes to hexanes/dichloromethane 9:1 to 6:1 to 7:3. The desired yellow fraction was collected, and a yellow solid (Compound 18) was obtained after removal of solvents (3.83 g, 60% yield).

Compound BE-6

A mixture of N-(4-(5-bromopyrazin-2-yl)phenyl)-N-(2,4-dimethylphenyl)-2,4-dimethylaniline (Compound 18) (1.67 g, 3.65 mmol), 1-phenyl-2-(4-(4,4,5,5-tetramethyl-1,3,2-dioxaborolan-2-yl)phenyl)-1H-benzo[d]imidazole (Compound 5) (1.445 g, 3.65 mmol), Pd(PPh$_3$)$_4$ (0.21 g, 0.18 mmol), K$_2$CO$_3$ (0.966 g, 7 mmol) in dioxane/water (50 mL/10 mL) was degassed and heated at about 100° C. overnight. The resulting mixture was poured into ethyl acetate (200 mL), washed with brine, dried over Na$_2$SO$_4$, loaded on silica gel and purified by flash column using eluents of hexanes to hexanes/dichloromethane 1:1 to dichloromethane to dichloromethane/ethyl acetate 90:5. The desired yellow fraction was collected. After removal of solvent, a yellow solid (BE-6) was obtained (2.2 g, in 93% yield). Confirmed by LCMS (APCl+): calcd for C$_{45}$H$_{38}$N$_5$ (M+H): 648; Found: 648.

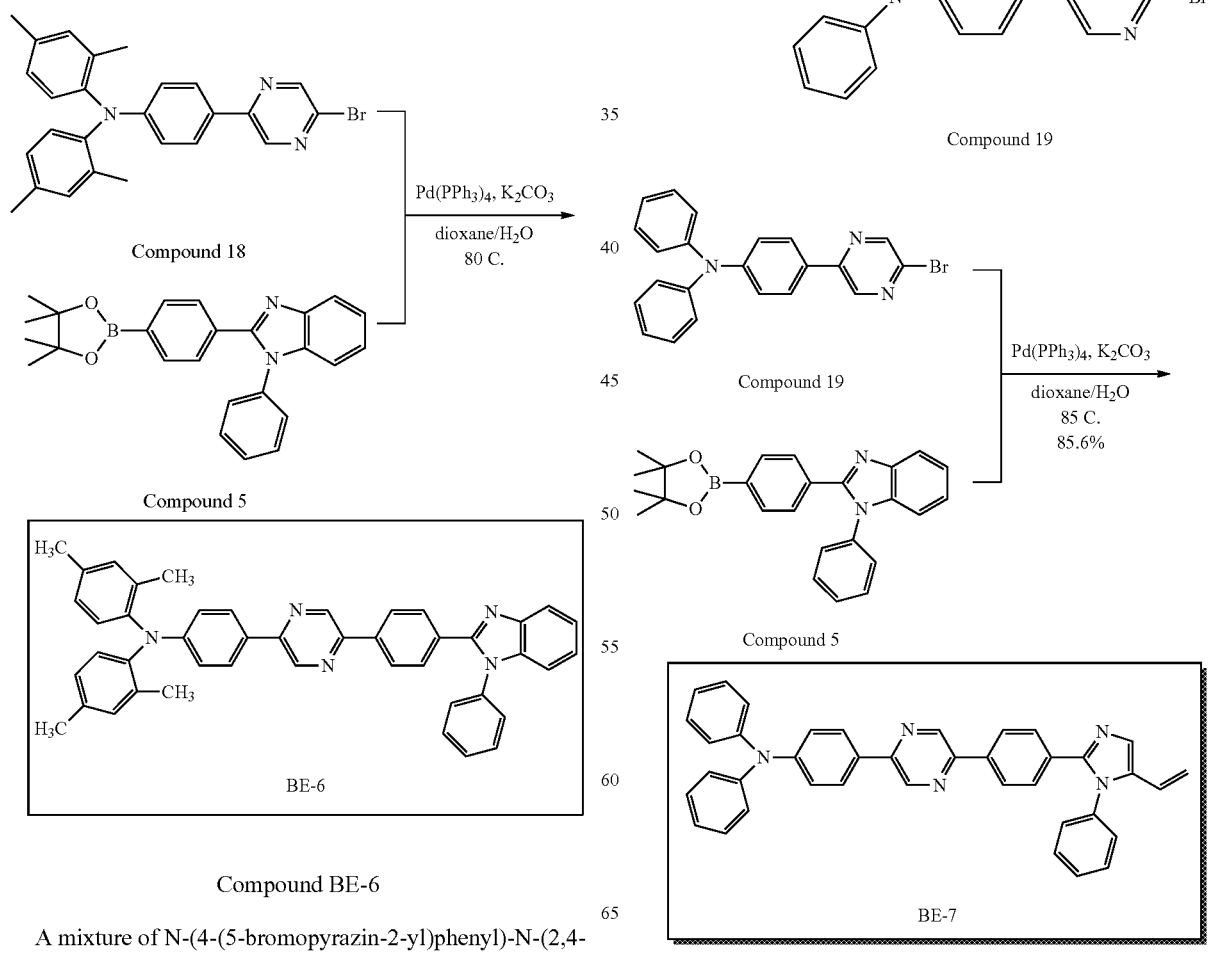

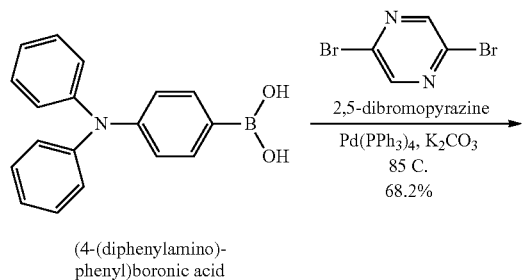

(4-(diphenylamino)-
phenyl)boronic acid

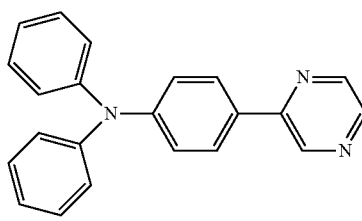

Compound 19

4-(5-bromopyrazin-2-yl)-N,N-diphenylaniline (Compound 19)

A mixture of (4-(diphenylamino)phenyl)boronic acid (3.26 g, 11.3 mmol), 2,5-dibromopyrazine (5.82 g, 22.6 mmol), Pd(PPh$_3$)$_4$ (0.635 g, 0.55 mmol), K$_2$CO$_3$ (3.45 g, 25 mmol) in dioxane/water (100 mL/16 mL) was degassed and heated at about 85° C. for about 20 hours. The resulting mixture was poured into ethyl acetate (250 mL), washed with brine, dried over Na$_2$SO$_4$, loaded on silica gel and purified by flash column using eluents of hexanes to hexanes/dichloromethane 4:1. After removal of solvent, a yellow solid (Compound 19) was obtained (3.1 g, in 68.2% yield).

BE-7

Compound BE-7

A mixture of 4-(5-bromopyrazin-2-yl)-N,N-diphenylaniline (Compound 19) (1.54 g, 3.83 mmol), 1-phenyl-2-(4-(4,4,5,5-tetramethyl-1,3,2-dioxaborolan-2-yl)phenyl)-1H-benzo[d]imidazole (Compound 5) (1.52 g, 3.83 mmol), Pd(PPh$_3$)$_4$ (0.22 g, 0.19 mmol), K$_2$CO$_3$ (1.104 g, 8 mmol) in dioxane/water (100 mL/15 mL) was degassed and heated at about 90° C. for about 16 hours. The resulting mixture was poured into ethyl acetate (250 mL), washed with brine, concentrated and yellow precipitate formed. Filtration and washing with ethyl acetate gave a solid and filtrate. The filtrate was loaded n silica gel was loaded on silica gel and purified by flash column using eluents of hexanes to dichloromethane to dichloromethane/ethyl acetate (9:1 to 4:1). The desired fraction was collected. The solid from the filtration was dissolved in dichloromethane, purified by flash column using eluents of hexanes to dichloromethane to dichloromethane/ethyl acetate 9:1. The desired fraction was collected. Both desired fractions from the chromatography were combined, after removal of solvent, the solid was recrystallized in dichloromethane/ethyl acetate to give a yellow solid (BE-7), 1.94 g in 85.6% yield. Confirmed by LCMS (APCl+): calcd for C$_{41}$H$_{30}$N$_5$ (M+H): 592; found: 592.

Synthesis of BE-8

75

-continued

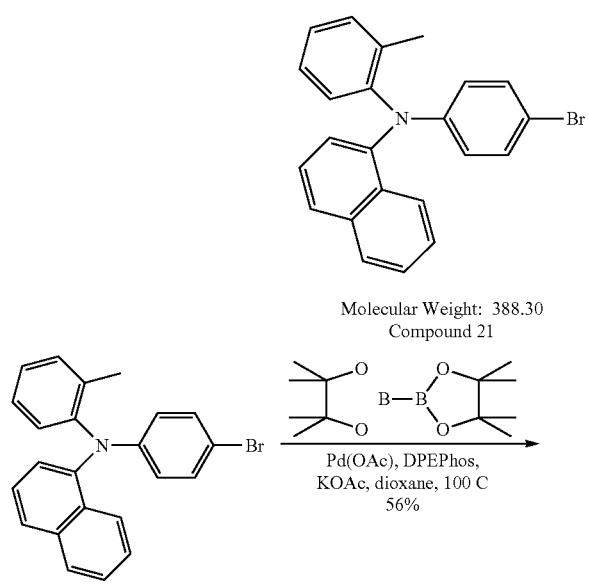

Molecular Weight: 388.30
Compound 21

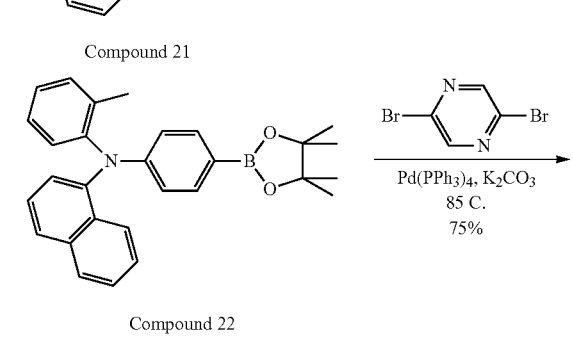

Compound 21

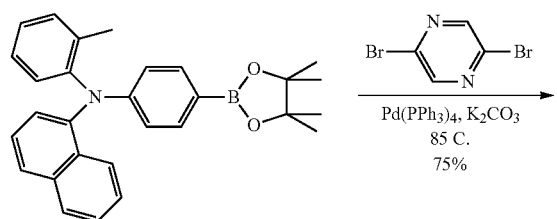

Compound 22

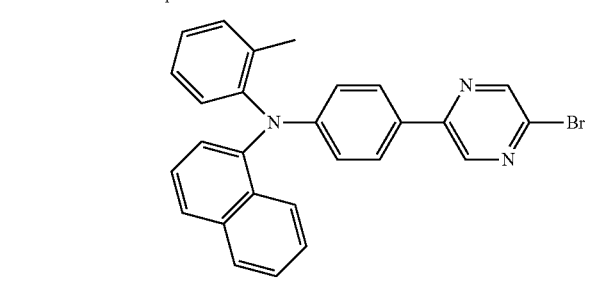

Compound 23

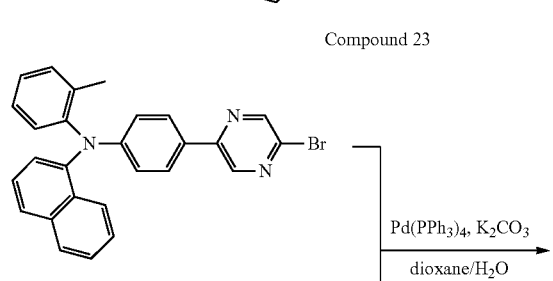

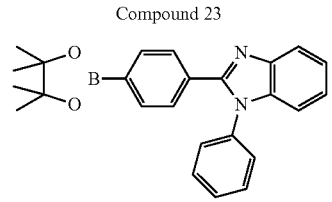

Compound 5

76

-continued

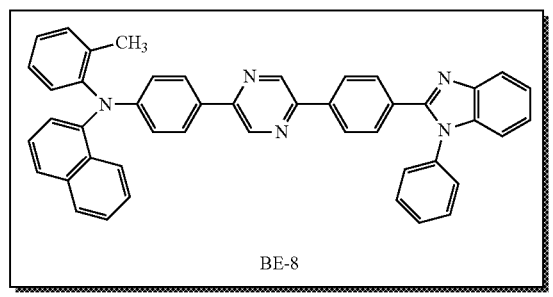

Molecular Weight: 655.79

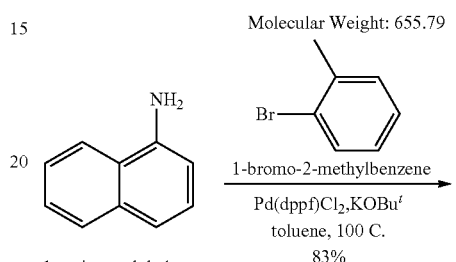

N-(o-tolyl)naphthalen-1-amine (Compound 20)

A mixture of 1-aminonaphthalene (7.15 g, 50 mmol), 1-bromo-2-methylbenzene (8.5 g, 50 mmol), Pd(dppf)Cl$_2$ (1.0 g, 1.36 mmol), sodium tert-butoxide (9.6 g, 0.1 mol) in toluene (120 mL) was degassed and heated at about 100° C. overnight. The resulting mixture was worked up with ethyl acetate/brine, dried over Na$_2$SO$_4$, loaded on silica gel and purified by flash column using eluents of hexanes to hexanes/dichloromethane 9:1. After removal of solvents, an oil (Compound 20) was obtained, 10.2 g in 91.5% yield.

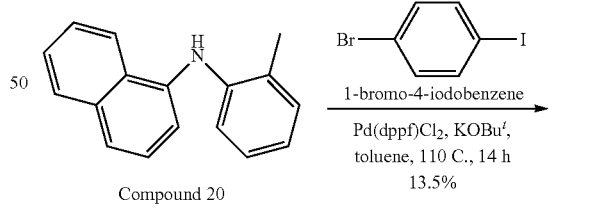

Compound 20

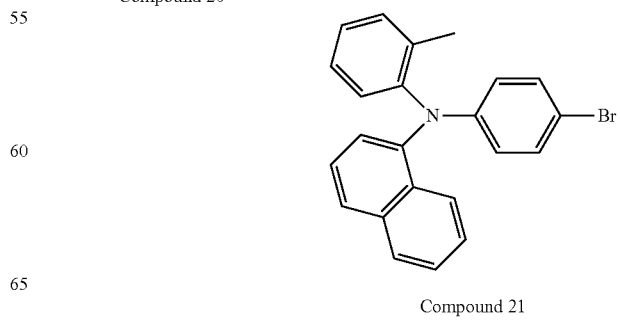

Compound 21

N-(4-bromophenyl)-N-(o-tolyl)naphthalen-1-amine (Compound 21)

A mixture of N-(o-tolyl)naphthalen-1-amine (Compound 20) (2.0 g, 8.6 mmol), 1-bromo-4-iodobenzene (8.67 g, 30 mmol), Pd(dppf)Cl$_2$ (0.365 g, 0.5 mmol), potassium tert-butoxide (1.96 g, 20 mmol) in toluene was degassed and heated at 110° C. overnight. The resulting mixture was worked up with ethyl acetae/brine, dried over Na$_2$SO$_4$, loaded on silica gel and purified by flash column using eluents of hexanes to hexanes/dichloromethane 9:1. After removal of solvents, a yellow solid (Compound 21) was obtained, 0.45 g in 13.5% yield.

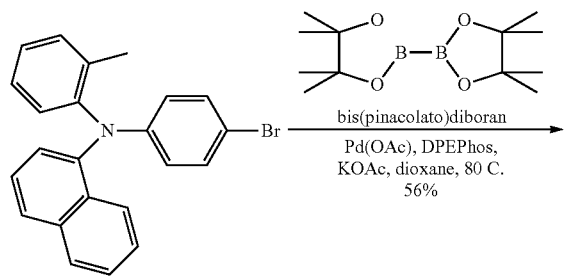

Compound 21

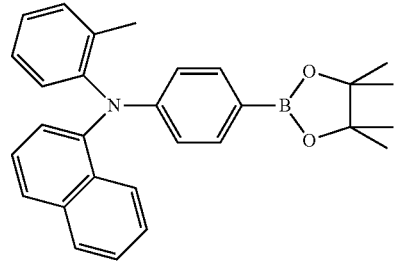

Compound 22

N-(4-(4,4,5,5-tetramethyl-1,3,2-dioxaborolan-2-yl)phenyl)-N-(o-tolyl)naphthalen-1-amine (Compound 22)

A mixture of N-(4-bromophenyl)-N-(o-tolyl)naphthalen-1-amine (Compound 21) (0.87 g, 2.24 mmol), bis(pinacolato) diboran (0.635 g, 2.5 mmol), Pd(dppf)Cl$_2$ (81.8 mg, 0.11 mmol), KOAc (0.49 g, 5 mmol) in dioxane (50 mL) was degassed and heated at 80° C. overnight. The resulting mixture was worked up with ethyl acetate/brine, dried over Na$_2$SO$_4$, loaded on silica gel and purified by flash column using eluents of hexanes to hexanes/ethyl acetate 18:1. After removal of solvents, a yellow solid (Compound 22) was obtained, 0.55 g in 56% yield.

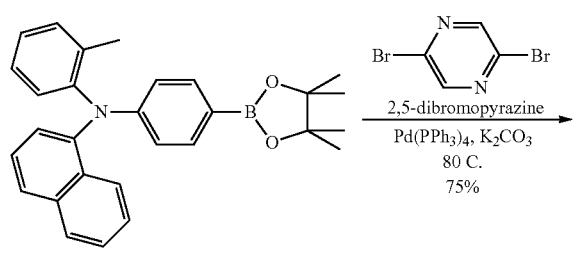

Compound 22

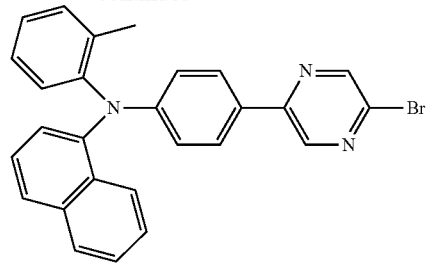

Compound 23

N-(4-(5-bromopyrazin-2-yl)phenyl)-N-(o-tolyl)naphthalen-1-amine (Compound 23)

A mixture of N-(4-(4,4,5,5-tetramethyl-1,3,2-dioxaborolan-2-yl)phenyl)-N-(o-tolyl)naphthalen-1-amine (Compound 22) (0.55 g, 1.26 mmol), 2,5-dibromopyrazine (0.77 g, 3.0 mmol), Pd(PPh$_3$)$_4$ (0.1 g, 0.09 mmol), K$_2$CO$_3$ (0.414 g, 3 mmol) in dioxane/water (40 mL/8 mL) was degassed and heated at 80° C. overnight. The resulting mixture was worked up with ethyl acetate/brine, dried over Na$_2$SO$_4$, loaded on silica gel and purified by flash column using eluents of hexanes/dichloromethane 9:1 to 3:2. After removal of solvents, a yellow solid (Compound 23) was obtained, 0.44 g in 75% yield.

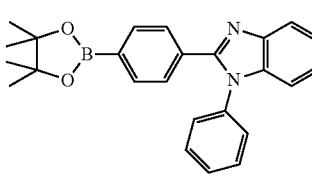

Compound 23

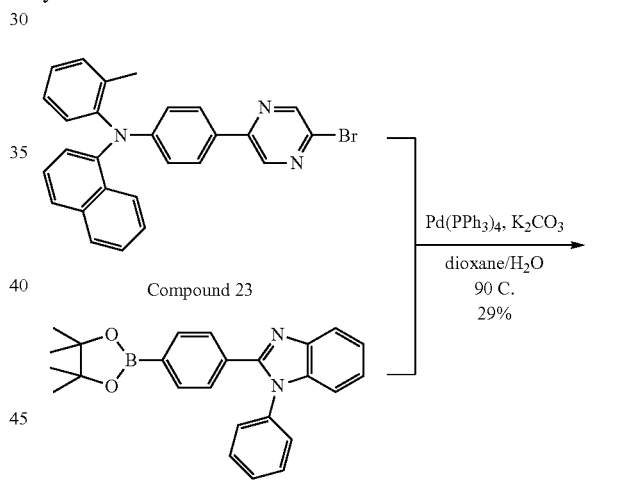

Compound 5

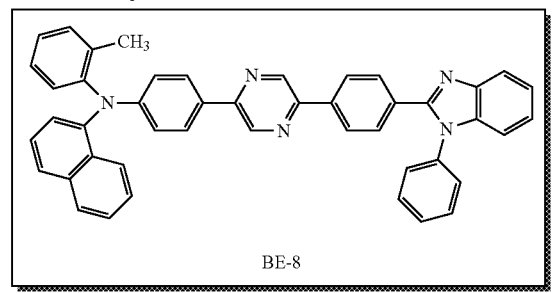

BE-8

Molecular Weight: 655.79

Compound BE-8

A mixture of N-(4-(5-bromopyrazin-2-yl)phenyl)-N-(o-tolyl)naphthalen-1-amine (Compound 23) (0.44 g, 0.94 mmol), 1-phenyl-2-(4-(4,4,5,5-tetramethyl-1,3,2-dioxaborolan-2-yl)phenyl)-1H-benzo[d]imidazole (Compound 5) (0.374 g, 0.94 mmol), Pd(PPh$_3$)$_4$ (0.058 g, 0.05 mmol), K$_2$CO$_3$ (0.276 g, 2 mmol) in dioxane/water (40 mL/8 mL) was degassed and heated at about 90° C. for 5 hours. The resulting mixture was worked up with ethyl acetate/brine, dried over Na$_2$SO$_4$, loaded on silica gel and purified by flash column using eluents of hexanes to hexanes/dichloromethane 4:1 to 1:1 to dichloromethane/ethyl acetate 10:1. The desired fraction was collected, after removal of solvents, the solid was recrystallized in dichloromethane/hexanes to give a yellow solid (BE-8), 0.18 g in 29% yield. Confirmed by LCMS (APCl+): calcd for C$_{46}$H$_{34}$N$_5$ (M+H): 656; Found: 656.

Example of OLED Device Configuration and Performance

Example 2

ITO coated glass substrates will be cleaned by ultrasound in water, acetone, and consecutively in 2-propanol, baked at 110° C. for 3 hours, followed by treatment with oxygen plasma for 5 min. A layer of PEDOT: PSS (Baytron P purchased from H.C. Starck) will be spin-coated at 3000 rpm onto the pre-cleaned and O$_2$-plasma treated (ITO)-substrate and annealed at about 180° C. for 30 min, to yield a thickness of around 55 nm. In a glove-box hosted vacuum deposition system at a pressure of 10$^{-7}$ torr (1 torr=133.322 Pa), DTASi will be first deposited on top of PEDOT/PSS layer at deposition rate of 0.06 nm/s, yielding a 30 nm thick film. Then the BE-2 will be heated and deposited on top of DTASi, yielding about a 5 nm thick film, followed by co-deposition of BE-2 and Ir(PIQ)$_2$(acac) at depositions rates of about 0.06 nm/s to form a 5 nm thick layer, and deposition of another BE-2 layer having a thickness of about 5 nm. Then 1,3,5-tris(N-phenylbenzimidizol-2-yl)benzene (TPBI) at deposition rate around 0.06 nm/s will be deposited on the BE-2 layer to form a 40 nm thick film. LiF (1.0 nm) and Al (100 nm) will be then deposited successively at deposition rates of 0.005 and 0.2 nm/s, respectively. Each individual device will have areas of 0.14 cm$^2$.

Example 3

All spectra will be measured with an Ocean Optics HR 4000 spectrometer and I-V-L characteristics were taken with a Keithley 2400 SourceMeter and Newport 2832-C power meter and 818 UV detector. All device operation will be performed inside a nitrogen-filled glove-box. An example of a configuration of the device (Device-A) is shown in FIG. 4.

It is anticipated that upon determining the luminescent efficiency and power efficiency as a function of luminance of Device-A, a plot of the electroluminescence spectrum of Device-A, and the CRI of Device A, BE-2 will be suitable as a host material in hybrid OLED devices.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A compound represented by a formula:

HT-[Ph$^1$]$_r$-Py-Het-ET wherein HT is optionally substituted diphenylamine or optionally substituted phenyl(naphthyl)amine, each Ph$^1$ is independently optionally substituted p-phenylene, wherein the p-phenylene directly bonded to HT may optionally form a bond to a phenyl of HT to form a three ring system;

Py is optionally substituted pyrazin-2,5-ylene;

Het is optionally substituted p-phenylene or optionally substituted pyridin-2,5-ylene;

ET is optionally substituted benzimidazol-2-yl, optionally substituted benzoxazol-2-yl, or optionally substituted benzothiazol-2-yl; and r is 1, 2, 3.

2. The compound of claim 1, further represented by a formula:

HT-Ph$^{1a}$-Ph$^{1b}$-Ph$^{1c}$-Py-Het-ET wherein Ph$^{1a}$ is optionally substituted p-phenylene, or HT-Ph$^{1a}$ is 9-phenylcarbazol-3-yl; and Ph$^{1b}$ and Ph$^{1c}$ are independently a bond.

3. The compound of claim 1, wherein r is 1.

4. The compound of claim 1, wherein ET is optionally substituted 1-phenyl-1H-benzo[d]imidazol-2-yl.
5. The compound of claim 1, wherein HT is
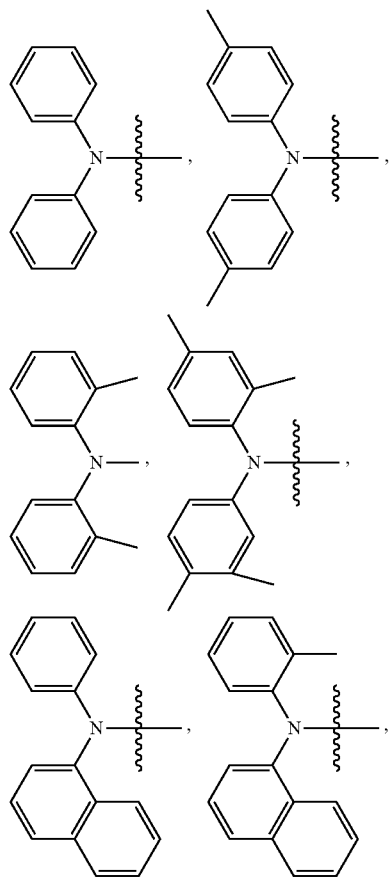
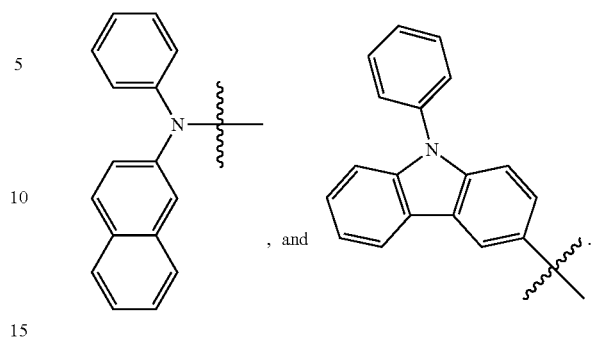
6. The compound of claim 1, wherein ET is
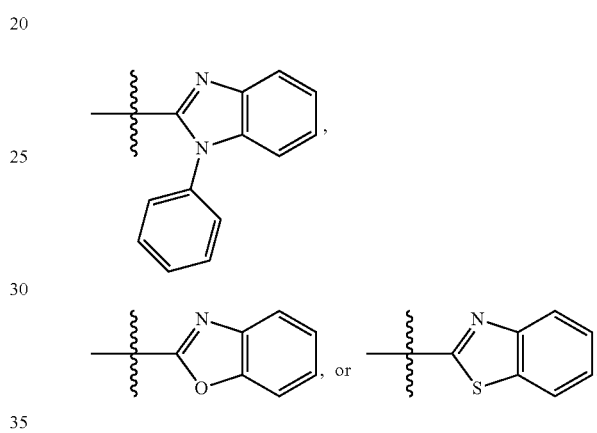
7. The compound of claim 1, wherein the compound is:
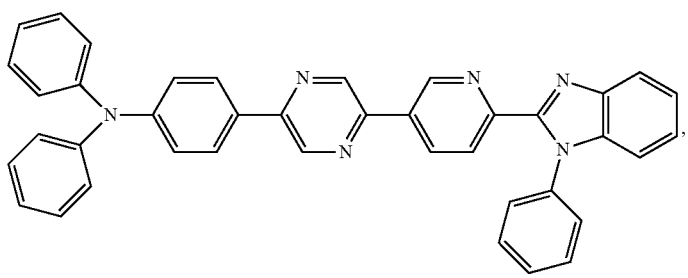
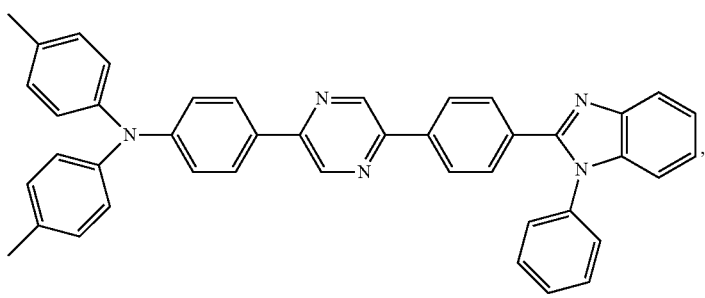

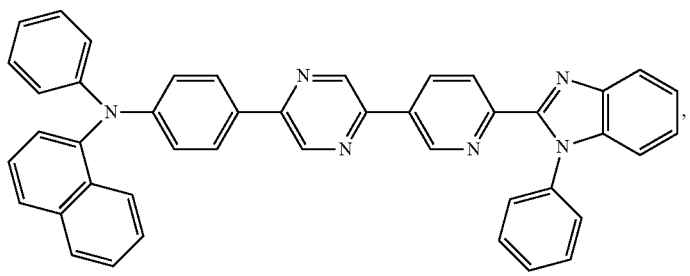
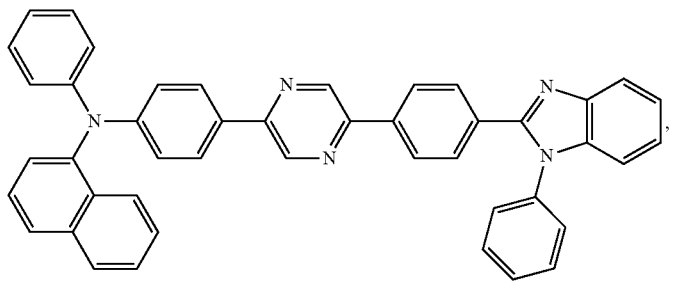
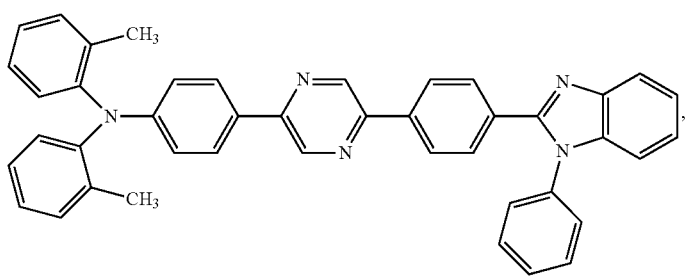
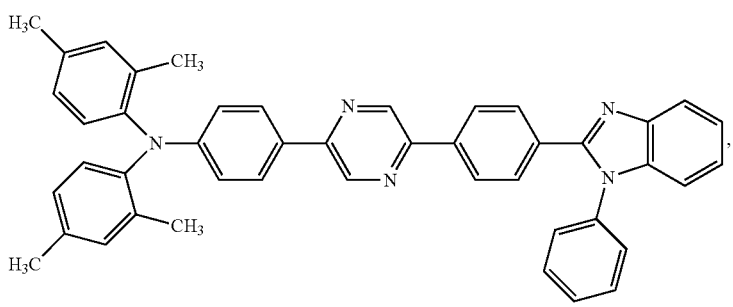
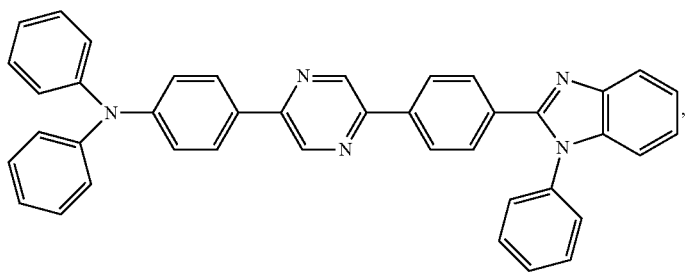
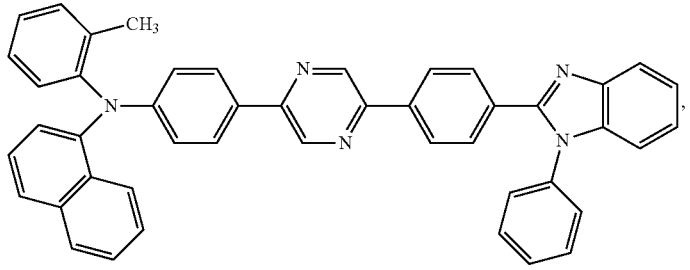

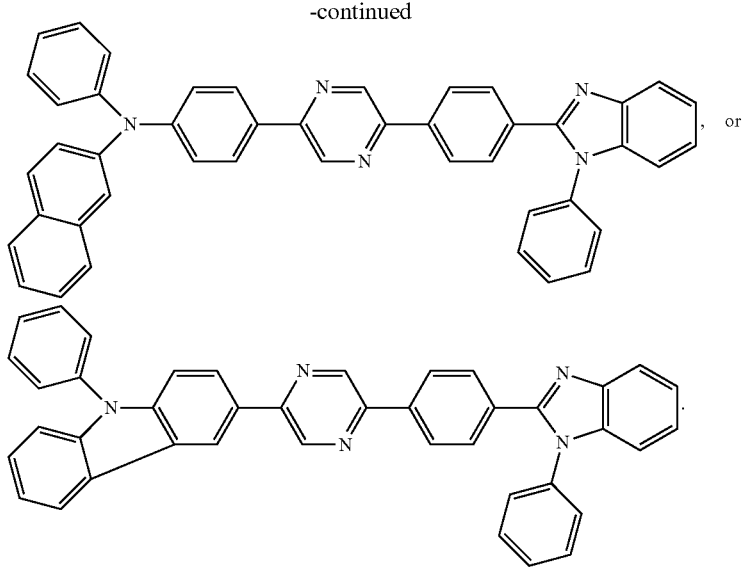

8. The compound of claim 1, wherein the compound is electroluminescent.

9. The compound of claim 8, wherein the compound has a lowest energy triplet having an energy of about 2.5 eV to about 4 eV.

10. A light emitting layer comprising the compound of claim 1.

11. A light emitting device, comprising:
an anode layer comprising a high work function metal;
a cathode layer comprising a low work function metal; and
a light emitting layer comprising a compound of claim 1.

12. The compound of claim 1, wherein Het is optionally substituted p-phenylene.

13. The compound of claim 1, wherein Het is optionally substituted pyridin-2,5-ylene.

14. The compound of claim 1, wherein r is 2.

15. The compound of claim 1, wherein r is 3.

* * * * *